(12) United States Patent
Kose

(10) Patent No.: US 12,156,634 B2
(45) Date of Patent: Dec. 3, 2024

(54) CONTINUUM ROBOT CONTROL DEVICE, CONTINUUM ROBOT CONTROL METHOD, AND PROGRAM

(71) Applicant: CANON KABUSHIKI KAISHA, Tokyo (JP)

(72) Inventor: Hidekazu Kose, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 982 days.

(21) Appl. No.: 17/040,923

(22) PCT Filed: Mar. 13, 2019

(86) PCT No.: PCT/JP2019/010331
§ 371 (c)(1),
(2) Date: Sep. 23, 2020

(87) PCT Pub. No.: WO2019/181694
PCT Pub. Date: Sep. 26, 2019

(65) Prior Publication Data
US 2021/0369081 A1    Dec. 2, 2021

(30) Foreign Application Priority Data

Mar. 23, 2018  (JP) ................................ 2018-056793
Jan. 31, 2019  (JP) ................................ 2019-016022

(51) Int. Cl.
*A61B 1/00*    (2006.01)
*A61B 1/005*   (2006.01)
(Continued)

(52) U.S. Cl.
CPC ........ *A61B 1/00006* (2013.01); *A61B 1/0057* (2013.01); *B25J 9/104* (2013.01); *B25J 18/06* (2013.01)

(58) Field of Classification Search
CPC .............. A61B 1/00006; A61B 1/0057; A61B 2034/301; A61B 2090/061; A61B 34/71;
(Continued)

(56) References Cited

U.S. PATENT DOCUMENTS 9,333,650 B2    5/2016  Bajo
9,364,289 B2 *  6/2016  Zinn .................... A61B 34/30
(Continued)

FOREIGN PATENT DOCUMENTS

CN    102170835 A    8/2011
CN    105342704 A    2/2016
(Continued)

OTHER PUBLICATIONS

Kinematic Modeling of the Constant Curvature Continuum Line Drive Robot (Year: 2016).*
(Continued)

*Primary Examiner* — Jonathan L Sample
*Assistant Examiner* — Shaheda Shabnam Hoque
(74) *Attorney, Agent, or Firm* — Canon U.S.A., Inc. IP Division

(57) ABSTRACT

A continuum robot control device, configured to control operations of a continuum robot having a bendable portion that is bent by driving at least part of a plurality of wires, includes a kinematics computing unit that computes a driving amount $l_{k1b}$ of the at least part of the plurality of wires, based on a target bending angle that is a target value for a bending angle of the bendable portion, a compensation amount computing unit that computes a compensation amount for compensation of the driving amount $l_{k1b}$, based on the target bending angle, and a displacement of one of the plurality of wires at the target bending angle, and an adding unit and position control unit that set a driving control amount of performing driving control of the at least part of
(Continued)

the plurality of wires, based on the driving amount and the compensation amount obtained by computation.

9 Claims, 33 Drawing Sheets

(51) Int. Cl.
*B25J 9/10* (2006.01)
*B25J 18/06* (2006.01)

(58) Field of Classification Search
CPC . A61B 34/30; B25J 9/104; B25J 18/06; B25J 9/06; B25J 9/1615; B25J 9/1635; G05B 2219/40236
See application file for complete search history.

(56) References Cited

U.S. PATENT DOCUMENTS

| | | | | |
|---|---|---|---|---|
| 10,753,439 | B2* | 8/2020 | Awtar | F16H 19/0672 |
| 10,959,797 | B2* | 3/2021 | Licht | A61B 34/76 |
| 11,457,987 | B2* | 10/2022 | He | A61B 34/77 |
| 2007/0168081 | A1* | 7/2007 | Shin | B25J 19/007 |
| | | | | 700/245 |
| 2009/0171271 | A1* | 7/2009 | Webster | A61B 17/3421 |
| | | | | 604/95.01 |
| 2010/0152898 | A1 | 6/2010 | Reiland | |
| 2011/0230894 | A1* | 9/2011 | Simaan | A61B 1/00183 |
| | | | | 606/130 |
| 2013/0090763 | A1 | 4/2013 | Simaan | |
| 2013/0345877 | A1 | 12/2013 | Kose | |
| 2014/0316434 | A1* | 10/2014 | Simaan | A61B 34/74 |
| | | | | 606/130 |
| 2014/0330432 | A1* | 11/2014 | Simaan | B25J 9/1625 |
| | | | | 700/250 |
| 2015/0047452 | A1* | 2/2015 | Wolf | B25J 17/0275 |
| | | | | 901/28 |
| 2015/0088161 | A1* | 3/2015 | Hata | A61B 1/009 |
| | | | | 606/130 |
| 2016/0016319 | A1* | 1/2016 | Remirez | A61B 34/71 |
| | | | | 74/490.04 |
| 2017/0182659 | A1 | 6/2017 | Simaan | |
| 2018/0296282 | A1 | 10/2018 | Kose | |
| 2018/0304458 | A1 | 10/2018 | Takagi | |
| 2021/0128888 | A1* | 5/2021 | Desai | A61M 25/09041 |

FOREIGN PATENT DOCUMENTS

| | | |
|---|---|---|
| CN | 106625631 A | 5/2017 |
| EP | 2786721 A | 10/2014 |
| EP | 3025632 A | 6/2016 |
| IN | 103874524 A | 6/2014 |
| JP | 2010-220961 A | 10/2010 |
| JP | 2015-023950 A | 2/2015 |
| JP | 2018-008335 A | 1/2018 |
| KR | 2018-0045652 A | 5/2018 |
| WO | 2015/042453 A | 3/2015 |
| WO | 2016/136353 A | 9/2016 |
| WO | 2018/012360 A | 1/2018 |

OTHER PUBLICATIONS

Y. Tian, S. Yang, H. Geng, W. Wang and L. Li, "Kinematic modeling of the constant curvature continuum line drive robot," 2016 IEEE International Conference on Robotics and Biomimetics (ROBIO), Qingdao, China, 2016, pp. 289-294 (Year: 2016).*

H. - S. Yoon, J. Jeon, J. H. Chung and B. - J. Yi, "Error compensation for a 2 DOF bendable endoscope mechanism," 2013 13th International Conference on Control, Automation and Systems (ICCAS 2013), Gwangju, Korea (South), 2013, pp. 862-865 (Year: 2013).*

Xu, K. et al., "An Experimental Kinestatic Comparison between Continuum Manipulators with Structural Variations", IEEE International Conference on Robotics and Automation (ICRA), May 31-Jun. 7, 2013, pp. 3258-3264.

Kato, T. et al., Extended Kinematic Mapping of Tendon-Driven Continuum Robot for Neuroendoscopy, IEEE/RSJ International Conference on Intelligent Robots and Systems, Sep. 14-18, 2014, pp. 1997-2002.

Zhou, X. et al., "Analysis of Under-Actuated Snake Arm Robot", 3rd International Conference on Electromechanical Control Technology and Transportation (ICECTT 2018), Jan. 2018, pp. 414-422.

Ku, K. et al., "Analytic Formulation for Kinematics, Statics, and Shape Restoration of Multibackbone Continuum Robots Via Elliptic Integrals", Journal of Mechanisms and Robotics, Feb. 2020, pp. 1-13, vol. 2.

* cited by examiner

[Fig. 1]
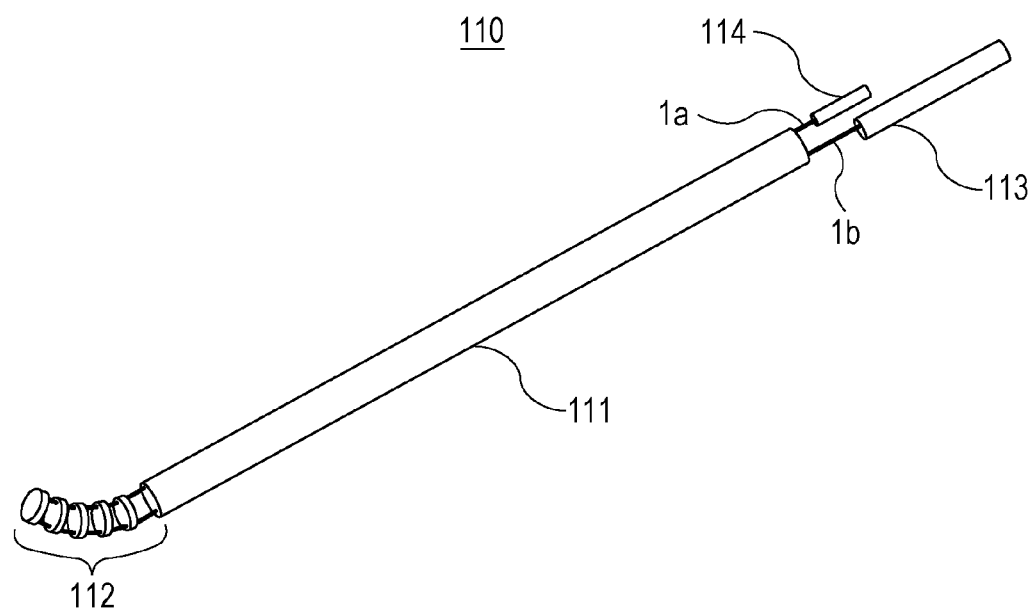

[Fig. 2]
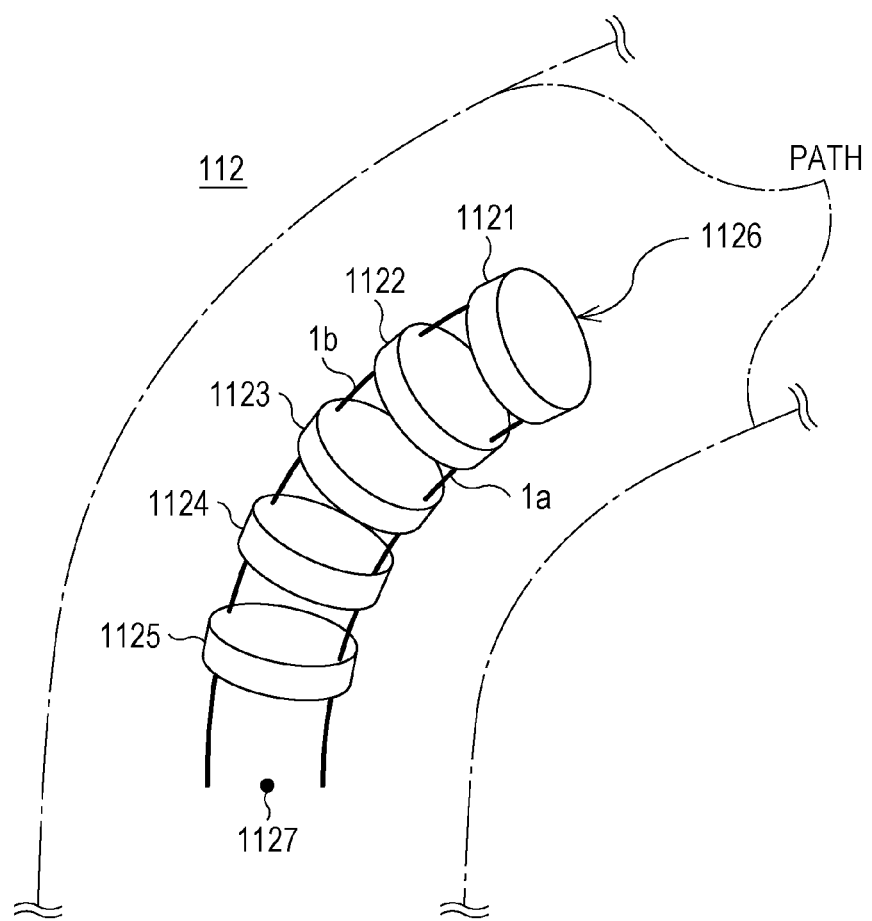

[Fig. 3]
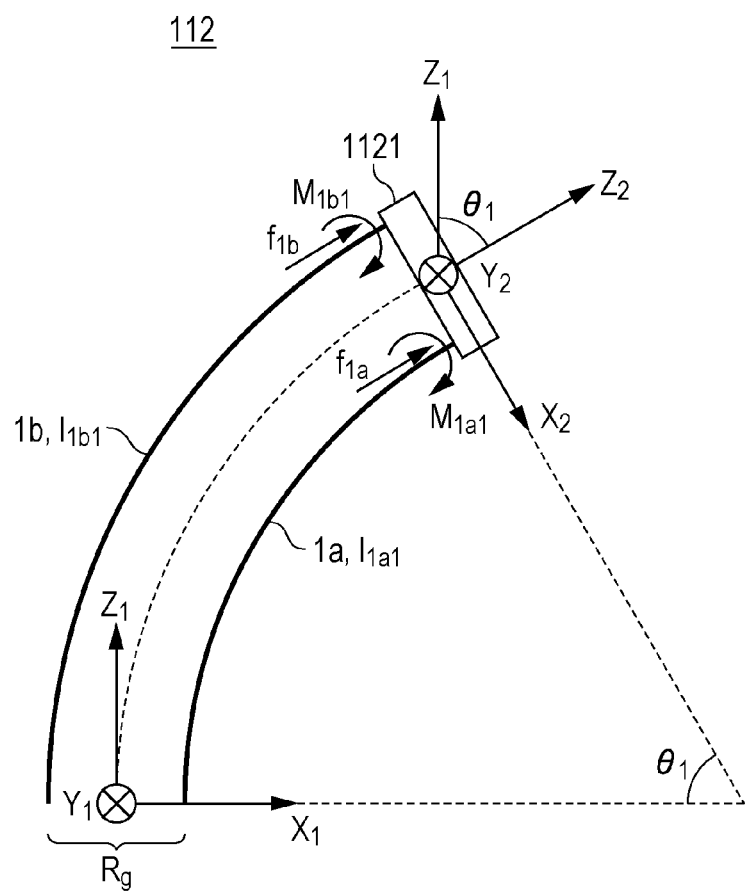

[Fig. 4]
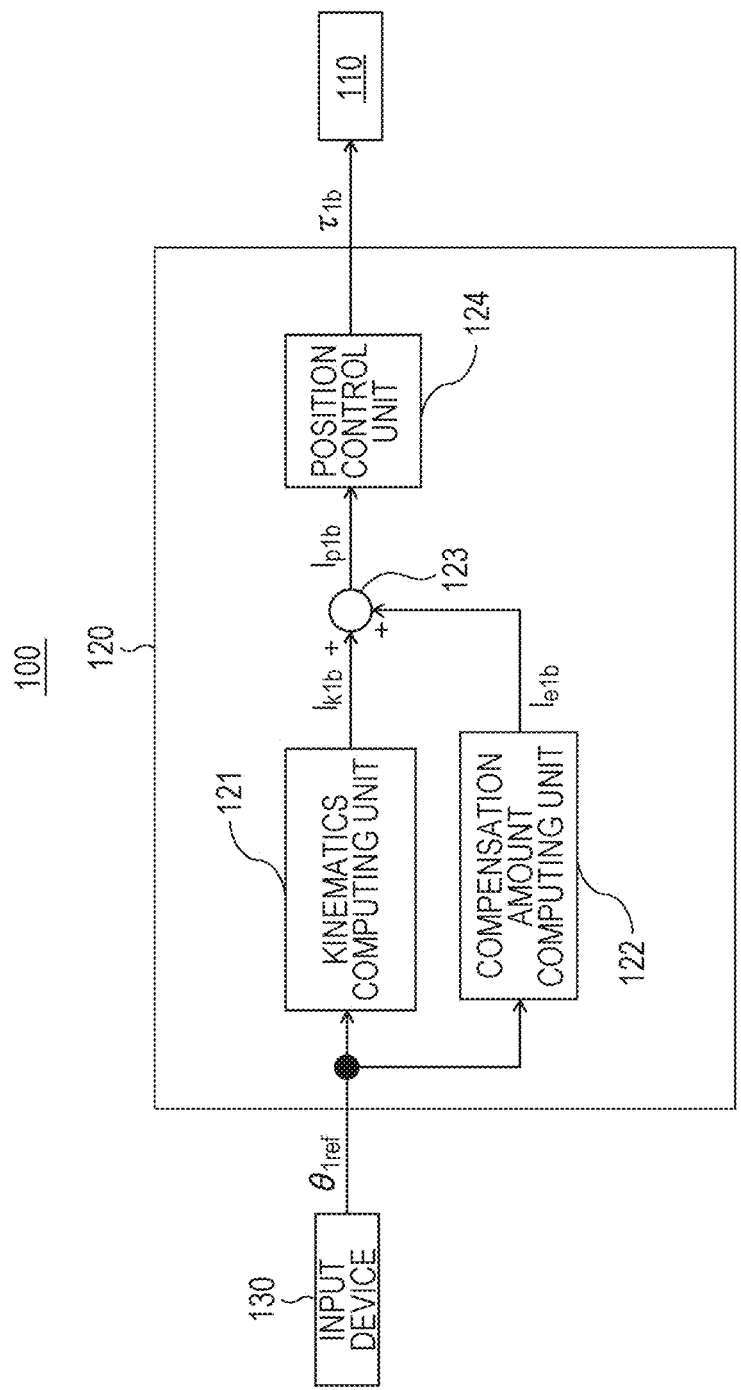

[Fig. 5]
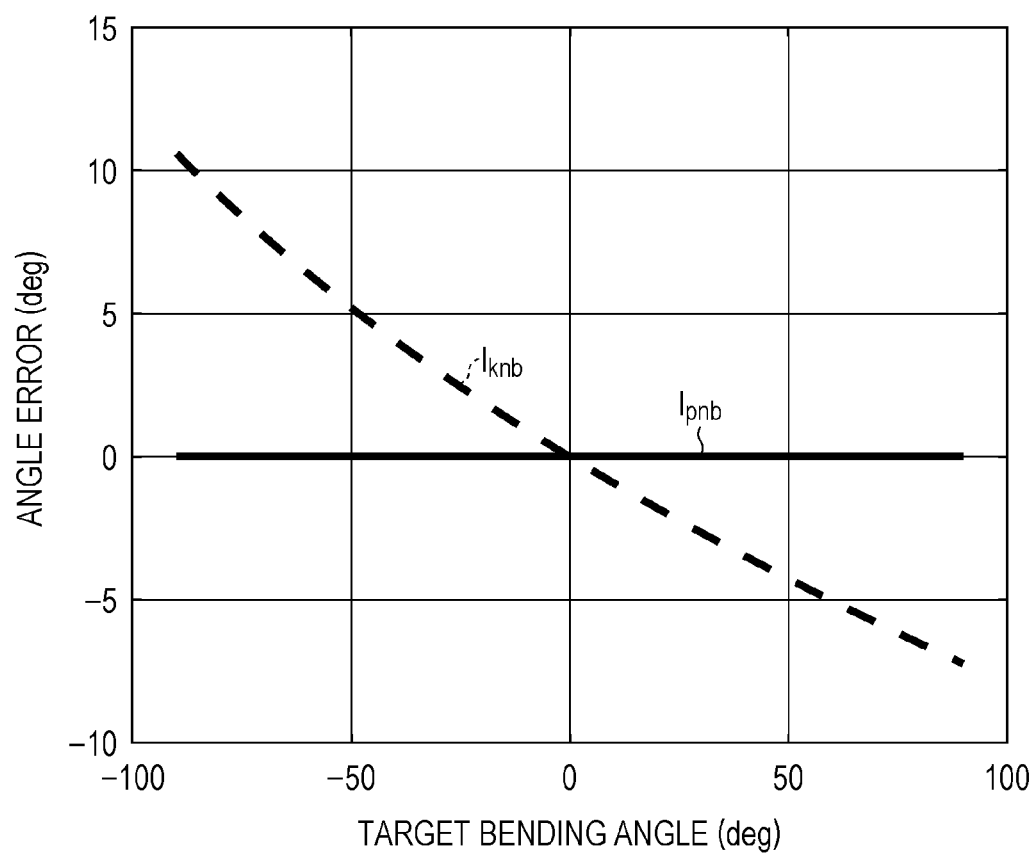

[Fig. 6]
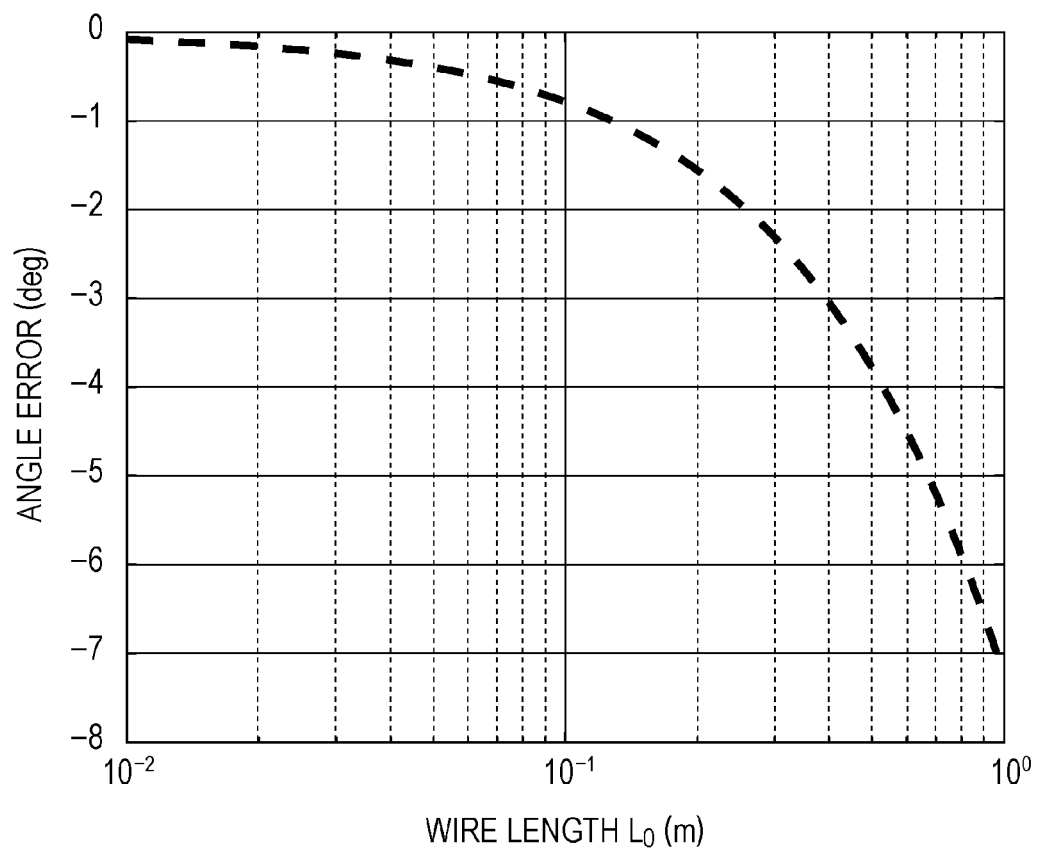

[Fig. 7]
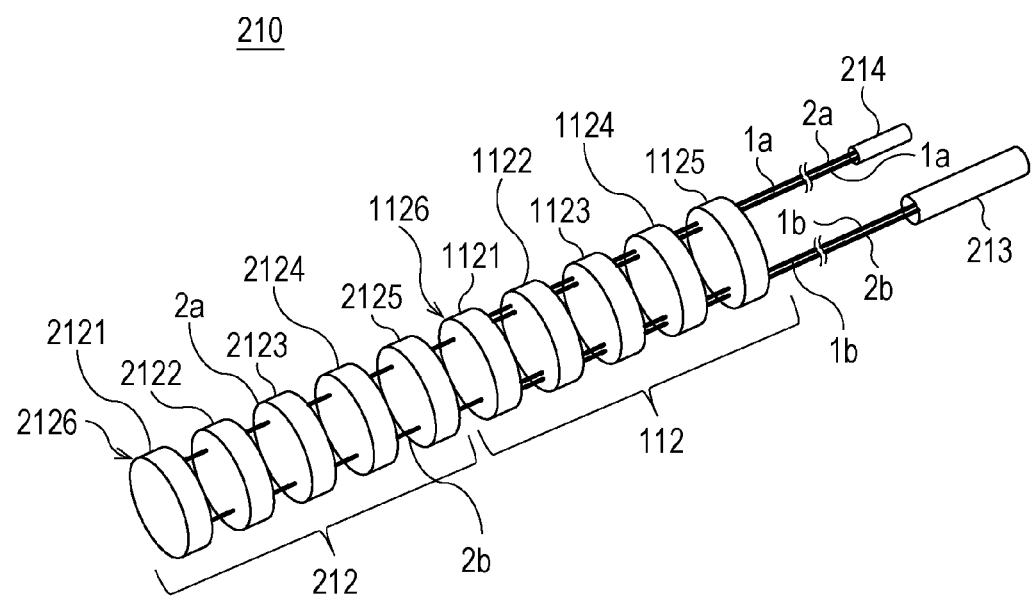

[Fig. 8]
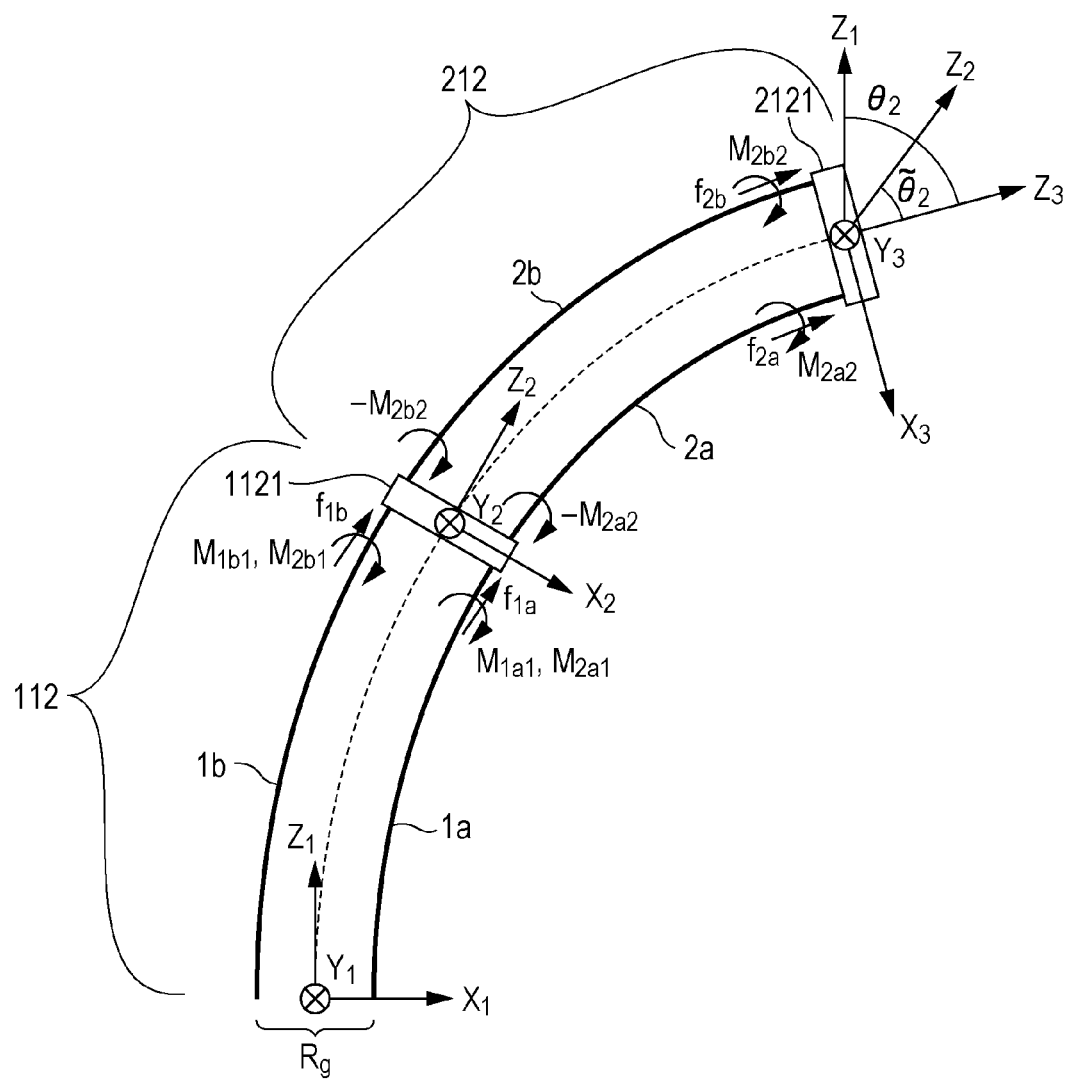

[Fig. 9]
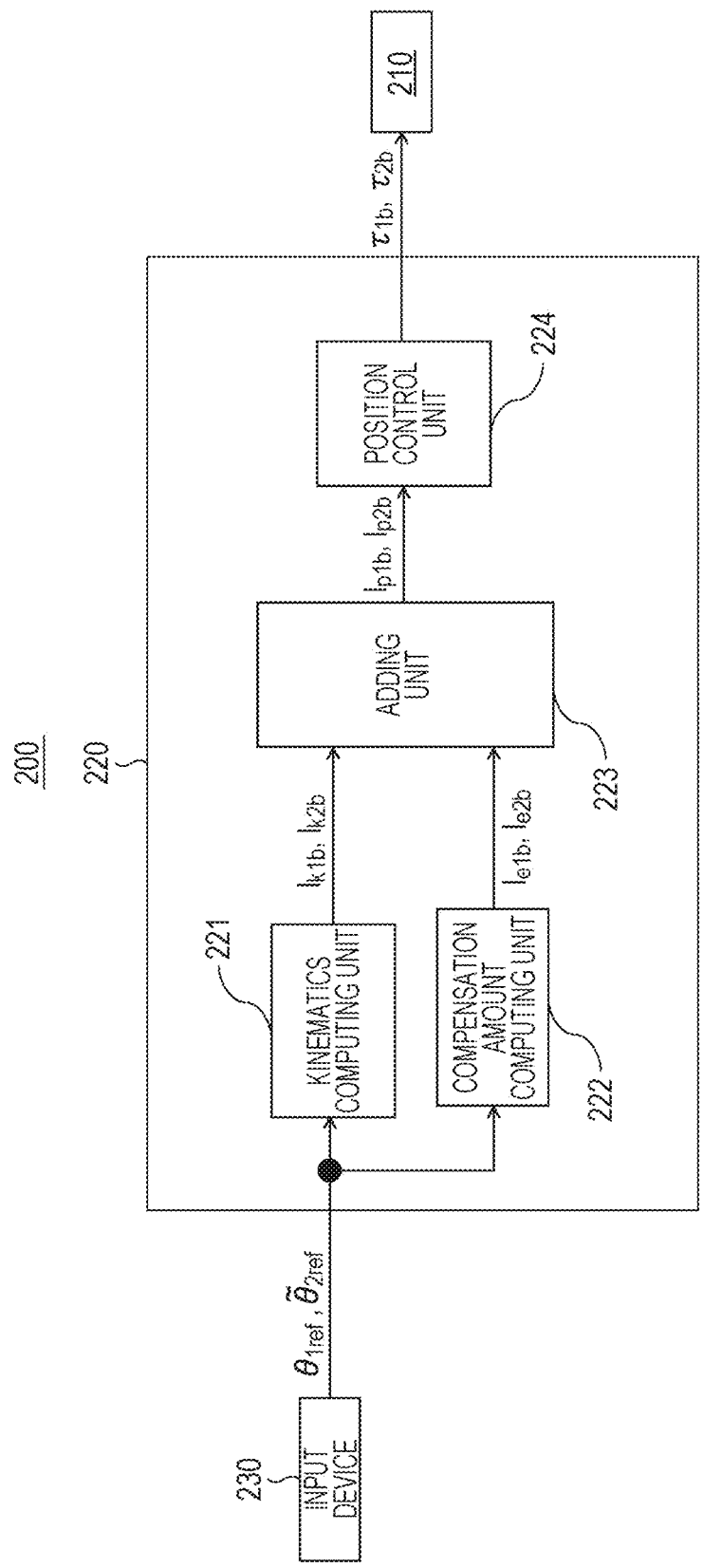

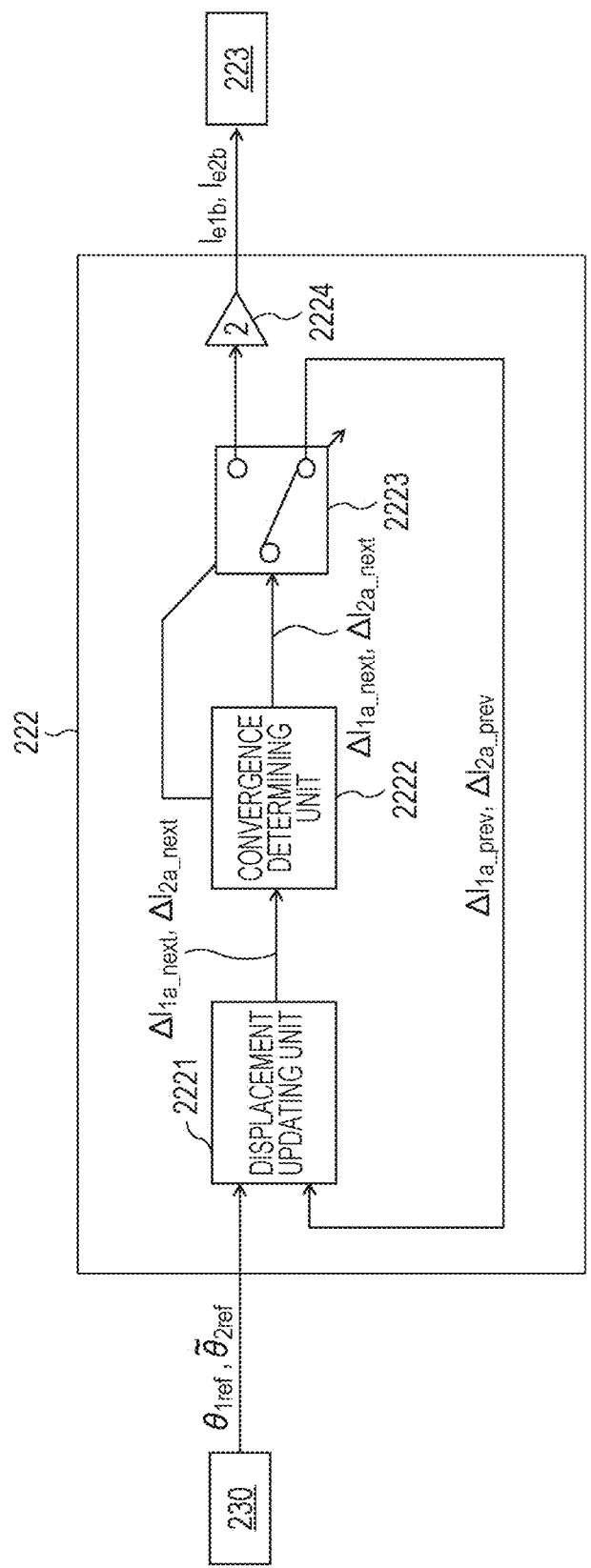
[Fig. 10]

[Fig. 11]
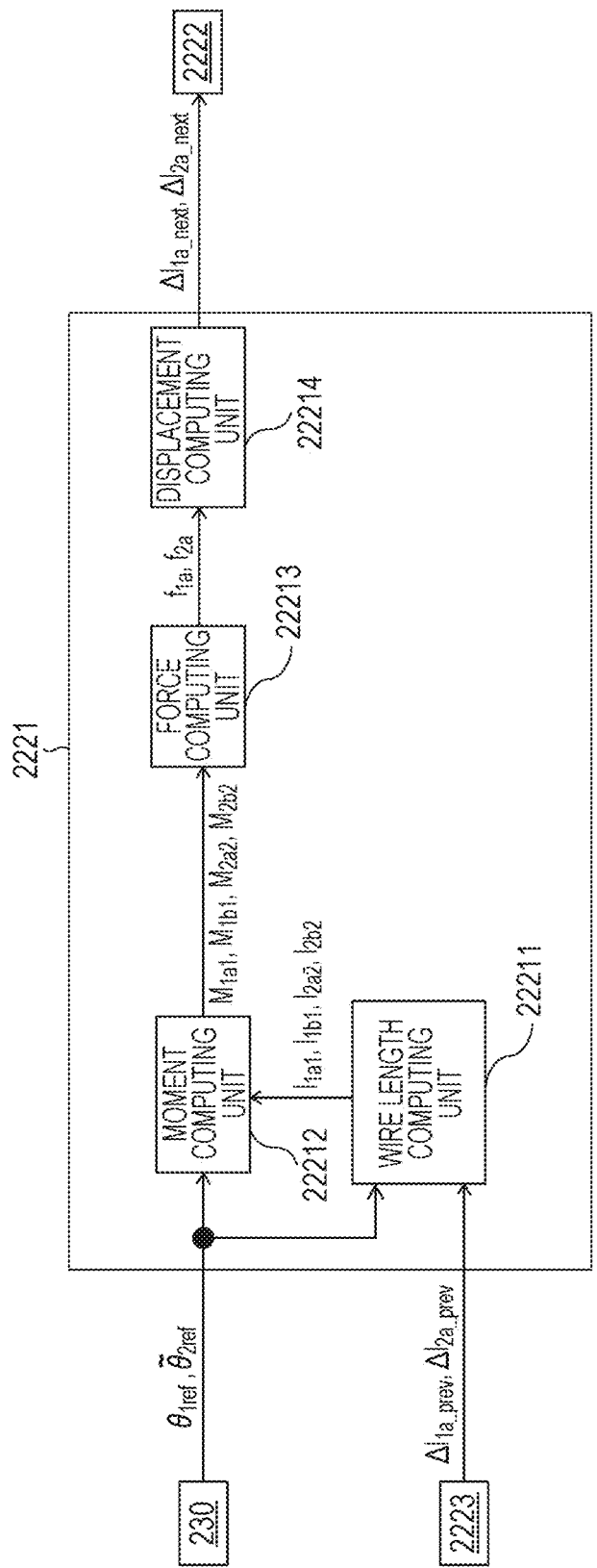

[Fig. 12]
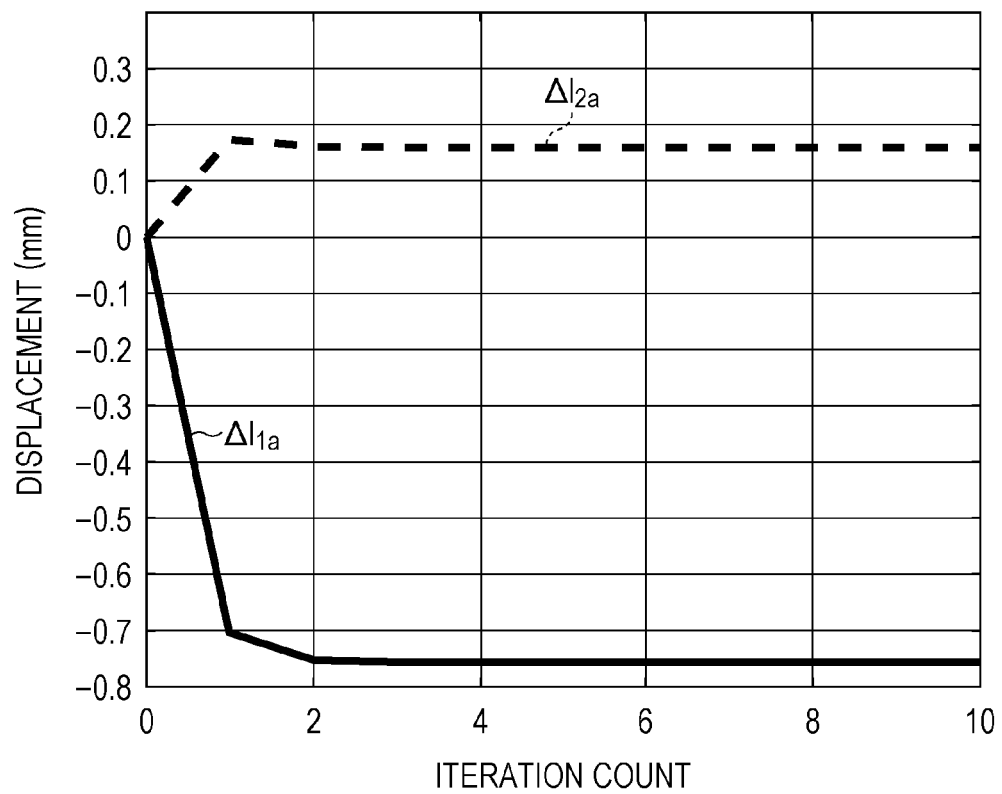

[Fig. 13A]
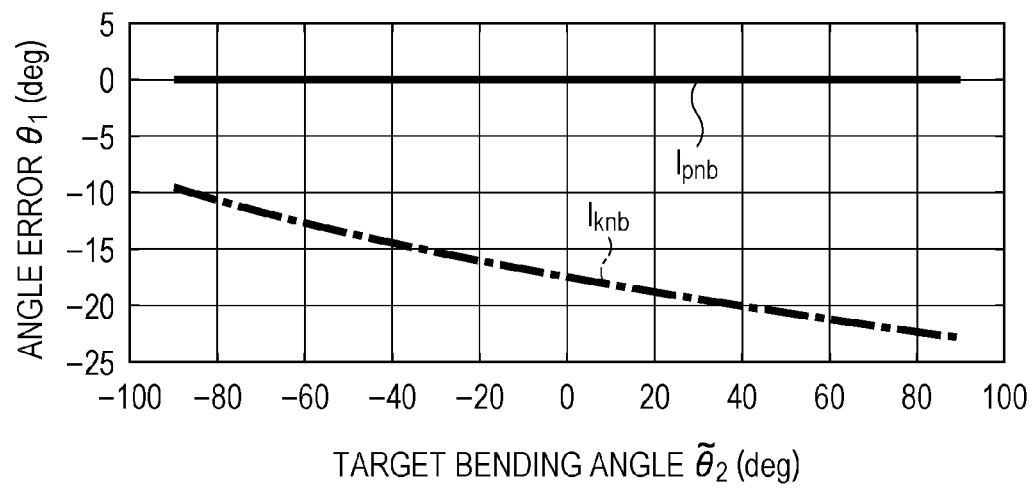
[Fig. 13B]
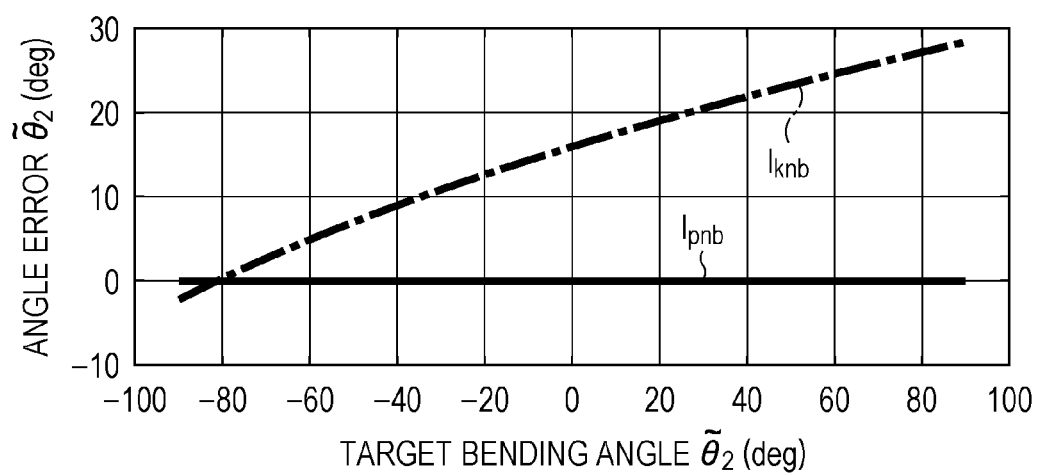

[Fig. 14]
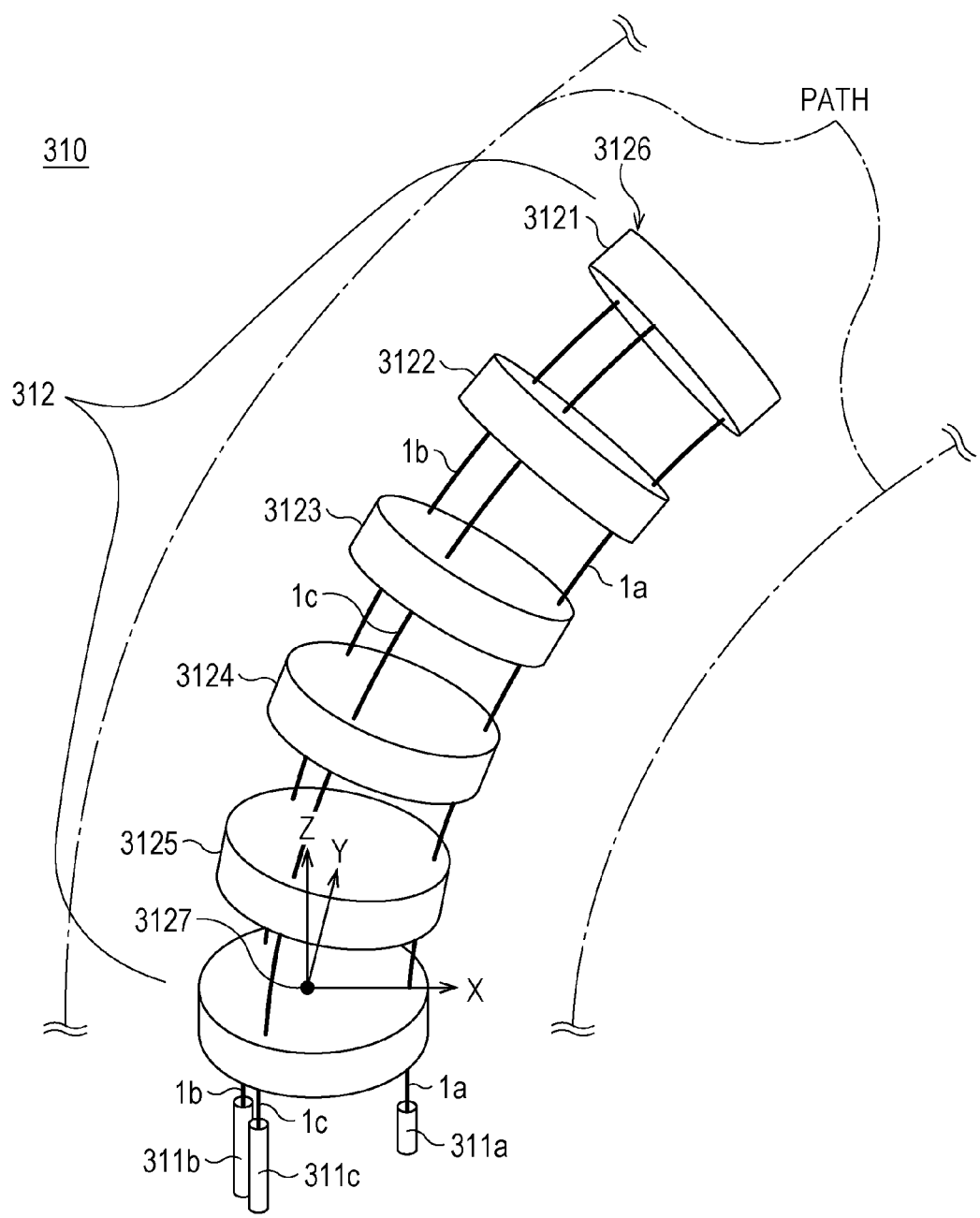

[Fig. 15]
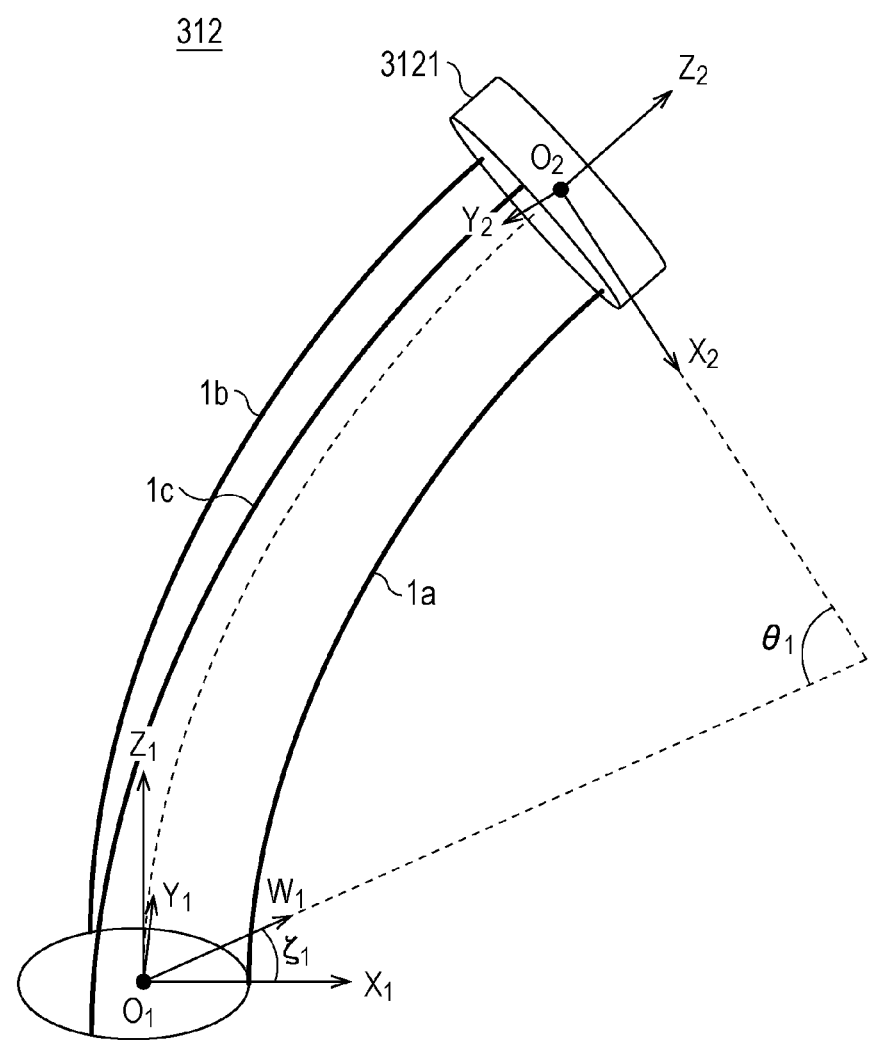

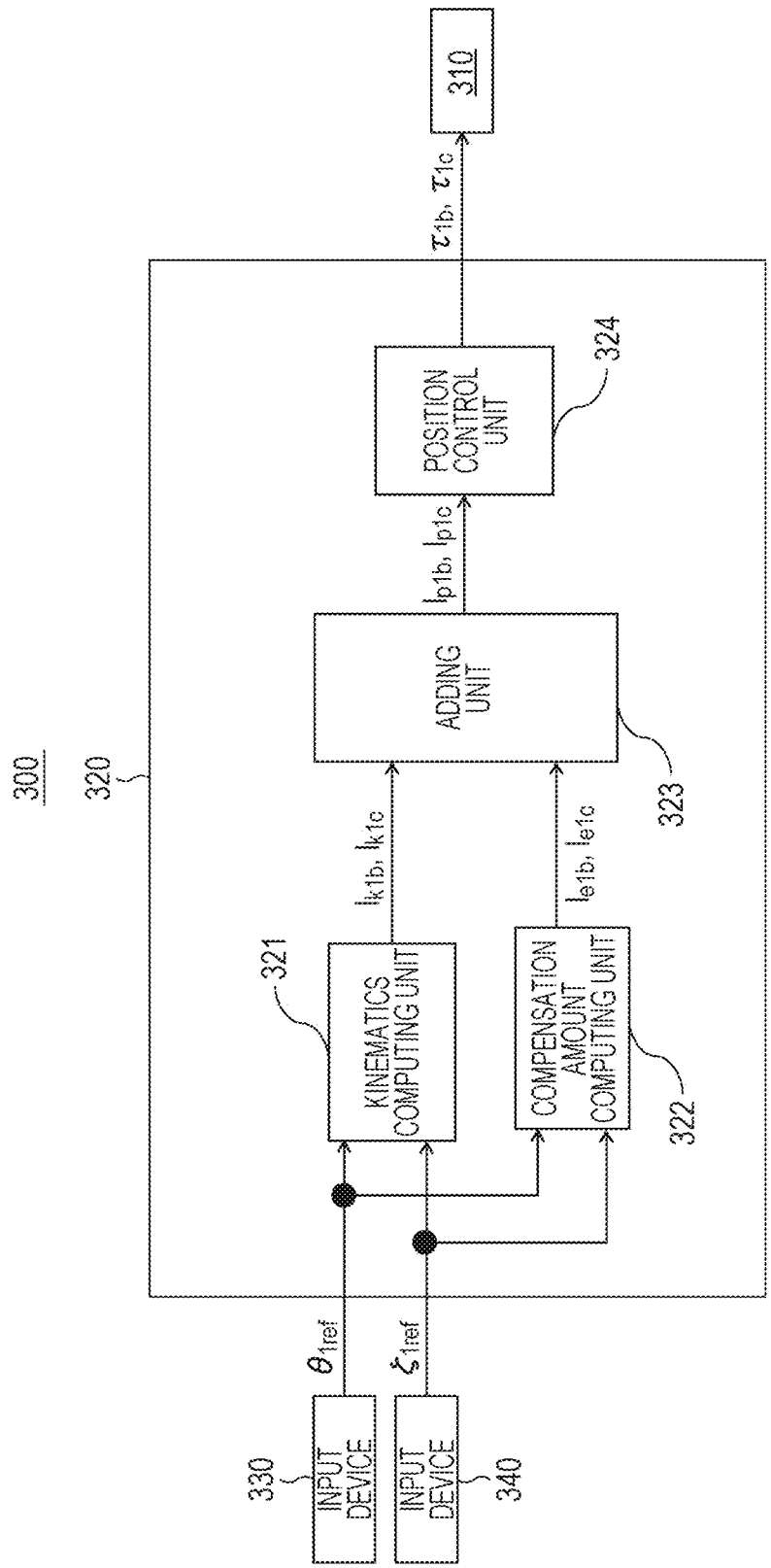

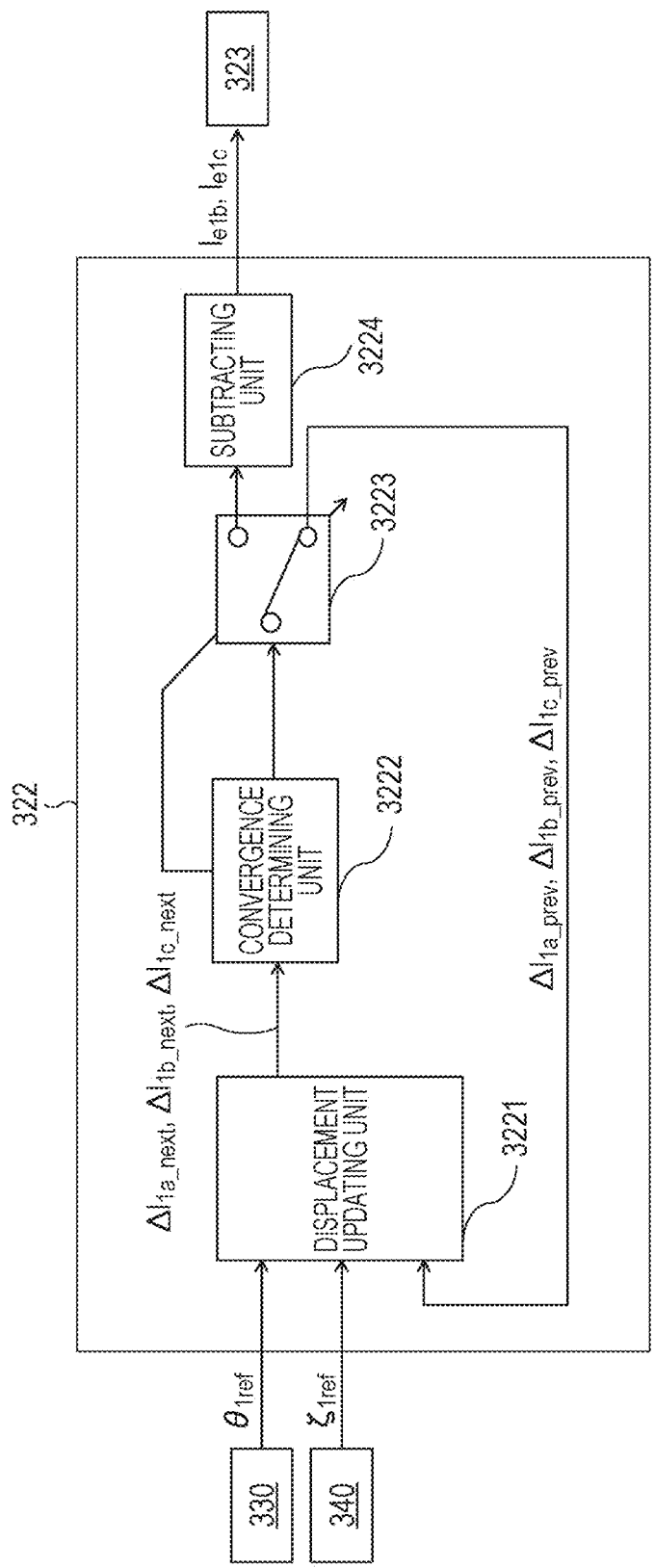

[Fig. 18]
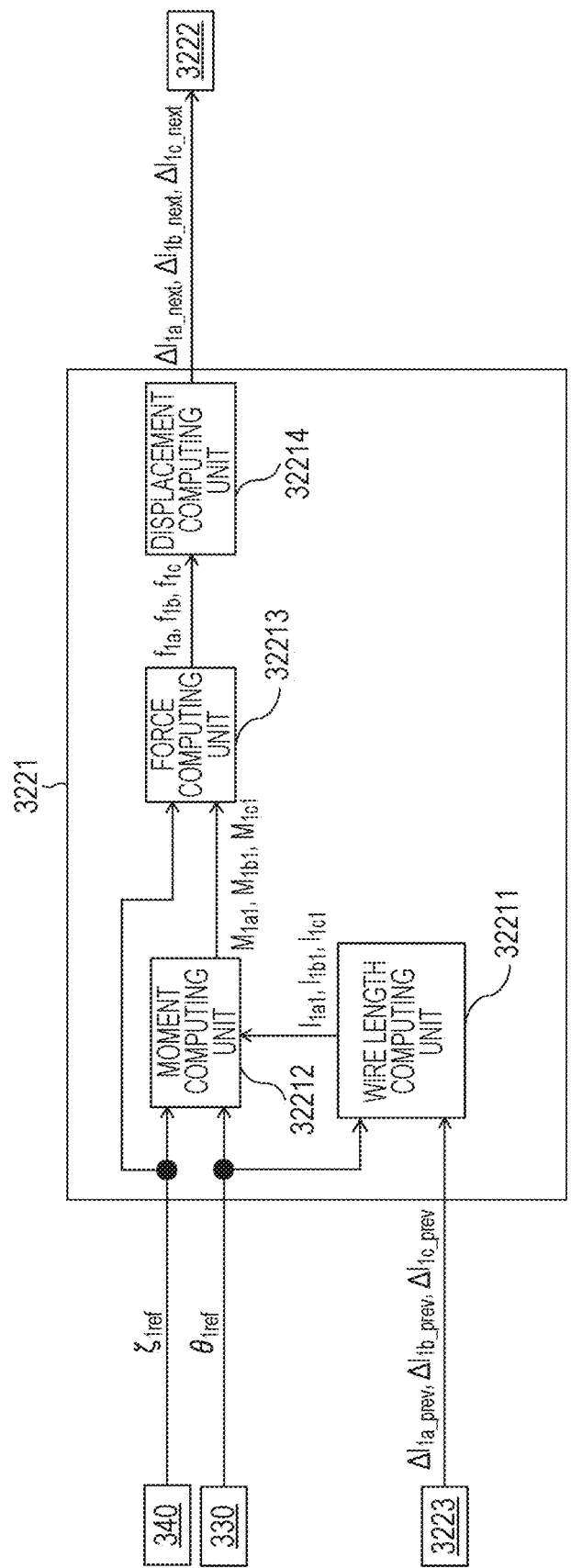

[Fig. 19]
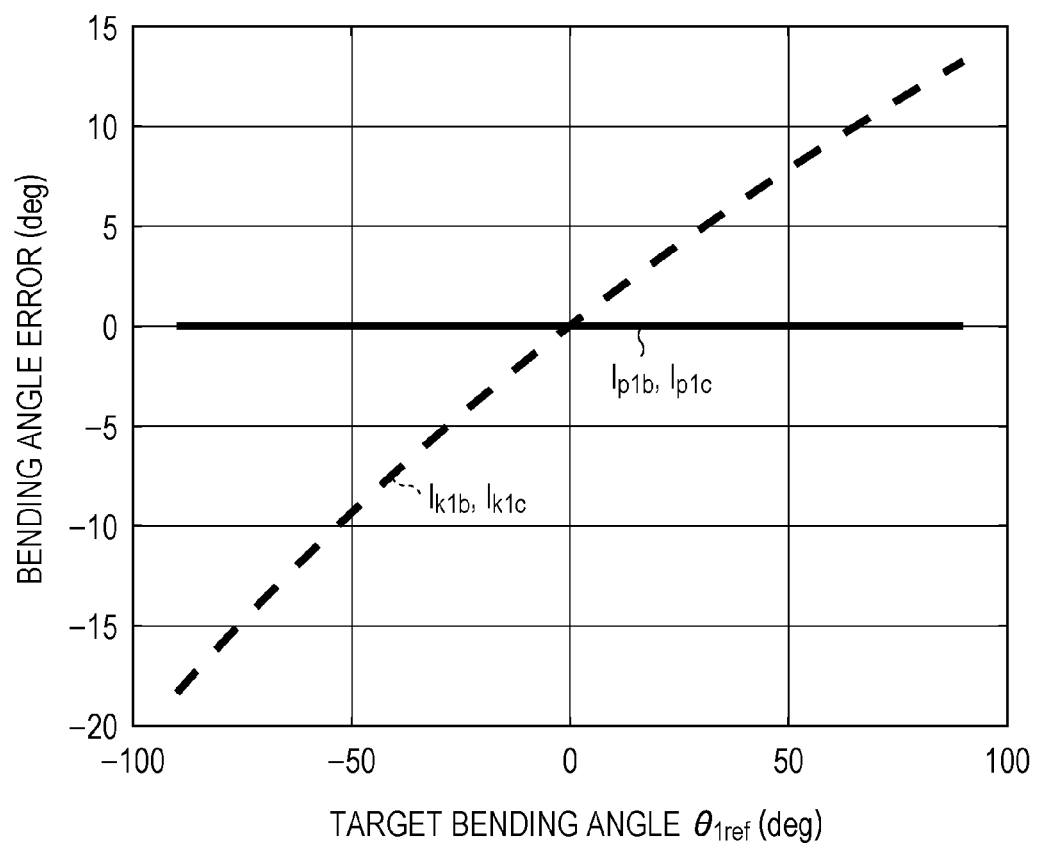

[Fig. 20]
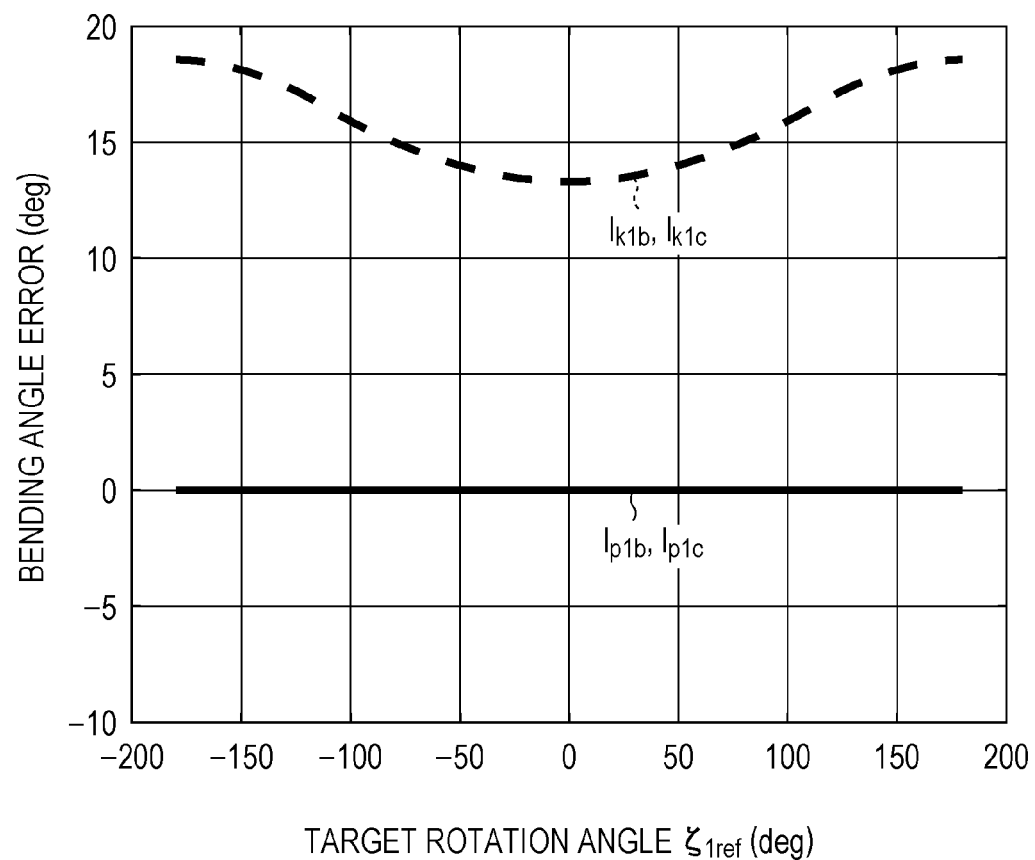

[Fig. 21]
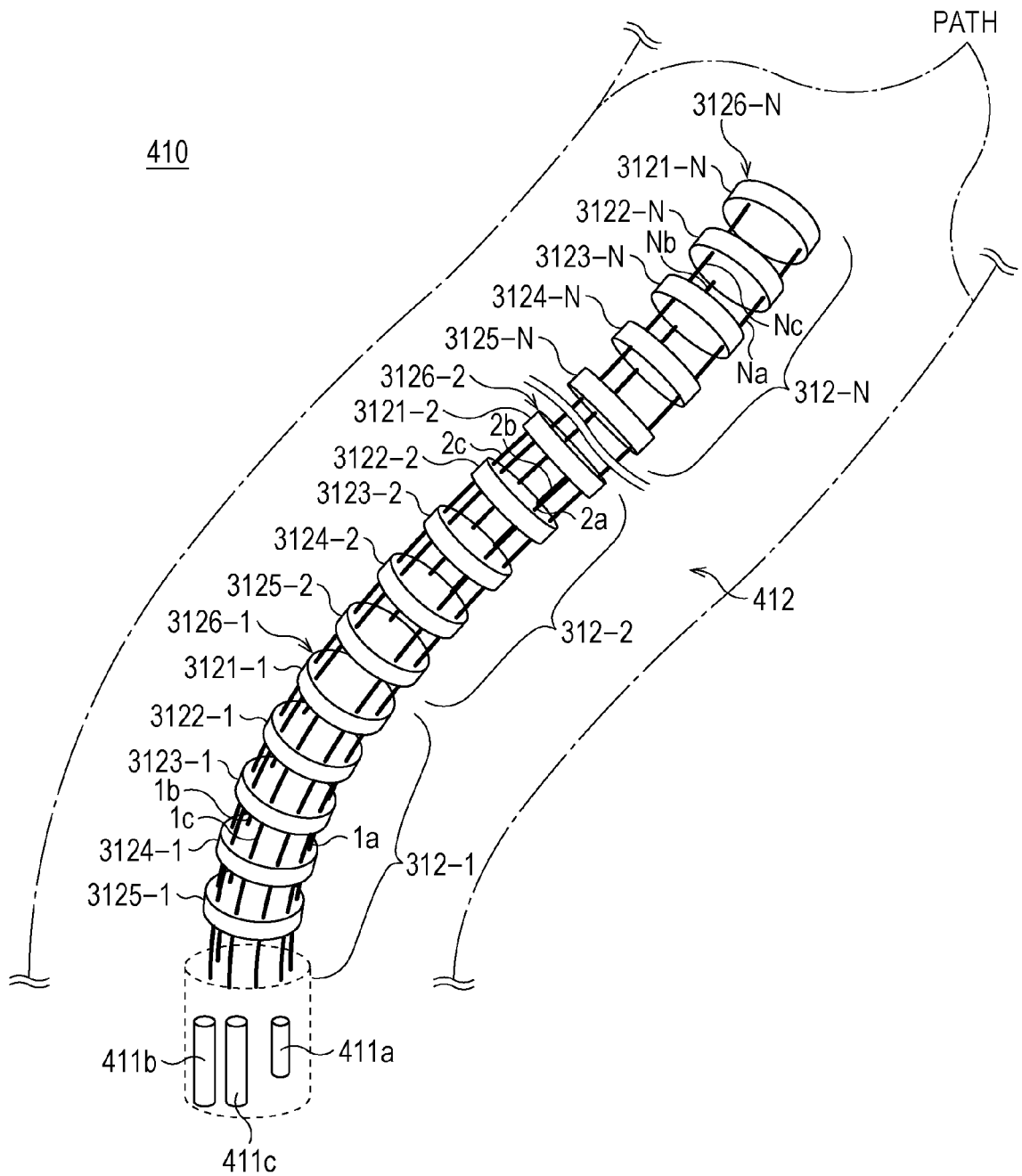

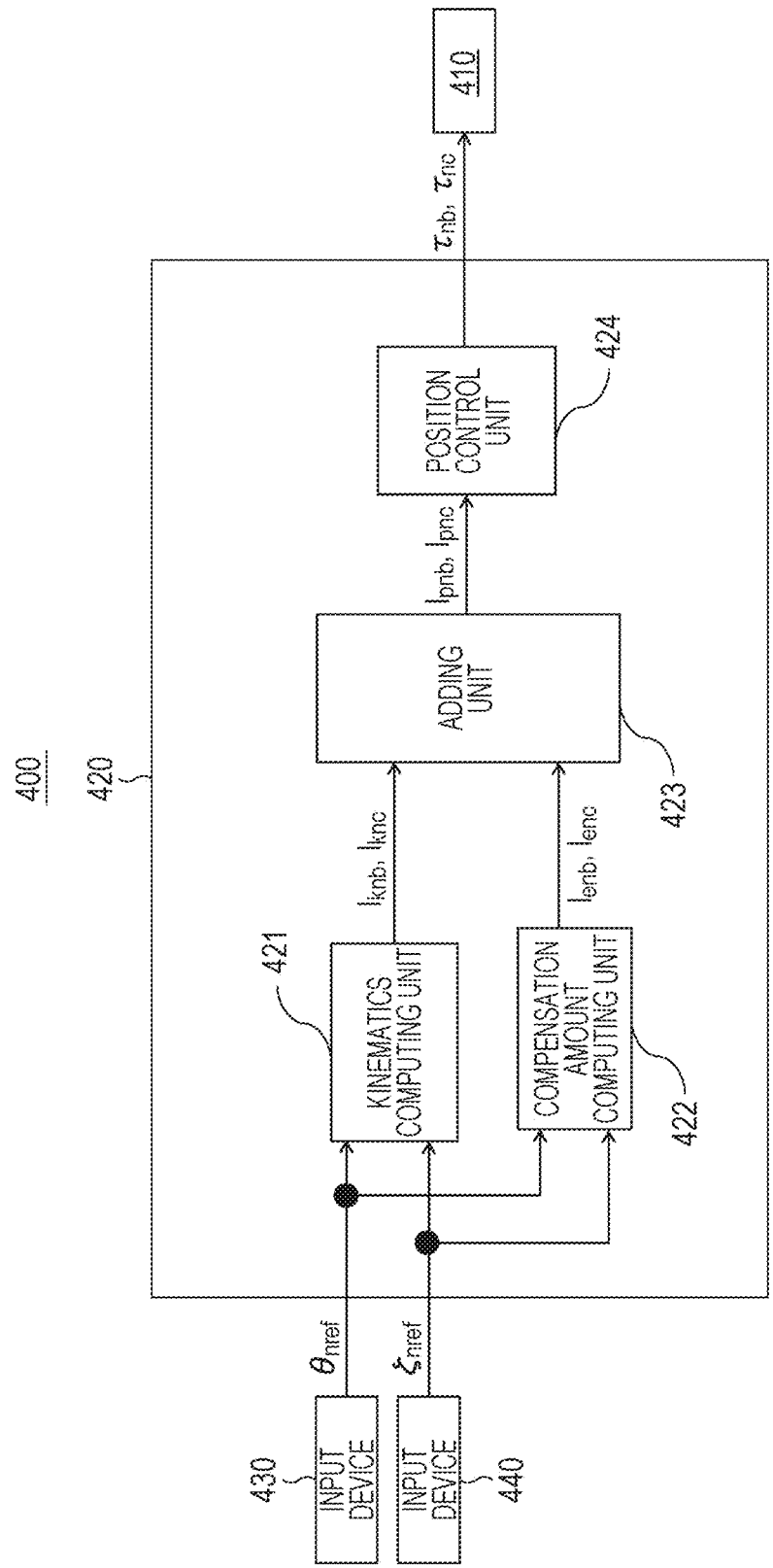
[Fig. 22]

[Fig. 23]
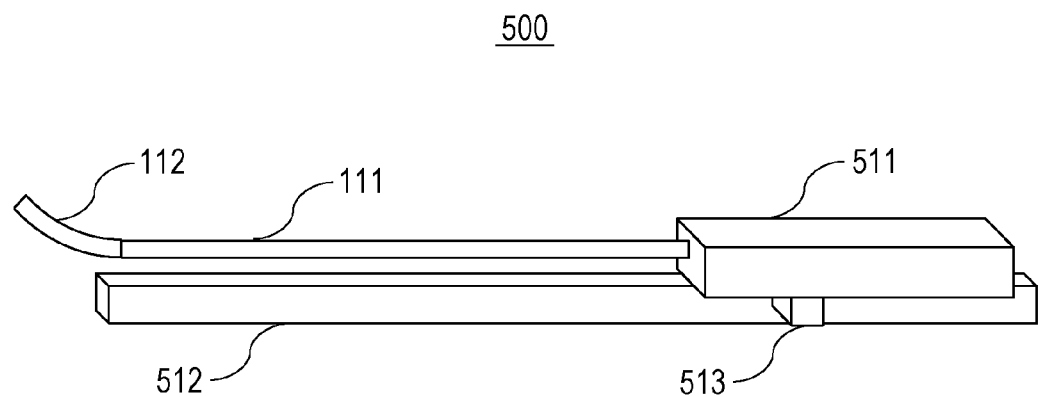

[Fig. 24]
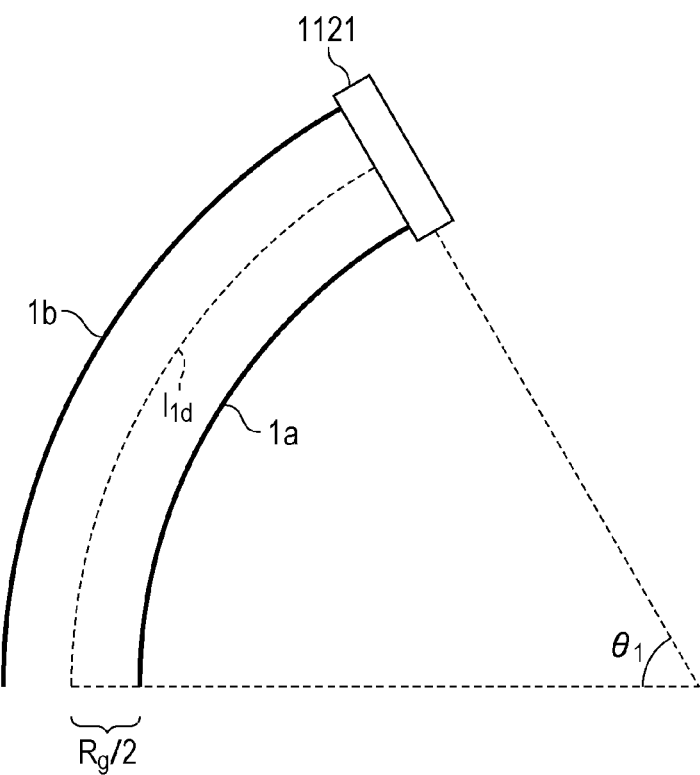

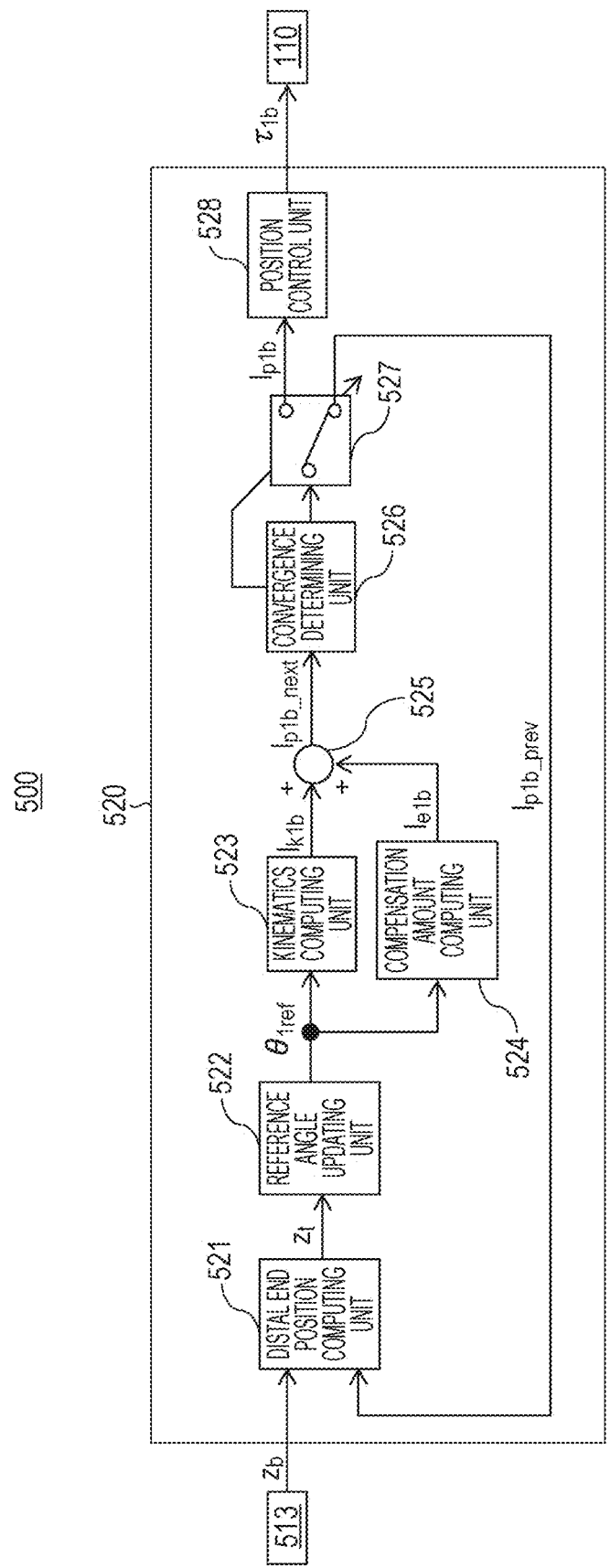
[Fig. 25]

[Fig. 26A]
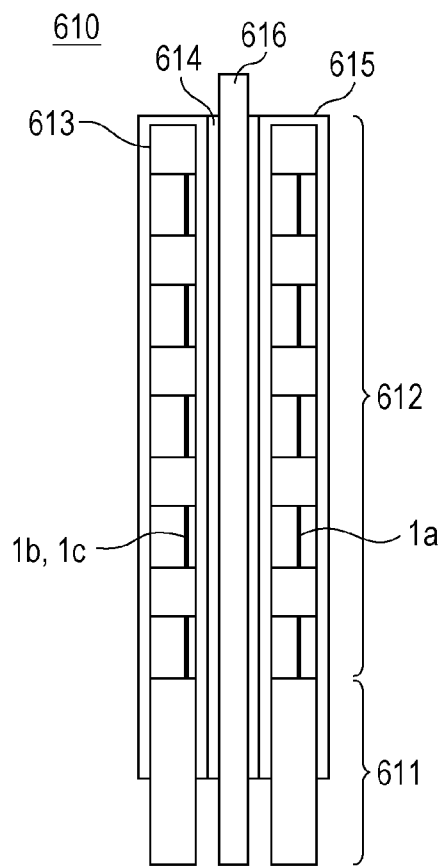
[Fig. 26B]
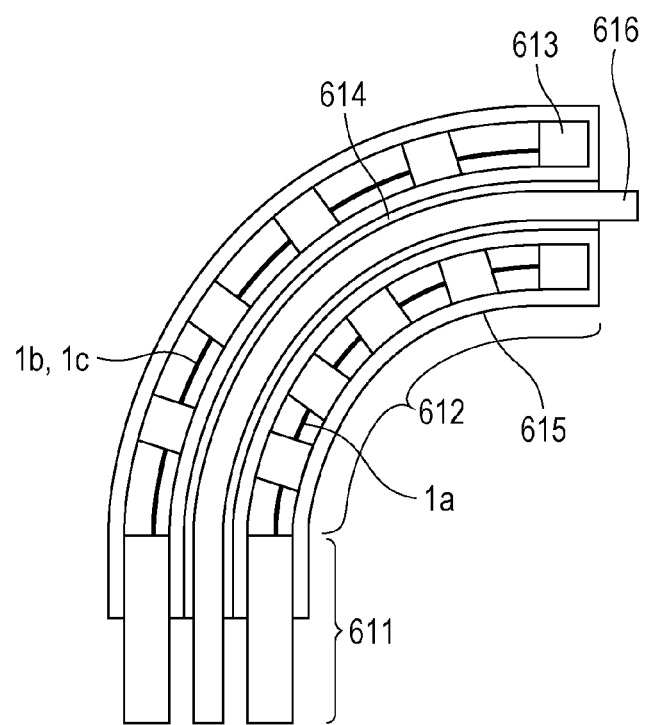

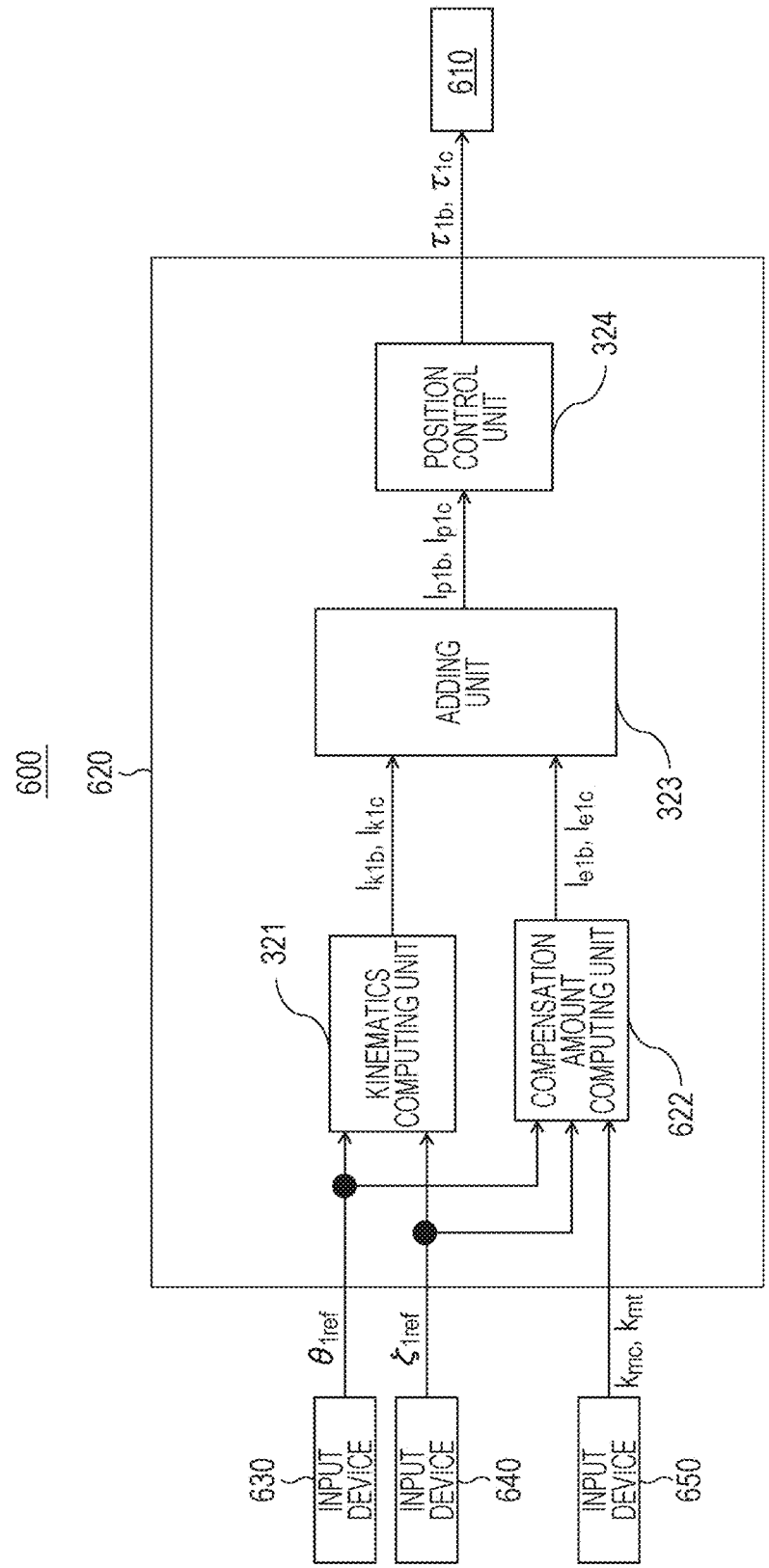

[Fig. 28]
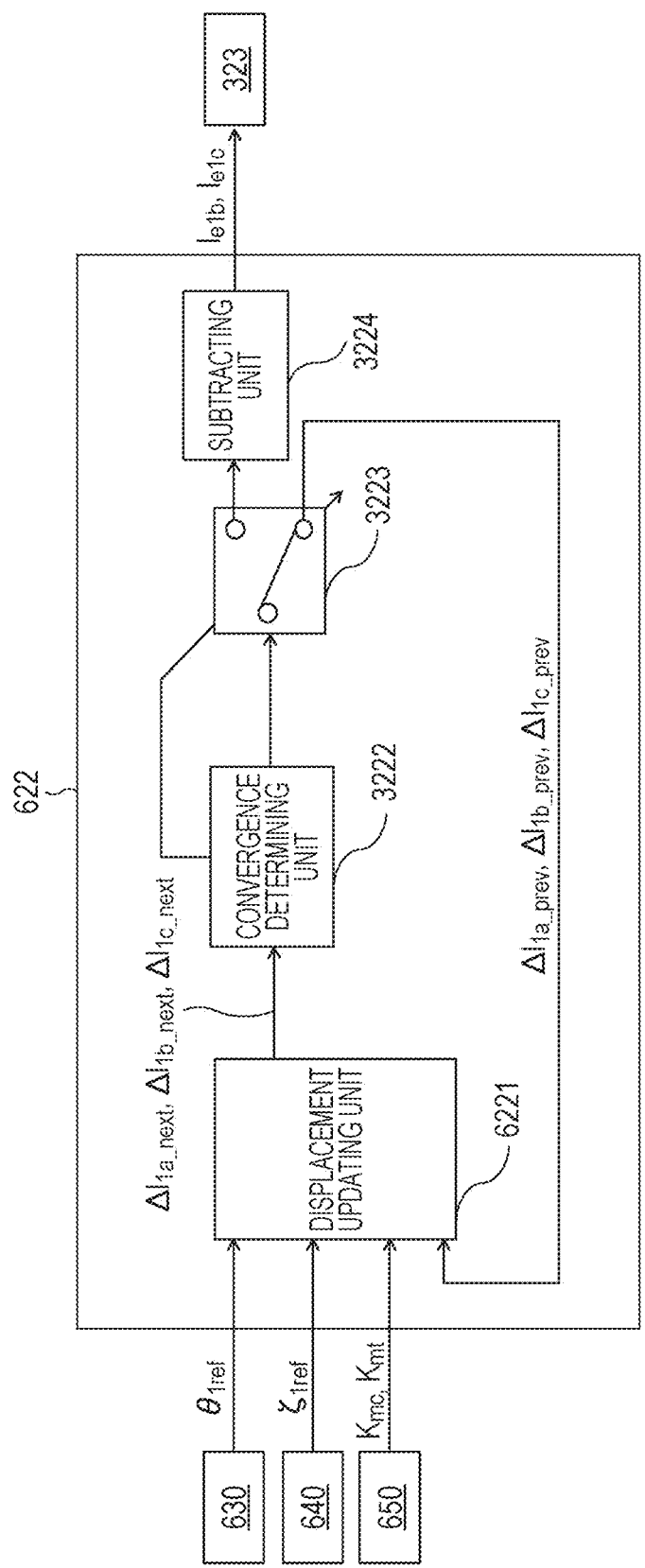

[Fig. 29]
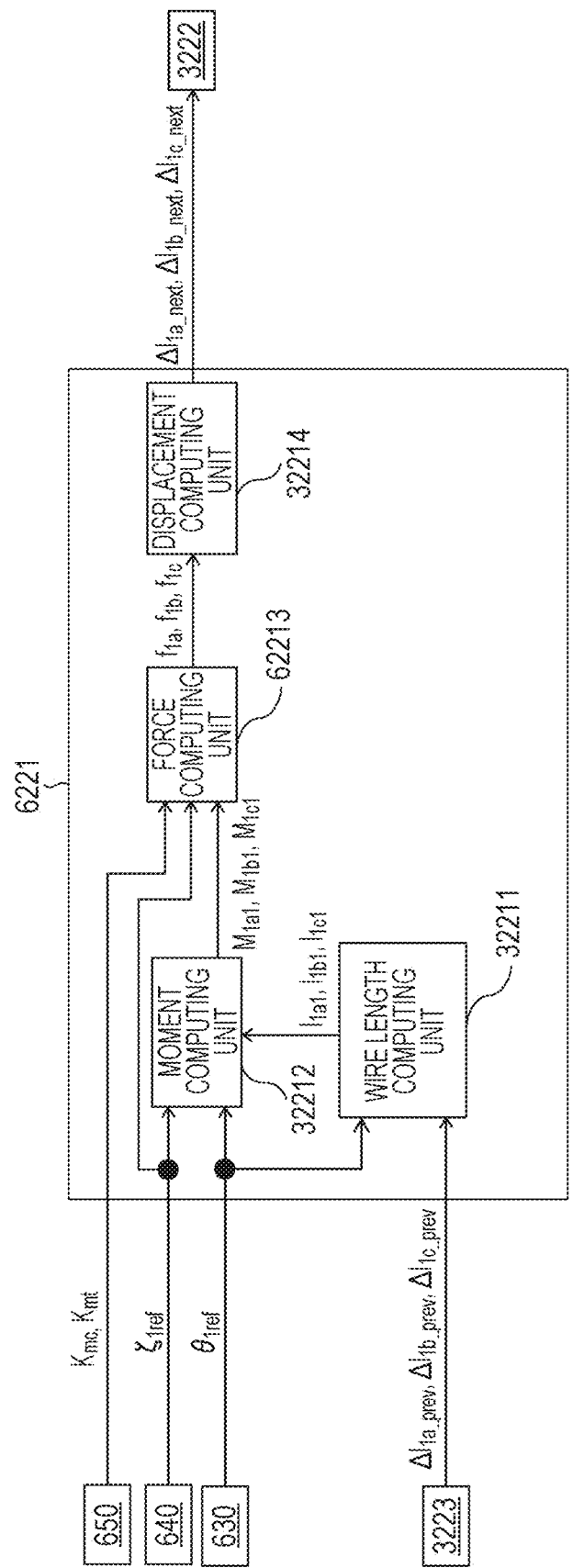

[Fig. 30]
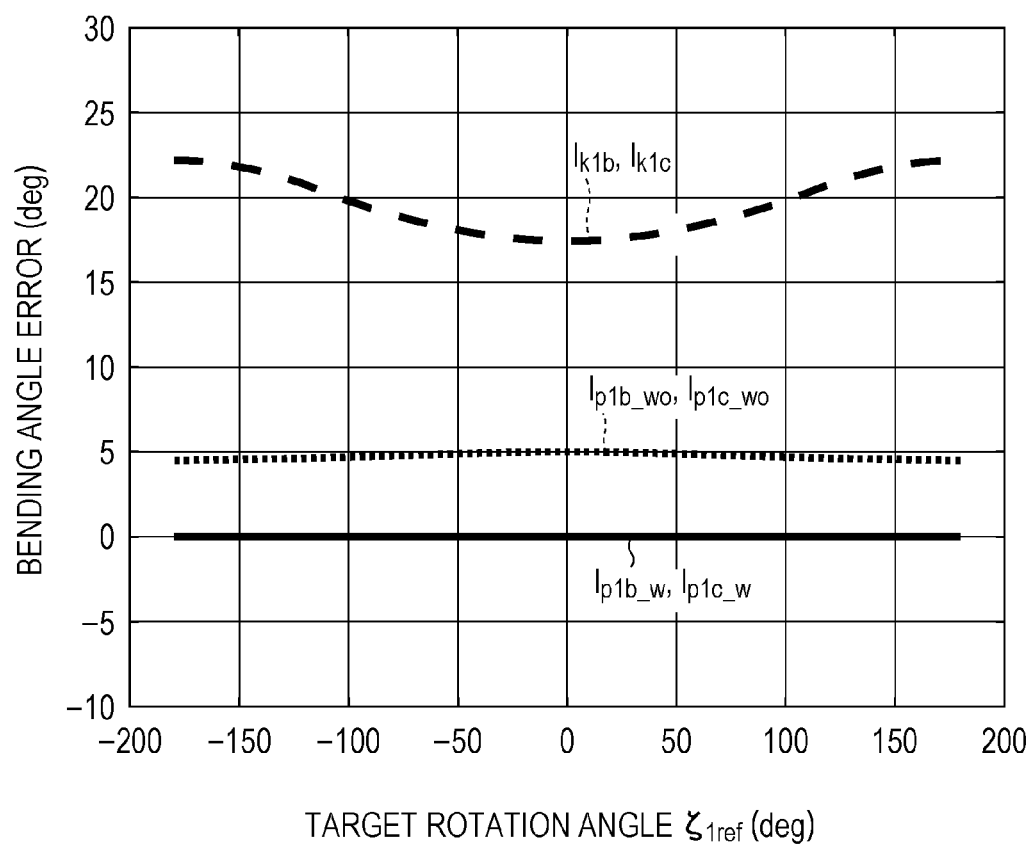

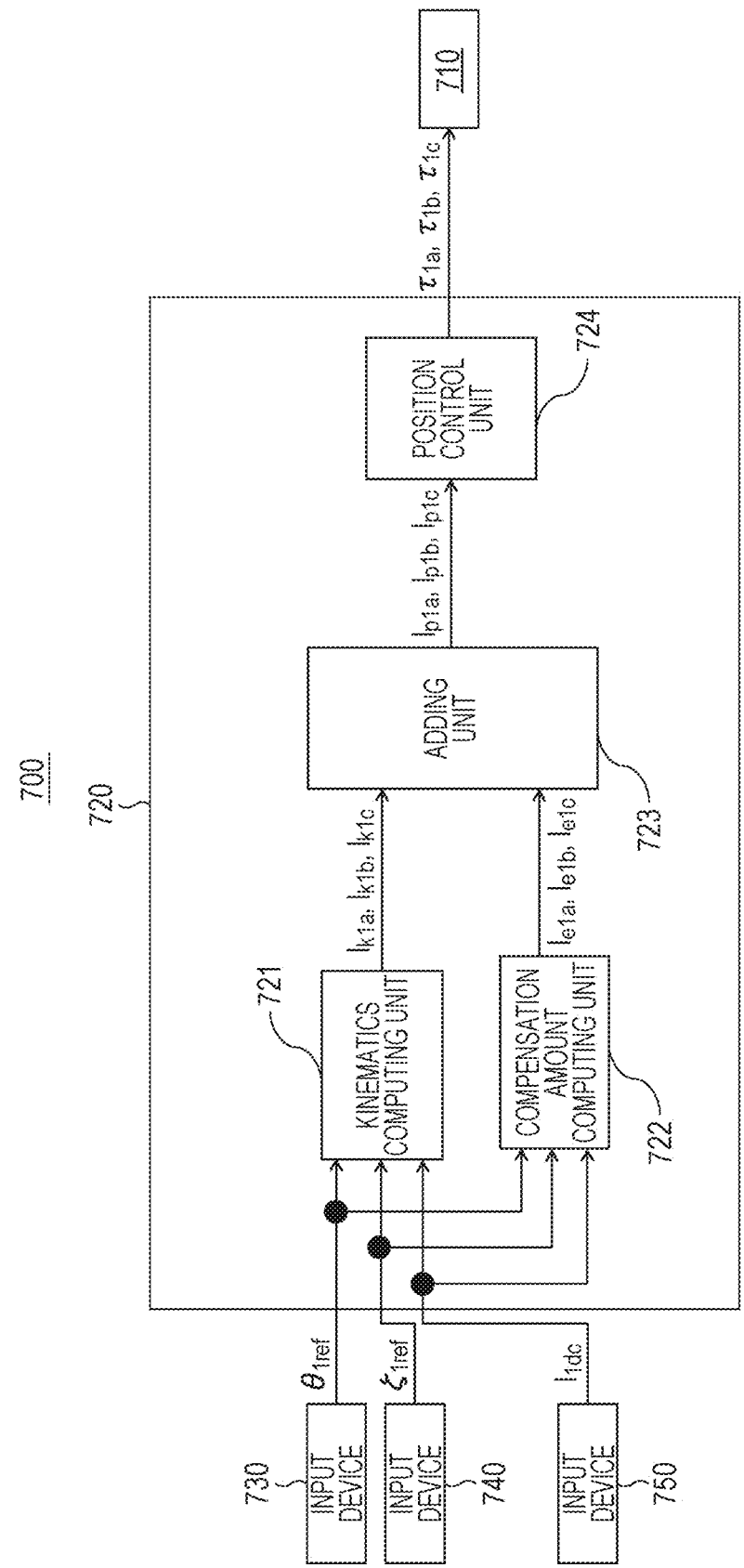
[Fig. 31]

[Fig. 32]
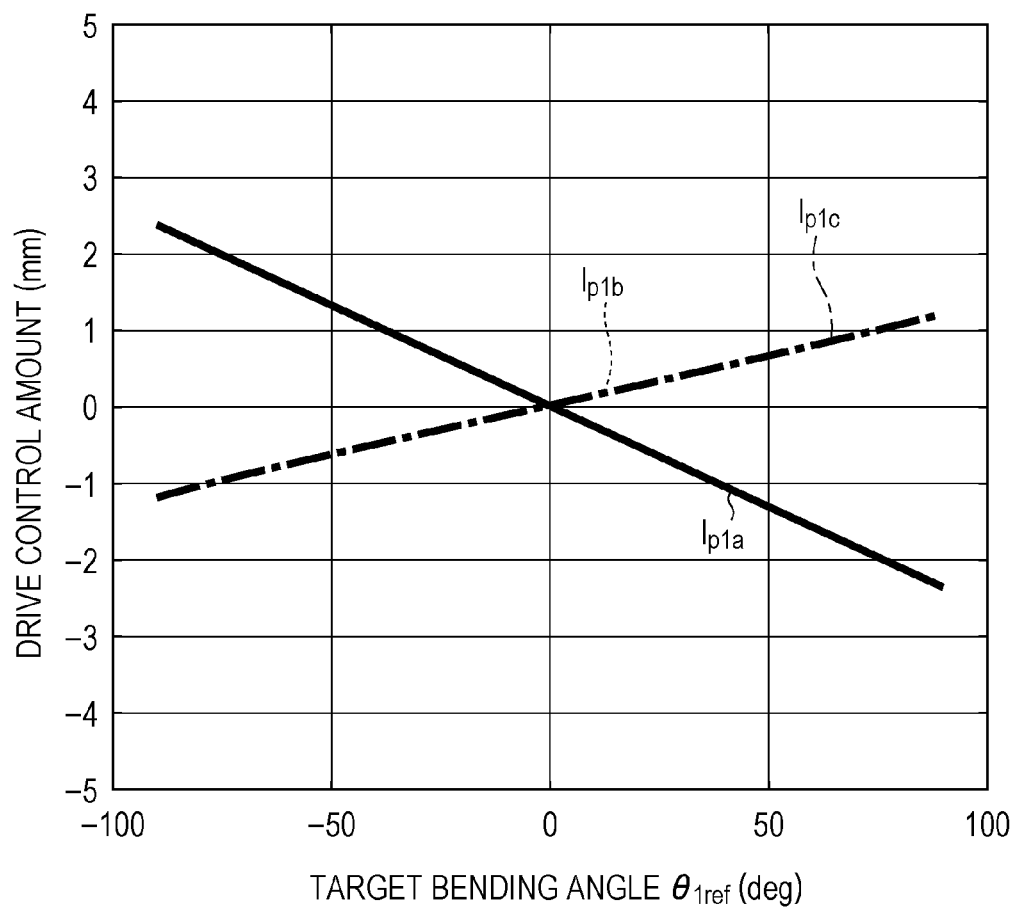

[Fig. 33]
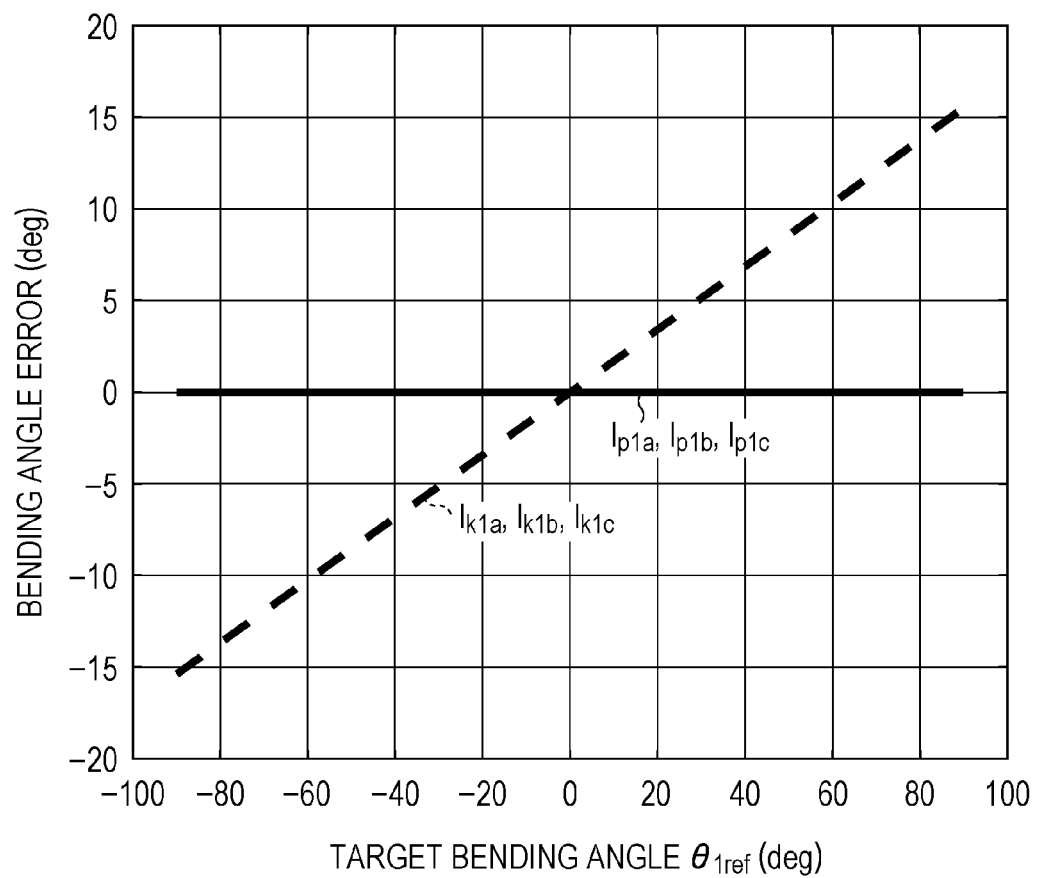

CONTINUUM ROBOT CONTROL DEVICE, CONTINUUM ROBOT CONTROL METHOD, AND PROGRAM

TECHNICAL FIELD

The present invention relates to a continuum robot control device and a continuum robot control method that controls operations of a continuum robot having bendable portions that can bend by wires being driven, and a program that causes a computer to function as the continuum robot control device.

BACKGROUND ART

In recent years, there is increased interest in minimally invasive medical care to reduce the load on the patient and improve the quality of life (QOL) following treatment or tests. A representative example of minimally invasive medical care is surgery/testing using endoscopes. For example, laparoscopic surgery leaves a smaller surgical wound as compared with conventional abdominal surgery, so not only can the necessary hospitalization period following surgery be shortened, but there is also an advantage of better aesthetics as well.

Flexible endoscopes are known as endoscopes used in minimally invasive medical care. These endoscopes have the portion that is inserted configured of a bendable member, so deep portions of the body can be reached without compressing tissue even in bended organs such as the esophagus, large intestine, and lungs. It is further anticipated that using actuators and the like to drive the insertion portion, and control the attitude thereof to follow paths in the body will be able to further reduce the load on the patient. Accordingly, research and development of continuum robot mechanisms usable as a flexible endoscope and control methods thereof are being actively pursued.

Such continuum robots may employ an arrangement where actuators are disposed on a base by using driving force transmission mechanism such as wires or the like, for example, thereby reducing the diameter of the bendable portion. For example, PTL 1 describes a method regarding a continuum robot using wires for a driving force transmission mechanism, where controlling the driving amount of the wires matches the attitude of a bendable portion to a target posture. To do so, the driving amount of the wires is computed using kinematics in PTL 1, assuming the wires to be rigid in the longitudinal direction.

In order to realize a continuum robot that can reach narrow spaces in deep parts of the body, such as the lungs, the wires serving as the driving transmission mechanism preferably are long and thin. However, such wires deform greatly under tensile force occurring at the time of pushing and pulling. Accordingly, there has been a problem that performing control input of driving amount of the wires computed using kinematics, such as the technology described in the specification of PTL 1, results in error occurring between the target posture of the bendable portion and the actual curvature, and the risk of contact between the wall of the body cavity and the bendable portion increases.

CITATION LIST

Patent Literature

PTL 1: U.S. Pat. No. 9,333,650

SUMMARY OF INVENTION

The present invention provides an arrangement that realizes reduced risk of contact between the wall of the body cavity (path within the body, etc.) and the bendable portion.

Solution to Problem

A continuum robot control device according to the present invention is a continuum robot control device configured to control operations of a continuum robot having a bendable portion that is bent by driving at least part of a plurality of wires. The continuum robot control device includes a first computing device configured to compute a driving amount of the at least part of the plurality of wires, based on a target bending angle that is a target value for a bending angle of the bendable portion, a second computing device configured to compute a compensation amount for compensation of the driving amount, based on the target bending angle, and a displacement of one of the plurality of wires at the target bending angle, and a setting device configured to set a driving control amount of performing driving control of the at least part of the plurality of wires, based on the driving amount calculated at the first computing device and the compensation amount calculated at the second computing device.

Further features of the present invention will become apparent from the following description of exemplary embodiments with reference to the attached drawings.

BRIEF DESCRIPTION OF DRAWINGS

FIG. 1 is a diagram illustrating an example of the external configuration of a continuum robot used in a first embodiment of the present invention.

FIG. 2 is a diagram illustrating an example of a schematic configuration of a bendable portion illustrated in FIG. 1, according to the first embodiment of the present invention.

FIG. 3 is a diagram illustrating an example of kinematic model of the bendable portion illustrated in FIG. 2, according to the first embodiment of the present invention.

FIG. 4 is a diagram illustrating an example of the functional configuration of a continuum robot control system according to the first embodiment of the present invention.

FIG. 5 is a characteristics diagram illustrating the relation between target bending angle and angle error according to the first embodiment of the present invention.

FIG. 6 is a characteristics diagram illustrating the relation between wire length and angle error according to the first embodiment of the present invention.

FIG. 7 is a diagram illustrating an example of a schematic configuration of a continuum robot used in a second embodiment of the present invention.

FIG. 8 is a diagram illustrating an example of a kinematics model at a first bendable portion and a second bendable portion illustrated in FIG. 7, according to the second embodiment of the present invention.

FIG. 9 is a diagram illustrating an example of the functional configuration of a continuum robot control system according to the second embodiment of the present invention.

FIG. 10 is a diagram illustrating an example of the functional configuration of a compensation amount computing unit illustrated in FIG. 9, according to the second embodiment of the present invention.

FIG. 11 is a diagram illustrating an example of the functional configuration of a displacement updating unit illustrated in FIG. 10, according to the second embodiment of the present invention.

FIG. 12 is a characteristics diagram illustrating the relation between iteration count, which is a count of iterative calculations performed, and displacement, according to the second embodiment of the present invention.

FIG. 13A is a characteristics diagram illustrating the relation between target bending angle and angle error at the first bendable portion and second bendable portion according to the second embodiment of the present invention.

FIG. 13B is a characteristics diagram illustrating the relation between target bending angle and angle error at the first bendable portion and second bendable portion according to the second embodiment of the present invention.

FIG. 14 is a diagram illustrating an example of a schematic configuration of a continuum robot used in a third embodiment of the present invention.

FIG. 15 is a diagram illustrating an example of kinematic model of the bendable portion illustrated in FIG. 14, according to the third embodiment of the present invention.

FIG. 16 is a diagram illustrating an example of the functional configuration of a continuum robot control system according to the third embodiment of the present invention.

FIG. 17 is a diagram illustrating an example of the functional configuration of a compensation amount computing unit illustrated in FIG. 16, according to the third embodiment of the present invention.

FIG. 18 is a diagram illustrating an example of the functional configuration of a displacement updating unit illustrated in FIG. 17, according to the third embodiment of the present invention.

FIG. 19 is a characteristics diagram illustrating the relation between target bending angle and bending angle error according to the third embodiment of the present invention.

FIG. 20 is a characteristics diagram illustrating the relation between target rotation angle and bending angle error according to the third embodiment of the present invention.

FIG. 21 is a diagram illustrating an example of a schematic configuration of a continuum robot used in a fourth embodiment of the present invention.

FIG. 22 is a diagram illustrating an example of the functional configuration of a continuum robot control system according to the fourth embodiment of the present invention.

FIG. 23 is a diagram illustrating an example of the external configuration of a continuum robot control system according to a fifth embodiment of the present invention.

FIG. 24 is a diagram illustrating an example of kinematic model of the bendable portion illustrated in FIG. 23, according to the fifth embodiment of the present invention.

FIG. 25 is a diagram illustrating an example of the functional configuration of a continuum robot control system according to the fifth embodiment of the present invention.

FIG. 26A is a diagram illustrating an example of the schematic configuration of a continuum robot control system used in a sixth embodiment of the present invention.

FIG. 26B is a diagram illustrating an example of the schematic configuration of a continuum robot control system used in the sixth embodiment of the present invention.

FIG. 27 is a diagram illustrating an example of the functional configuration of a continuum robot control system according to the sixth embodiment of the present invention.

FIG. 28 is a diagram illustrating an example of the functional configuration of a compensation amount computing unit illustrated in FIG. 27, according to the sixth embodiment of the present invention.

FIG. 29 is a diagram illustrating an example of the functional configuration of a displacement updating unit illustrated in FIG. 28, according to the sixth embodiment of the present invention.

FIG. 30 is a characteristics diagram illustrating the relation between target rotation angle and bending angle error according to the sixth embodiment of the present invention.

FIG. 31 is a diagram illustrating an example of the functional configuration of a continuum robot control system according to a seventh embodiment of the present invention.

FIG. 32 is a characteristics diagram illustrating the relation between target rotation angle and drive control amount, according to the seventh embodiment of the present invention.

FIG. 33 is a characteristics diagram illustrating the relation between target bending angle and bending angle error according to the seventh embodiment of the present invention.

DESCRIPTION OF EMBODIMENTS

Embodiments of the present invention will be described below with reference to the drawings. Specifically, the embodiments of the present invention which will be described below illustrate examples of a control system of a continuum robot (also referred to as a continuum manipulator) having been applied to a flexible endoscope. Note that the flexible endoscope applied as an example of the continuum robot control system according to the embodiments of the present invention is not restricted to the medical field, and is applicable to other fields as long as for observing within a path into which a bendable portion is inserted and removed from (e.g., an industrial endoscope for observing within piping or the like).

First Embodiment

First, a first embodiment of the present invention will be described.

(1-1. Modelling)

FIG. 1 is a diagram illustrating an example of the external configuration of a continuum robot 110 used in the first embodiment of the present invention. The continuum robot 110 illustrated in FIG. 1 has a wire 1a, a wire 1b, an elongated portion 111, a bendable portion 112, an actuator 113, and a fixing portion 114.

The elongated portion 111 is a component that passively bends under external force. The bendable portion 112 is a component that can be bent by driving part of the multiple wires 1a and 1b, i.e., the wire 1b (predetermined wire). The actuator 113 is a component that drives the wire 1b. The fixing portion 114 is a component that fixes the wire 1a.

In the following description the end portion of the components of the continuum robot 110 that is at the far side from a face of a base (e.g., from the face at the end of the elongated portion 111 on the side of the actuator 113 and fixing portion 114) will be referred to as "distal end", and the end portion at the side closer to the face of the aforementioned base will be referred to as "proximal end".

FIG. 2 is a diagram illustrating an example of a schematic configuration of the bendable portion 112 illustrated in FIG. 1, according to the first embodiment of the present invention. FIG. 2 also illustrates an example of a path into which the bendable portion 112 is inserted and removed from.

The bendable portion 112 has the multiple wires 1a and 1b extending through the face at the proximal end of the bendable portion 112, a first wire guide 1121 to which the multiple wires 1a and 1b are fixed at different positions, that guides the multiple wires 1a and 1b, second wire guides 1122 through 1125 that are disposed between the face at the proximal end described above and the first wire guide 1121, and that guide the multiple wires 1a and 1b. FIG. 2 also illustrates a distal end 1126 of the bendable portion 112, and a center position 1127 of the proximal end face of the bendable portion 112 described above. Specifically, the wire 1a and wire 1b are introduced into holes provided to the wire guides 1121 through 1125 and the elongated portion 111, with one end thereof being fixed to the first wire guide 1121, the other end of the wire 1a being connected to the fixing portion 114, and the other end of the wire 1b being connected to the actuator 113. When the actuator 113 illustrated in FIG. 1 is driven in the longitudinal direction of the bendable portion 112, the wire 1b is pushed and pulled, and the bendable portion 112 bends.

FIG. 3 is a diagram illustrating an example of a kinematic model in the bendable portion 112 illustrated in FIG. 2, according to the first embodiment of the present invention. In FIG. 3, the center position 1127 of the plane of the bendable portion 112 at the proximal end, illustrated in FIG. 2, is the origin. The longitudinal direction is represented by a $Z_1$ axis, the circumferential direction by an $X_1$ axis, and the direction from the plane of the drawing toward the far side by a $Y_1$ axis. In the same way, the center position of the plane of the bendable portion 112 at the distal end 1126, illustrated in FIG. 2, is the origin, the longitudinal direction is represented by a $Z_2$ axis, the circumferential direction by an $X_2$ axis, and the direction from the plane of the drawing toward the far side by a $Y_2$ axis. Further, the angle between the $Z_1$ axis and $Z_2$ axis is a bending angle $\theta_1$.

Description will be made below using symbols defined as follows. $\theta_1$ represents the absolute bending angle at the distal end of the bendable portion, $l_{1a1}$ and $l_{1b1}$ represent the length of the wire 1a and the length of the wire 1b of the bendable portion, $l_{p1b}$ represents the drive control amount of the wire 1b of the bendable portion, and $l_{e1b}$ represents the compensation amount of the wire 1b of the bendable portion. $\Delta l_{1a}$ and $\Delta l_{1b}$ represent the displacement of the wire 1a and the displacement of the wire 1b of the bendable portion, $f_{1a}$ and $f_{1b}$ represent the force acting on the distal end from the wire 1a and the force acting on the distal end from the wire 1b of the bendable portion, $M_{1a1}$ and $M_{1b1}$ represent the bending moment acting on the distal end from the wire 1a and the bending moment acting on the distal end from the wire 1b of the bendable portion, $R_g$ represents the diameter of a circle of which the radius is the distance from the center of the bendable portion to the wire 1a and wire 1b, $L_{10}$ is the total length of the wire 1a and wire 1b of the bendable portion, and $l_{10}$ represents the wire length of the bendable portion when the bending angle is 0 degrees. E represents the Young's modulus of the wires, A represents the cross-sectional area of the wires, and I represents the moment of inertia of area of the wires. Note that for the drive control amount $l_{p1b}$, the displacements $\Delta l_{1a}$ and $\Delta l_{1b}$, and forces $f_{1a}$ and $f_{1b}$, the distal end direction is the positive direction. The clockwise direction is the positive direction for moments $M_{1a1}$ and $M_{1b1}$. The same is true for the following embodiments as well.

A kinematic model and elastic wire driving model will be studied in the present embodiment under the following assumptions. Assumption 1 is that at the bendable portion, the wires deform uniformly over the curvature. Assumption 2 is that torsional deformation of the wires is not to be taken into consideration. Assumption 3 is that friction occurring between the wires and wire guides, and between the wires and the elongated portion, is not to be taken into consideration. Assumption 4 is that force and moment acting between the wire guides and wires is not to be taken into consideration. Assumption 5 is that of the forces acting between the wires and the distal end, only the component in the longitudinal direction of the wires is to be taken into consideration, and the component in the radial direction is not to be taken into consideration. Assumption 6 is that the displacement of the wires is proportionate to the tensile force acting on the wires. Assumption 7 is that the bending moment of the wires is proportionate to the deflection angle. Assumption 8 is that tensile rigidity and bending rigidity are equal among the wires. Assumption 9 is that Young's modulus, crosssectional area, and moment of inertia of area are equal among the wires.

First, a relational expression that represents a kinematic model will be derived, assuming that the wire 1a and wire 1b are rigid in the longitudinal direction. With the distance between the wire 1a and 1b represented by $R_g$ as illustrated in FIG. 3, the bending angle $\theta_1$ can be expressed by the following Expression (1), using the length $l_{1a1}$ of the wire 1a and length $l_{1b1}$ of the wire 1b at the bendable portion 112, based on the above Assumption 1 and Assumption 2.

$$R_g \theta_1 = l_{1b1} - l_{1a1} \tag{1}$$

Now, the right side of Expression (1) is equal to the driving amount of the wire 1b, so by computing using the kinematic model, the driving amount $l_{k1b}$ of the wire 1b can be expressed by the following Expression (2).

$$l_{k1b} = R_g \theta_1 \tag{2}$$

Next, a relational expression that represents an elastic wire driving model will be derived, taking into consideration displacement of the wires. The wire length $l_{1a1}$ and the wire length $l_{1b1}$ can be respectively expressed by the following Expressions (3) and (4), where $l_{10}$ represents the wire length of the bendable portion 112 when the bending angle $\theta_1$ is 0 degrees, $\Delta l_{1a}$ represents the displacement of the wire 1a, $\Delta l_{1b}$ represents the displacement of the wire 1b, and $l_{p1b}$ represents the drive control amount of the wire 1b that is calculated using an elastic wire driving model.

$$l_{1a1} = l_{10} + \Delta l_{1a} \tag{3}$$

$$l_{1b1} = l_{10} + \Delta l_{1b} + l_{p1b} \tag{4}$$

By substituting Expressions (2) through (4) in to Expression (1), the drive control amount $l_{p1b}$ of the wire 1b can be expressed as in the following Expression (5).

$$l_{p1b} = l_{k1b} + \Delta l_{1a} - \Delta l_{1b} \tag{5}$$

Thus, it can be seen from Expression (5) that the drive control amount $l_{p1b}$ of the wire 1b is the sum of the differential of displacement of wires 1a and 1b and the amount of drive $l_{k1b}$. Accordingly, error in the driving amount due to displacement of the wires can be compensated according to the following Expression (6) as compensation amount $l_{e1b}$.

$$l_{e1b} = \Delta l_{1a} - \Delta l_{1b} \tag{6}$$

Next, the displacement $\Delta l_{1a}$ of the wire 1a and the displacement $\Delta l_{1b}$ of the wire 1b are derived from an expression of balance of the force and moment acting on the distal end 1126 of the bendable portion 112 and the wires.

Longitudinal-direction force $f_{1a}$ and $f_{1b}$ from the wire $1a$ and wire $1b$, and bending moments $M_{1a1}$ and $M_{1b1}$ on the $Y_1$ axis, act on the distal end 1126 of the bendable portion 112, based on the above Assumptions 3, 4, and 5. Accordingly, the balance of force and moment at the distal end 1126 of the bendable portion 112 can be expressed by the following Expressions (7) and (8).

$$f_{1a} + f_{1b} = 0 \quad (7)$$

$$M_{1a1} + M_{1b1} - R_g f_{1a} = 0 \quad (8)$$

Also, forces $f_{1a}$ and $f_{1b}$, and moments $M_{1a1}$ and $M_{1b1}$ can be expressed by the following Expressions (9) and (10), from the above Assumptions 6, 7, and 8, using the displacements $\Delta l_{1a}$ and $\Delta l_{1b}$ and the bending angle $\theta_1$.

[Math. 1]

$$f_{1a} = -k_e \Delta l_{1a}, \quad f_{1b} = -k_e \Delta l_{1b} \quad (9)$$

$$M_{1a1} = -\frac{k_m}{l_{1a1}} \theta_1, \quad M_{1b1} = -\frac{k_m}{l_{1b1}} \theta_1 \quad (10)$$

In Expressions (9) and (10), the constants $k_e$ and $k_m$ respectively represent the tensile rigidity and bending rigidity of the wires. The constants $k_e$ and $k_m$ can be expressed by the following Expressions (11) and (12) using the total length of the wire (wire length) $L_0$, cross-sectional area A of the wires, moment of inertia of area I, and Young's modulus E, based on the above Assumption 9.

[Math. 2]

$$k_e = \frac{AE}{L_0} \quad (11)$$

$$k_m = EI \quad (12)$$

Also, the relation in the following Expression (13) can be established between the displacement $\Delta l_{1b}$ of the wire $1b$ and the displacement $\Delta l_{1a}$ of the wire $1a$, according to Expressions (7) and (9) in the present embodiment.

$$\Delta l_{1b} = -\Delta l_{1a} \quad (13)$$

Accordingly, the compensation amount $l_{e1b}$ of the wire $1b$ can be expressed by the following Expression (14), from Expressions (6) and (13).

$$l_{e1b} = 2\Delta l_{1a} \quad (14)$$

Substituting Expressions (9) and (10) into Expression (8), and further eliminating $l_{1b1}$, $\Delta l_{1b}$, and $l_{p1b}$ using Expressions (3), (4), (13), and (14), yields the polynomial for the displacement $\Delta l_{1a}$ of the wire $1a$, shown in the following Expression (15).

[Math. 3]

$$\frac{A_3(\theta_1)\Delta l_{1a}^3 + A_2(\theta_1)\Delta l_{1a}^2 + A_1(\theta_1)\Delta l_{1a} + A_0(\theta_1)}{\Delta l_{1a}^2 + B_1(\theta_1)\Delta l_{1a} + B_0(\theta_1)} = 0 \quad (15)$$

$A_3$ through $A_0$ and $B_1$ through $B_0$ in Expression (15) are coefficients for the displacement $\Delta l_{1a}$ of the wire $1a$ where the bending angle $\theta_1$ is a variable, and are each expressed in the following Expressions (16) and (17).

[Math.4]

$$A_3(\theta_1) = R_g k_e,$$

$$A_2(\theta_1) = R_g^2 k_e \theta_1 + 2 R_g k_e l_{10},$$

$$A_1(\theta_1) = \{(R_g^2 k_e l_{10} - 2 k_m)\theta_1 + R_g k_e l_{10}^2\},$$

$$A_0(\theta_1) = R_g k_m \theta_1^2 - 2 k_m l_{10} \theta_1 \quad (16)$$

$$B_1(\theta_1) = R_g \theta_1 + 2 l_{10},$$

$$B_0(\theta_1) = R_g l_{10}^2 \theta_1 + l_{10}^2 \quad (17)$$

The numerator in Expression (15) is a cubic polynomial regarding the displacement $\Delta l_{1a}$ of the wire $1a$, so solving this yields three different solutions. In the present embodiment, the solution out of these three solutions that has the smallest absolute value is the displacement $\Delta l_{1a}$ of the wire $1a$.

(1-2. Control System)

FIG. 4 is a diagram illustrating the functional configuration of a continuum robot control system 100 according to the first embodiment of the present invention. The continuum robot control system 100 illustrated in FIG. 4 is configured including a continuum robot 110 illustrated in FIG. 1, a continuum robot control device 120, and an input device 130.

The continuum robot control device 120 sets an drive control amount $l_{p1b}$ for driving control of the wire $1b$, based on a target bending angle $\theta_{1ref}$ that is a target value for the bending angle of the bendable portion 112, input from the input device 130, and outputs a drive command $T_{1b}$ based on the drive control amount $l_{p1b}$ to the continuum robot 110 (or more specifically, to the actuator 113).

The continuum robot control device 120 illustrated in FIG. 4 is configured including a kinematics computing unit 121, a compensation amount computing unit 122, an adding unit 123, and a position control unit 124.

The kinematics computing unit 121 is a first computing device that computes the driving amount $l_{k1b}$ of the wire $1b$, based on the target bending angle $\theta_{1ref}$ of the bendable portion 112 that is input from the input device 130, and the distance between the wire $1b$ (predetermined wire) and wire $1a$ (other wire). Specifically, the kinematics computing unit 121 substitutes the target bending angle $\theta_{1ref}$ into the bending angle $\theta_1$ in Expression (2) to calculate the driving amount $l_{k1b}$ of the wire $1b$.

The compensation amount computing unit 122 is a second computing device that computes the compensation amount $l_{e1b}$ of the wire $1b$, based on the target bending angle $\theta_{1ref}$ of the bendable portion 112 input from the input device 130, and the displacement $\Delta l_{1a}$ of the wire $1a$. Specifically, the compensation amount computing unit 122 calculates the displacement $\Delta l_{1a}$ of the wire $1a$ using Expression (15), and calculates the compensation amount $l_{e1b}$ of the wire $1b$ from the displacement $\Delta l_{1a}$ of the wire $1a$ using Expression (14).

The adding unit 123 adds the driving amount $l_{k1b}$ calculated by the kinematics computing unit 121 and the compensation amount $l_{e1b}$ calculated by the compensation amount computing unit 122 to calculate the drive control amount $l_{p1b}$ for driving control of the wire $1b$. That is to say, the adding unit 123 performs processing of compensating the driving amount $l_{k1b}$ calculated by the kinematics computing unit 121 by the compensation amount $l_{e1b}$ calculated by the compensation amount computing unit 122 to calculate the drive control amount $l_{p1b}$ of the wire 1b. The position control unit 124 outputs a drive command $\tau_{1b}$ based on the drive control amount $l_{p1b}$ to the continuum robot 110 (or more specifically, to the actuator 113). The adding unit 123 and position control unit 124 here make up a setting device that sets the drive control amount $l_{p1b}$ for driving control amount of the wire 1b in the present embodiment.

(1-3. Simulation)

Simulation is performed using the elastic wire driving model derived in the section 1-1 above, and the control system demonstrated in 1-2 above. The length $l_0$ of the bendable portion 112 is 0.01 m in the present embodiment. Angle error of the bendable portion 112 can be reduced in an arrangement where the total length (wire length) $L_0$ of the wire 1a and wire 1b is 1 m, and the control system according to the present embodiment is applied, which will be described below.

FIG. 5 is a characteristics diagram illustrating the relation between target bending angle and angle error according to the first embodiment of the present invention. The horizontal axis is the target bending angle (in degrees) in the characteristic diagram in FIG. 5, and the vertical axis is the angle error (in degrees).

Specifically, FIG. 5 illustrates angle error at the time of changing the target bending angle $\theta_{1ref}$ from −90 degrees to 90 degrees. The solid line in FIG. 5 illustrates angle error of response where the drive control amount $l_{p1b}$ of the wire 1b computed using the elastic wire driving model has been input, and the dashed line illustrates the angle error where the driving amount $l_{k1b}$ of the wire 1b computed using the kinematics model is input. According to the characteristics illustrated in FIG. 5, it can be seen that in a case where the drive control amount $l_{p1b}$ according to the present embodiment is used, the angle error is constantly 0 even if the target bending angle $\theta_{1ref}$ changes. On the other hand, it can be seen that the angle error increases or decreases if the target bending angle $\theta_{1ref}$ increases in a case of using the driving amount $l_{k1b}$ according to a comparative example. Thus, it can be seen that error in the attitude of the continuum robot 110 can be reduced by applying the control system according to the present embodiment, illustrated in FIG. 4.

Next, description will be made to demonstrate that the control system according to the present embodiment illustrated in FIG. 4 is particularly advantageous in attitude control of the continuum robot 110 that has wires of a length longer than the length of the bendable portion 112. FIG. 6 is a characteristics diagram illustrating the relationship between the wire length $L_0$ and angle error according to the first embodiment of the present invention. The horizontal axis in the characteristics diagram in FIG. 6 is the wire length $L_0$, and the vertical axis is angle error (in degrees).

Specifically, in the present embodiment where the length $l_0$ of the bendable portion 112 is 0.01 m, FIG. 6 illustrates the bending angle error in a case where driving amount $l_{k1b}$ is input to the continuum robot 110 where the target bending angle $\theta_{1ref}$ is 90 degrees and the wire length $L_0$ is 0.01 m to 1 m. It can be seen from the characteristics illustrated in FIG. 6 that great angle error occurs in a case where the wire length $L_0$ is 0.1 m or longer. Accordingly, the control system according to the present embodiment illustrated in FIG. 4 is particularly advantageous in the continuum robot 110 where the wire length $L_0$ is longer than the length $l_0$ of the bendable portion 112 by ten times or more.

The continuum robot control device 120 according to the first embodiment is configured to compute the compensation amount $l_{e1b}$ of the wire 1b at the compensation amount computing unit 122, based on the target bending angle $\theta_{1ref}$ of the bendable portion 112 input from the input device 130, and the displacement $\Delta l_{1a}$ of the wire 1a. The adding unit 123 and the position control unit 124 perform processing of compensating the driving amount $l_{k1b}$ calculated at the kinematics computing unit 121 by the compensation amount $l_{e1b}$ calculated by the compensation amount computing unit 122, thereby setting the drive control amount $l_{p1b}$ of the wire 1b.

According to this configuration, error in the driving amount $l_{k1b}$ due to wire deformation can be compensated. Thus, error between the target posture of the bendable portion 112 and the actual attitude can be reduced, and as a result, reduction in the risk of contact between a path in the body or the like and the bendable portion can be realized.

Although the compensation amount computing unit 122 derives the compensation amount $l_{ab}$ using the displacement $\Delta l_{1a}$ of the wire 1a (other wire) in the present embodiment, an arrangement may be made where the compensation amount $l_{e1b}$ is derived using the displacement $\Delta l_{ib}$ of the wire 1b (predetermined wire). Specifically, the following Expression (18) is derived where $\Delta l_{1a}$ in Expression (15) is replaced by $-\Delta l_{1b}$ using Expression (13), and $\Delta l_{1b}$ is calculated using Expression (18). Expression (19) where $\Delta l_{1a}$ in Expression (14) has been replaced by $-\Delta l_{1b}$ is then used to compute the compensation amount $l_{e1b}$.

[Math. 5]

$$-A_3(\theta_1)\Delta l_{1b}^3 + A_2(\theta_1)\Delta l_{1b}^2 - \frac{A_1(\theta_1)\Delta l_{1b} + A_0(\theta_1)}{\Delta l_{1b}^2 + B_1(\theta_1)\Delta l_{1b} + B_0(\theta_1)} = 0 \quad (18)$$

$$l_{e1b} = -2\Delta l_{1b} \quad (19)$$

Although only a method of computing compensation amount from the displacement of the other wire is illustrated in the following embodiments, the compensation amount can be computed using the displacement of the predetermined wire, in the same way as in the present embodiment.

Second Embodiment

Next, a second embodiment of the present invention will be described. The second embodiment is an arrangement of applying a continuum robot having multiple (specifically, two) bendable portions in the direction of inserting and removing to and from the path.

Expression (15) according to the first embodiment is a cubic polynomial regarding wire displacement, so an analytical solution can be easily found. However, the highest order of displacement in the polynomial corresponding to Expression (15) is the fifth order or higher for continuum robots having multiple bendable portions, so finding an analytical solution is difficult. Accordingly, the control system according to the second embodiment finds a numerical solution for displacement by iterative calculation. Accordingly, the control system according to the present invention can be applied to a continuum robot that has multiple bendable portions. In the iterative calculation, numerical values are sequentially substituted into multiple equations derived by the elastic wire driving model, and wire displacement is updated. Accordingly, iterative calculation can be performed by combining simple update rules even if the number of bendable portions increases.

In the following, first, a kinematics model and elastic wire driving model for a continuum robot will be derived. Thereafter, the control system according to the present embodiment where wire displacement is calculated using iterative calculation will be demonstrated, and the capability to improve control performance even in a continuum robot having multiple bendable portions will be described by way of numerical examples.

(2-1. Modelling)

FIG. 7 is a diagram illustrating an example of a schematic configuration of a continuum robot 210 used in the second embodiment of the present invention. Configurations that are the same as configurations illustrated in FIGS. 1 and 2 are denoted by the same symbols, and detailed description thereof will be omitted. A path into which bendable portions 112 and 212 are inserted and removed from is omitted from illustration in FIG. 7.

Specifically, the continuum robot 210 illustrated in FIG. 7 is configured having a first bendable portion 112 that is equivalent to the bendable portion 112 illustrated in FIG. 2, and a second bendable portion 212. That is to say, the continuum robot 210 illustrated in FIG. 7 has multiple bendable portions 112 and 212 serially arranged.

The second bendable portion 212 has multiple wires 2a and 2b extending through a face at the proximal end of the second bendable portion 212 (the face at the distal end 1126 of the first bendable portion 112), a first wire guide 2121 to which the multiple wires 2a and 2b are fixed at different positions, that guides the multiple wires 2a and 2b, and second wire guides 2122 through 2125 that are disposed between the face at the proximal end described above and the first wire guide 2121, and that guide the multiple wires 2a and 2b.

Holes are provided to the wire guides 1121 through 1125 of the first bendable portion 112 on the outer side of the guide holes for the wire 1a and wire 1b, for example, for guiding the wire 2a and wire 2b. The wires are guided through the elongated portion 111 in the same way as with the continuum robot 110 in the first embodiment, with the wire 1a and wire 2a being connected to a fixing portion 214, and the wire 1b and wire 2b being connected to an actuator 213. In the example illustrated in FIG. 7, the actuator 213 is a driving mechanism where the wire 1b and wire 2b can each be independently driven, and an arrangement may be made in the present embodiment where two actuators 213 are provided corresponding to the wire 1b and wire 2b. Accordingly, the first bendable portion 112 can be driven by driving the wire 1b and the second bendable portion 212 can be driven by driving the wire 2b in the present embodiment.

In the second embodiment described below, the following Assumptions 10 through 12 are added to the above-described Assumptions 1 through 9, and a kinematic model and elastic wire driving model in the continuum robot 210 according to the second embodiment are derived. Assumption 10 is that the distance between the guide hole for the wire 1a and the guide hole for the wire 2a is short, so the difference between each guide hole and the center axis of the bendable portion is $R_g/2$ for both. This is the same regarding the relation between the guide hole for the wire 1b and the guide hole for the wire 2b using the same method as with the first embodiment described above. Assumption 11 is that the length $l_{2a1}$ of the wire 2a and the length $l_{1a1}$ of the wire 1a are the same in the first bendable portion 112. This is the same regarding the length $l_{2b1}$ of the wire 2b and the length $l_{1b1}$ of the wire 1b as well. Assumption 12 is that only bending moment of the wires acts between the distal end 1126 of the first bendable portion 112 and the wire 2a and wire 2b, and that there is no friction or reactive force acting.

FIG. 8 is a diagram illustrating an example of a kinematic model at the first bendable portion 112 and second bendable portion 212 illustrated in FIG. 7, according to the second embodiment of the present invention. In FIG. 8, a center position of the plane at the distal end 2126 of the second bendable portion 212, illustrated in FIG. 7, is the origin. The normal direction on the plane at the distal end 2126 is represented by a $Z_3$ axis, the circumferential direction by an $X_3$ axis, and the direction from the plane of the drawing toward the far side by a $Y_3$ axis. The angle between the $Z_1$ axis and the $Z_3$ axis is an absolute bending angle $\theta_2$, and an angle between the $Z_2$ axis and the $Z_3$ axis is a relative bending angle tilde$\theta_2$, as illustrated in FIG. 8. This bending angle tilde$\theta_2$ is indicated by a tilde indicating a relative coordinate system, since the reference face of the second bendable portion 212 differs from the reference face of the first bendable portion 112. Note that the notation in the following Expressions have a tilde superscript over the symbol $\theta$ indicating a relative coordinate system, but this has been written out in the text of the present specification as bending angle "tilde$\theta_2$" or the like, which is true throughout the following description.

In the present embodiment, the relative bending angle tilde$\theta_2$ is expressed by the following Expression (20) using bending angles $\theta_1$ and $\theta_2$.

[Math.6]

$$\widetilde{\theta_2} = \theta_2 - \theta_1 \tag{20}$$

Also, the relative bending angle tilde$\theta_2$ is expressed by the following Expression (21) using the length $l_{2a2}$ of the wire 2a and the length $l_{2b2}$ of the wire 2b in the second bendable portion 212, in the same way as Expression (1) in the first embodiment.

[Math.7]

$$R_g \widetilde{\theta_2} = l_{2b2} - l_{2a2} \tag{21}$$

Accordingly, the driving amount $l_{k2b}$ of the second bendable portion 212 when assuming that the wires are rigid in the longitudinal direction can be expressed by the following Expression (22).

[Math.8]

$$l_{k2b} = R_g \widetilde{\theta_2} \tag{22}$$

Also, Expression (2) holds at the first bendable portion 112 of the continuum robot 210 according to the present embodiment, so the kinematic model can be expressed using Expressions (2) and (22).

Taking into consideration stretching and contraction of the wires, the length of the wire 2a and wire 2b at the first bendable portion 112 and second bendable portion 212 can be expressed by the following Expressions (23) and (24), using the displacement $\Delta l_{2a}$ of the wire 2a and the displacement $\Delta l_{2b}$ of the wire 2b, and the drive control amount $l_{p2b}$ of the wire 2b.

$$l_{2a1} + l_{2a2} = l_{20} + \Delta l_{2a} \tag{23}$$

$$l_{2b1} + l_{2b2} = l_{20} + \Delta l_{2b} + l_{p2b} \tag{24}$$

Now, the length $l_{1a1}$ and the length $l_{2a1}$, and the length $l_{1b1}$ and the length $l_{2b1}$, are equal, from the above-described Assumption 11, so substituting Expression (3) into Expression (23) and substituting Expression (4) into Expression

(24) enables the lengths $l_{2a2}$ and $l_{2b2}$ to be respectively expressed by the following Expressions (25) and (26).

$$l_{2a2} = l_{20} - l_{10} + \Delta l_{2a} - \Delta l_{1a} \tag{25}$$

$$l_{2b2} = l_{20} - l_{10} + \Delta l_{2b} - \Delta l_{1b} + l_{p2b} - l_{p1b} \tag{26}$$

Substituting Expressions (22), (25), and (26) into Expression (21), and further eliminating the drive control amount $l_{p1b}$ using Expression (5) yields the following Expression (27).

$$l_{p2b} = l_{k2b} + l_{k1b} + (\Delta l_{2a} - \Delta l_{2b}) \tag{27}$$

Accordingly, obtaining the compensation amount $l_{e2b}$ of the wire 2b at the second bendable portion 212 by the following Expression (28) in the same way as in Expression (6) in the first embodiment enables the error in the driving amount due to stretching and contraction of the wires at the second bendable portion 212 to be compensated.

$$l_{e2b} = \Delta l_{2a} - \Delta l_{2b} \tag{28}$$

Note that as described above, the kinematics of the first bendable portion 112 in the second embodiment are the same as in the first embodiment described above, so the drive control amount $l_{p1b}$ and compensation amount $l_{e1b}$ of the wire 1b are expressed by Expressions (5) and (6) in the same way as in the first embodiment, respectively.

An expression of balance of the force and moment acting on the distal end 112b of the first bendable portion 112 and the distal end 212b of the second bendable portion 212 is derived, to obtain the wire displacement. The balance of moment on the $Y_3$ axis that acts on the distal end 212b of the second bendable portion 212 is expressed by the following Expression (29), in the same way as in Expression (8) in the first embodiment.

$$M_{2a2} + M_{2b2} - R_g f_{2a} = 0 \tag{29}$$

Balance in the $Z_3$ axial direction is expressed by the following Expression (30).

$$f_{2a} - f_{2b} = 0$$

Also, moments $M_{2a2}$ and $M_{2b2}$, and forces $f_{2a}$ and $f_{2b}$, can be expressed by the following Expressions (31) and (32), in the same way as in Expressions (10) and (9), respectively.

[Math. 9]

$$M_{2a2} = -\frac{k_m}{l_{2a2}} \widetilde{\theta_2}, \tag{31}$$

$$M_{2b2} = -\frac{k_m}{l_{2b2}} \widetilde{\theta_2}$$

$$f_{2a} = -k_e \Delta l_{2a}, \tag{32}$$

$$f_{2b} = -k_e \Delta l_{2b}$$

The following Expression (33) then holds, from Expressions (30) and (32).

$$\Delta l_{2b} = -\Delta l_{2a} \tag{33}$$

Accordingly, substituting Expression (33) into Expression (28) yields the following Expression (34).

$$l_{e2b} = 2\Delta l_{2a} \tag{34}$$

It can thus be seen from Expressions (14) and (34) that once the displacement $\Delta l_{1a}$ of the wire 1a and the displacement $\Delta l_{2a}$ of the wire 2a have been found, the compensation amount $l_{e1b}$ of the wire 1a and the compensation amount $l_{e2b}$ of the wire 2a can be computed. In addition to the bending moment of the wire 1a, wire 1b, wire 2a, and wire 2b at the first bendable portion 112, anti-moment of moments $M_{2a2}$ and $M_{2b2}$ act on the distal end 112b of the bendable portion 112, based on the above-described Assumption 12. Accordingly, the balance of moment on the $Y_2$ axis at the distal end 112b of the first bendable portion 112 can be expressed by the following Expression (35).

$$(M_{1a1} + M_{1b1} + M_{2a1} + M_{2b1}) - (M_{2a2} + M_{2b2}) - R_g f_{1a} = 0 \tag{35}$$

From the above-described Assumption 11, the wire length $l_{1a1}$ and the wire length $l_{2a1}$ are the same, and the wire length $l_{1b1}$ and the wire length $l_{2b1}$ are the same. Accordingly, moment $M_{2a1}$ and moment $M_{1a1}$ are equal, moment $M_{2b1}$ and moment $M_{1b1}$ are equal, and the following Expression (36) holds.

$$M_{1a1} = M_{2a1}, M_{1b1} = M_{2b1} \tag{36}$$

Accordingly, Expression (35) can be modified to the following Expression (37).

$$2(M_{1a1} + M_{1b1}) - (M_{2a2} + M_{2b2}) - R_g f_{1a} = 0 \tag{37}$$

Only tension of the wire 1a and wire 1b act on the $Z_2$ axial direction of the distal end 112b of the first bendable portion 112, from the above-described Assumption 12, so the Expression of balance of force for the first bendable portion 112 is expressed by Expression (7), in the same way as in the first embodiment.

(2-2. Control System)

Performing modification of Expressions the same as with the first embodiment on the elastic wire driving model according to the second embodiment enables two in-dependent polynomials to be obtained, where the displacement $\Delta l_{1a}$ of the wire 1a and the displacement $\Delta l_{2a}$ of the wire 2a are variables. However, these are high-order polynomials of five or more orders regarding the displacement $\Delta l_{1a}$ and $\Delta l_{2a}$, so finding an analytical solution is difficult. At this time, a numerical solution can be obtained by an optimization method such as the gradient method or the like, but deriving a high-order polynomial regarding the continuum robot 210 having a great number of bendable portions is not easy. Accordingly, in the second embodiment, numerical solutions are found for the displacement $\Delta l_{1a}$ of the wire 1a and the displacement $\Delta l_{2a}$ of the wire 2a by iterative calculation where simple expressions derived from the elastic wire driving model are combined.

FIG. 9 is a diagram illustrating an example of the functional configuration of a continuum robot control system 200 according to the second embodiment of the present invention. The continuum robot control system 200 illustrated in FIG. 9 is configured including the continuum robot 210 illustrated in FIG. 7, a continuum robot control device 220, and an input device 230.

In the second embodiment, the input device 230 inputs, in addition to the target bending angle $\theta_{1ref}$ of the first bendable portion 112, a target bending angle (reference relative bending angle tilde$\theta_{2ref}$), to the continuum robot control device 220.

The continuum robot control device 220 sets drive control amount $l_{p1b}$ for driving control of the wire 1b, and an drive control amount $l_{p2b}$ for driving control of the wire 2b, based on a target bending angle $\theta_{1ref}$ for the first bendable portion 112 and a target bending angle tilde$\theta_{2ref}$ for the second bendable portion 212, input from the input device 230, and outputs a drive command $T_{1b}$ based on the drive control amount $l_{p1b}$ and a drive command $T_{2b}$ based on the drive control amount $l_{p2b}$, to the continuum robot 210 (or more specifically, to the actuator 213).

The continuum robot control device 220 illustrated in FIG. 9 is configured including a kinematics computing unit 221, a compensation amount computing unit 222, an adding unit 223, and a position control unit 224.

The kinematics computing unit 221 computes the driving amount $l_{k1b}$ of the wire 1b, based on the target bending angle $\theta_{1ref}$ of the first bendable portion 112 input from the input device 230 and the distance between the wire 1b (predetermined wire) and wire 1a (other wire), and also computes the driving amount $l_{k2b}$ of the wire 2b, based on the target bending angle $\tilde{\theta}_{2ref}$ of the second bendable portion 212 input from the input device 230 and the distance between the wire 2b (predetermined wire) and wire 2a (other wire). Specifically, the kinematics computing unit 221 substitutes the target bending angle $\theta_{1ref}$ into the bending angle $\theta_1$ in Expression (2) to calculate the driving amount $l_{k1b}$ of the wire 1b, and also substitutes the target bending angle $\tilde{\theta}_{2ref}$ into the bending angle $\tilde{\theta}_2$ in Expression (22) to calculate the driving amount $l_{k2b}$ of the wire 2b.

The compensation amount computing unit 222 is a second computing device that computes the compensation amount $l_{e1b}$ of the wire 1b, based on the target bending angle $\theta_{1ref}$ of the first bendable portion 112 input from the input device 230, and the displacement $\Delta l_{1a}$ of the wire 1a, and that computes the compensation amount $l_{e2b}$ of the wire 2b, based on the target bending angle $\tilde{\theta}_{2ref}$ of the second bendable portion 212 input from the input device 230, and the displacement $\Delta l_{2a}$ of the wire 2a. Specifically, the compensation amount computing unit 222 calculates the displacement $\Delta l_{1a}$ of the wire 1a using Expression (15), and calculates the compensation amount $l_{e1b}$ of the wire 1b from the displacement $\Delta l_{1a}$ of the wire 1a using Expression (14). The compensation amount computing unit 222 also calculates the displacement $\Delta l_{2a}$ of the wire 2a in the same way, and calculates the compensation amount $l_{e2b}$ of the wire 2b from the displacement $\Delta l_{2a}$ of the wire 2a using Expression (34).

The adding unit 223 adds the driving amount $l_{k1b}$ calculated by the kinematics computing unit 221 and the compensation amount $l_{e1b}$ calculated by the compensation amount computing unit 222 to calculate the drive control amount $l_{p1b}$ for driving control of the wire 1b. The adding unit 223 also adds the driving amount $l_{k2b}$ calculated by the kinematics computing unit 221 and the compensation amount $l_{e2b}$ calculated by the compensation amount computing unit 222 to calculate the drive control amount $l_{p2b}$ for driving control of the wire 2b. That is to say, the adding unit 223 performs processing of compensating the driving amount $l_{k1b}$ and $l_{k2b}$ calculated by the kinematics computing unit 221, respectively by the compensation amounts $l_{e1b}$ and $l_{e2b}$ calculated by the compensation amount computing unit 222 to calculate the drive control amount $l_{p1b}$ of the wire 1b and the drive control amount $l_{p2b}$ of the wire 2b. The position control unit 224 outputs a drive command $T_{1b}$ based on the drive control amount $l_{p1b}$ and a drive command $T_{2b}$ based on the drive control amount $l_{p2b}$ to the continuum robot 210 (or more specifically, to the actuator 213). In the present embodiment, the adding unit 223 and position control unit 224 make up a setting device that sets the drive control amount $l_{p1b}$ for driving control of the wire 1b and the drive control amount $l_{p2b}$ for driving control of the wire 2b.

FIG. 10 is a diagram illustrating an example of the functional configuration of the compensation amount computing unit 222 illustrated in FIG. 9, according to the second embodiment of the present invention. The compensation amount computing unit 222 is configured including a displacement updating unit 2221, a convergence determining unit 2222, an output switching unit 2223, and an amplifying unit 2224, as illustrated in FIG. 10.

In accordance with input of the target bending angles $\theta_{1ref}$ and $\tilde{\theta}_{2ref}$, and first displacement candidate values $\Delta l_{1a\_prev}$ and $\Delta l_{2a\_prev}$ for the displacements of the wires 1a and 2b the displacement updating unit 2221 updates to second displacement candidate values $\Delta l_{1a\_next}$ and $\Delta l_{2a\_next}$. At this time, the displacement updating unit 2221 updates the second displacement candidate values $\Delta l_{1a\_next}$ and $\Delta l_{2a\_next}$ of the displacement of the wires 1a and 2b using the elastic wire driving model described above.

The convergence determining unit 2222 determines whether or not the second displacement candidate values $\Delta l_{1a\_next}$ and $\Delta l_{2a\_next}$ have converged at a constant value. In a case of having determined that the second displacement candidate values $\Delta l_{1a\_next}$ and $\Delta l_{2a\_next}$ have converged at a constant value, the convergence determining unit 2222 causes the output switching unit 2223 to output the second displacement candidate values $\Delta l_{1a\_next}$ and $\Delta l_{2a\_next}$ respectively as displacement $\Delta l_{1a}$ and displacement $\Delta l_{2a}$ to the amplifying unit 2224. In a case of having determined that the second displacement candidate values $\Delta l_{1a\_next}$ and $\Delta l_{2a\_next}$ have not converged at a constant value, the convergence determining unit 2222 causes the output switching unit 2223 to output the second displacement candidate values $\Delta l_{1a\_next}$ and $\Delta l_{2a\_next}$ as first displacement candidate values $\Delta l_{1a\_prev}$ and $\Delta l_{2a\_prev}$ to the displacement updating unit 2221, and iterative calculation is performed again. The convergence determining unit 2222 and output switching unit 2223 according to the present embodiment make up a configuration corresponding to an output processing unit according to the present invention.

The amplifying unit 2224 is a compensation amount calculating unit that uses the second displacement candidate values $\Delta l_{1a\_next}$ and $\Delta l_{2a\_next}$ as displacement $\Delta l_{1a}$ and displacement $\Delta l_{2a}$ respectively, to calculate the compensation amounts $l_{e1b}$ and $l_{e2b}$. The compensation amounts $l_{e1b}$ and $l_{e2b}$ are each double the displacement $\Delta l_{1a}$ and displacement $\Delta l_{1b}$ respectively in the present embodiment, as illustrated in in Expressions (14) and (34). Accordingly, the amplifying unit 2224 multiples the displacement $\Delta l_{1a}$ by 2 with regard to the first bendable portion 112 and calculates the compensation amount $l_{e1b}$, and multiples the displacement $\Delta l_{2a}$ by 2 with regard to the second bendable portion 212 and calculates the compensation amount $l_{e2b}$.

Note that an arrangement may be made where, in a case that the second displacement candidate values $\Delta l_{1a\_next}$ and $\Delta l_{2a\_next}$ do not converge at a constant value within a predetermined iteration count, the convergence determining unit 2222 causes the output switching unit 2223 to output the last second displacement candidate values $\Delta l_{1a\_next}$ and $\Delta l_{2a\_next}$ to have converged, respectively as displacement $\Delta l_{1a}$ and displacement $\Delta l_{2a}$ to the amplifying unit 2224. This can prevent the compensation amounts calculated at the amplifying unit 2224 from changing discontinuously. Although the initial values of the first displacement candidate values $\Delta l_{1a\_prev}$ and $\Delta l_{2a\_prev}$ in the iterative calculation in the present embodiment are 0, the displacements that converged last may be used as the initial values.

FIG. 11 is a diagram illustrating an example of the functional configuration of the displacement updating unit 2221 illustrated in FIG. 10 according to the second embodiment of the present invention. The displacement updating unit 2221 is configured including a wire length computing unit 22211, a moment computing unit 22212, a force computing unit 22213, and a displacement computing unit 22214, as illustrated in FIG. 11.

The wire length computing unit 22211 calculates the wire lengths $l_{1a1}$, $l_{1b1}$, $l_{2a2}$, and $l_{2b2}$, for each of the multiple wires 1a and 1b and wires 2a and 2b at the first bendable portion 112 and second bendable portion 212, in accordance with the input of the target bending angles $\theta_{1ref}$ and $\tilde{\theta}_{2ref}$ and first displacement candidate values $\Delta l_{1a\_prev}$ and $\Delta l_{2a\_prev}$. Specifically, the wire length computing unit 22211 calculates the wire lengths $l_{1a1}$, $l_{1b1}$, $l_{2a2}$, and $l_{2b2}$, using the following Expressions (38) through (41), where Expressions (1) through (5) and Expressions (21) through (27) have been modified.

[Math.10]

$$l_{1a1} = l_{10} + \Delta l_{1a\_prev} \tag{38}$$

$$l_{1b1} = l_{10} + \Delta l_{1a\_prev} + R_g \theta_{1ref} \tag{39}$$

$$l_{2a2} = l_{20} - l_{10} + \Delta l_{2a\_prev} - \Delta l_{1a\_prev} \tag{40}$$

$$l_{2b2} = l_{20} - l_{10} + \Delta l_{2a\_prev} - \Delta l_{1a\_prev} + R_g \tilde{\theta}_{2ref} \tag{41}$$

The moment computing unit 22212 calculates bending moments $M_{1a1}$, $M_{1b1}$, $M_{2a2}$, and $M_{2b2}$, for each of the multiple wires 1a and 1b and wires 2a and 2b, in accordance with input of the target bending angles $\theta_{1ref}$ and $\tilde{\theta}_{2ref}$ and the wire lengths $l_{1a1}$, $l_{1b1}$, $l_{2a2}$, and $l_{2b2}$. Specifically, the moment computing unit 22212 calculates the bending moments $M_{1a1}$, $M_{1b1}$, $M_{2a2}$, and $M_{2b2}$ using Expressions (10) and (36).

The force computing unit 22213 calculates forces $f_{1a}$ and $f_{2a}$ representing the tensile force on the wires 1a and 2a (other wires), in accordance with the input of the bending moments $M_{1a1}$, $M_{1b1}$, $M_{2a2}$, and $M_{2b2}$ of the multiple wires 1a and 1b and wires 2a and 2b. Specifically, the force computing unit 22213 calculates the forces $f_{1a}$ and $f_{2a}$ using Expressions (29) and (37).

The displacement computing unit 22214 computes the second displacement candidate values $\Delta l_{1a\_next}$ and $\Delta l_{2a\_next}$ in accordance with input of the forces $f_{1a}$ and $f_{2a}$, and updates displacement candidate values. Specifically, the displacement computing unit 22214 uses Expressions (9) and (32) to compute the second displacement candidate values $\Delta l_{1a\_next}$ and $\Delta l_{2a\_next}$, and updates the displacement candidate values. Accordingly, the second displacement candidate values $\Delta l_{1a\_next}$ and $\Delta l_{2a\_next}$ after updating in the present embodiment are represented by the following Expressions (42) and (43), respectively.

[Math. 11]

$$\Delta l_{1a\_next} = -\frac{k_m}{R_g k_e} \left\{ 2\left( \frac{1}{l_{10} + \Delta l_{1a\_prev} + R_g \theta_{1ref}} + \frac{1}{l_{10} + \Delta l_{1a\_prev}} \right) \theta_{1ref} + \left( \frac{1}{l_{20} - l_{10} + \Delta l_{2a\_prev} - \Delta l_{1a\_prev} + R_g \tilde{\theta}_{2ref}} + \frac{1}{l_{20} - l_{10} + \Delta l_{2a\_prev} - \Delta l_{1a\_prev}} \right) \tilde{\theta}_{2ref} \right\} \tag{42}$$

$$\Delta l_{2a\_next} = \frac{k_m}{R_g k_e} \left( \frac{1}{l_{20} - l_{10} + \Delta l_{2a\_prev} - \Delta l_{1a\_prev} + R_g \tilde{\theta}_{2ref}} + \frac{1}{l_{20} - l_{10} + \Delta l_{2a\_prev} - \Delta l_{1a\_prev}} \right) \tilde{\theta}_{2ref} \tag{43}$$

Note that Expressions (42) and (43) are illustrated to describe update rules, and that the displacement updating unit 2221 updates the displacement by sequentially substituting numerical values into multiple equations derived from the elastic wire driving model, as described above. Although the control system illustrated in FIGS. 9 through 11 according to the present embodiment perform convergence determination in iterative calculations using displacement, but wire length, force, and bending moment are also updated with each iterative calculation, so one of these may be used for determination of convergence.

Also, while the relative bending angle $\tilde{\theta}_{2ref}$ is used in the present embodiment as the target bending angle of the second bendable portion 212, the absolute bending angle may be used as the target bending angle, since the absolute angle and relative angle are mutually convertible, as illustrated in Expression (20).

(2-3. Simulation)

The control system according to the second embodiment, illustrated in FIGS. 9 through 11, is applied to the continuum robot 210 having the two bendable portions 112 and 212. Note that the lengths of the first bendable portion 112 and the second bendable portion 212 are 0.01 m, and the length of the elongated portion 111 is 1 m.

FIG. 12 is a characteristics diagram illustrating the relation between iteration count, which is a count of iterative calculations performed, and displacement, according to the second embodiment of the present invention. The horizontal axis in the characteristics diagram of FIG. 12 is the iteration count, and the vertical axis is the displacement in each iterative calculation performed.

Specifically, FIG. 12 shows the response of displacements $\Delta l_{1a}$ and $\Delta l_{2a}$ at the compensation amount computing unit 222 in a case where the target bending angle $\theta_{1ref}$ is −90 degrees and the target bending angle $\tilde{\theta}_{2ref}$ is 90 degrees, and the initial values of the displacements $\Delta l_{1a}$ and $\Delta l_{2a}$ are 0. Also, the solid line in FIG. 12 represents the displacement $\Delta l_{1a}$, and the dashed line represents the displacement $\Delta l_{2a}$. It can be seen from FIG. 12 that the displacements $\Delta l_{1a}$ and $\Delta l_{2a}$ converge by iterative calculations, since they both become constant after the fourth calculation having been performed.

FIGS. 13A and 13B are characteristics diagrams illustrating the relation between target bending angle and angle error at the first bendable portion 112 and second bendable portion 212 according to the second embodiment of the present invention.

Specifically, FIG. 13A illustrates the angle error of the first bendable portion 112 in a case where the target bending angle $\theta_{1ref}$ is set to −90 degrees, and the target bending angle $\tilde{\theta}_{2ref}$ is changed from −90 degrees to 90 degrees. Also, FIG. 13B illustrates the angle error of the second bendable portion 212 in a case where the target bending angle $\theta_{1ref}$ is set to −90 degrees, and the target bending angle $\tilde{\theta}_{2ref}$ is changed from −90 degrees to 90 degrees. The horizontal axis is the target bending angle $\tilde{\theta}_{2ref}$ in the characteristics diagrams of FIGS. 13A and 13B, while the vertical axis is angle error $\theta_1$ in FIG. 13A and is angle error $\tilde{\theta}_2$ in FIG. 13B.

The dotted lines in FIGS. 13A and 13B respectively represent response as to input of the driving amounts $l_{k1b}$ and $l_{k2b}$ computed by the kinematics computing unit 221. The solid lines in FIGS. 13A and 13B respectively represent response as to input of the drive control amounts $l_{p1b}$ and $l_{p2b}$ computed from the elastic wire driving model according to the second embodiment.

It can be seen from FIGS. 13A and 13B that in a case of using the driving amounts $l_{k1b}$ and $l_{k2b}$ according to a comparative example, the angle error of the first bendable portion 112 and the second bendable portion 212 both increase along with increase or decrease of the target bending angle tilde$\theta_{2ref}$. On the other hand, in a case of using the drive control amounts $l_{p1b}$ and $l_{p2b}$ according to the present embodiment, the angle error of the first bendable portion 112 and the second bendable portion 212 is constantly 0 even if the target bending angle tilde$\theta_{2ref}$ changes. Accordingly, it can be understood that applying the control system illustrated in FIGS. 9 through 11 according to the present embodiment enables attitude error of the continuum robot 210 that has multiple bendable portions to be reduced.

In the continuum robot control device 220 according to the second embodiment, the compensation amount computing unit 222 computes the respective compensation amounts $l_{e1b}$ and $l_{e2b}$ for the wires 1b and 2b, based on the target bending angles $\theta_{1ref}$ and tilde$\theta_{2ref}$ that have been input from the input device 230, and the displacements $\Delta l_{1a}$ and $\Delta l_{2a}$ of the wires 1a and 2a, for each bendable portion of the multiple bendable portions 112 and 212. The adding unit 223 and position control unit 224 perform processing to compensate the respective driving amounts $l_{k1b}$ and $l_{k2b}$ calculated at the kinematics computing unit 221 by the compensation amounts $l_{e1b}$ and $l_{e2b}$ calculated at the compensation amount computing unit 222, thereby setting the drive control amounts $l_{p1b}$ and $l_{p2b}$ of the wires 1b and 2b.

According to this configuration, error in the driving amounts $l_{k1b}$ and $l_{k2b}$ due to wire deformation can be compensated for in the continuum robot 210 having multiple bendable portions, as well. Accordingly, error between the reference position of the multiple bendable portions and the actual attitude can be reduced, and as a result, reduction in the risk of contact between a path in the body or the like and the bendable portion can be realized.

Note that the driving amount of each wire can be compensated for in the present embodiment using the compensation amount calculated based on the displacement of any one wire of the multiple wires relating to the same bendable portion, in the same way as in the first embodiment.

Third Embodiment

Next, a third embodiment of the present invention will be described. The third embodiment is an arrangement of applying a continuum robot having a bendable portion that is bendable three-dimensionally. Specifically, in the continuum robot according to the third embodiment, one bendable portion is bent by controlling driving of two wires, and the control system computes compensation amounts taking into consideration the displacement of these two wires, by iterative calculation similar to that in the second embodiment. Accordingly, the control capabilities of the continuum robot having a bendable portion that is bendable three-dimensionally can be improved.

(3-1. Modelling)

FIG. 14 is a diagram illustrating an example of a schematic configuration of a continuum robot 310 used in the third embodiment of the present invention. Configurations that are the same as configurations illustrated in FIGS. 1, 2, and 7 are denoted by the same symbols in FIG. 14, and detailed description thereof will be omitted. FIG. 14 also illustrates an example of a path into which a bendable portions 312 is inserted and removed from.

The bendable portion 312 has multiple wires 1a, 1b, and 1c extending through a face at the proximal end of the bendable portion 312 (the face where the center position is position 3127), a first wire guide 3121 to which the multiple wires 1a, 1b, and 1c are fixed at different positions, that guides the multiple wires 1a, 1b, and 1c, and second wire guides 3122 through 3125 that are disposed between the face at the proximal end described above and the first wire guide 3121, and that guide the multiple wires 1a, 1b, and 1c.

The wires are guided through the elongated portion 111 in the same way as with the continuum robot 110 according to the first embodiment, with the wire 1a being connected to a fixing portion 311a, the wire 1b being connected to an actuator 311b, and the wire 1c being connected to an actuator 311c. In the present embodiment, the wire 1a, wire 1b, and wire 1c are respectively laid out at the apices of an equilateral triangle of which the center axis of the bendable portion 312 is the center of gravity. Setting the drive control amount of the wire 1b and wire 1c enables the bendable portion 312 to be bent within an optional plane. For example, in a case where the wire 1b and wire 1c are driven in the same direction by the same amount, the bendable portion 312 bends within the X-Z plane in FIG. 14. In a case where the wire 1b and wire 1c are driven in opposites directions by the same amount, the bendable portion 312 bends within the Y-Z plane. A kinematic model and elastic wire driving model in the continuum robot 310 are derived in the present embodiment as well.

FIG. 15 is a diagram illustrating an example of a kinematic model at the bendable portion 312 illustrated in FIG. 14, according to the third embodiment of the present invention. In FIG. 15, the center position 3127 at the face of the proximal end of the bendable portion 312 illustrated in FIG. 14 is an origin $O_1$. The direction of the wire 1a is represented by an $X_1$ axis, the longitudinal direction of the bendable portion 312 is represented by a $Z_1$ axis, and a direction orthogonal to the $X_1$ axis and $Z_1$ axis is represented by a $Y_1$ axis. A direction from the origin $O_1$ in the $X_1$-$Y_1$ plane toward a center point $O_2$ in a face at the distal end 3126 of the bendable portion 312 is represented by a $W_1$ axis. And the angle formed between the $X_1$ axis and the $W_1$ axis is a rotation angle $\zeta_1$. Further, a center axis at the distal end 3126 is the origin, the normal direction is represented by a $Z_2$ axis, an $X_2$ axis is perpendicular to the $Z_2$ axis and on a $W_1$-$Z_1$ plane, and a $Y_2$ axis is in a direction perpendicular to the $X_2$ axis and $Z_2$ axis.

When the bending angle is $\theta_1$ and the rotation angle is $\zeta_1$, and the wire 1a and wire 1b are projected onto the $W_1$-$Z_1$ plane, a distance $R_{ba}$ between the wire 1a and wire 1b on the $W_1$-$Z_1$ plane can be expressed by the following Expression (44).

[Math. 12]

$$R_{ba} = \frac{\sqrt{3}}{2} R_g \cos\left(-\zeta_1 + \frac{\pi}{6}\right) \tag{44}$$

Accordingly, the following Expression (45) holds between the bending angle $\theta_1$ and lengths $l_{1a1}$ and $l_{1b1}$, in the same way as in Expression (1) according to the first embodiment.

[Math. 13]

$$\frac{\sqrt{3}}{2} R_g \cos\left(-\zeta_1 + \frac{\pi}{6}\right)\theta_1 = l_{1b1} - l_{1a1} \tag{45}$$

In the same way, the distance $R_{ca}$ between the wire 1a and wire 1c on the $W_1$-$Z_1$ plane can be expressed by the following Expression (46).

[Math. 14]

$$R_{ca} = \frac{\sqrt{3}}{2} R_g \cos\left(\zeta_1 + \frac{\pi}{6}\right) \quad (46)$$

Accordingly, the following Expression (47) holds between the bending angle $\theta_1$ and lengths $l_{1a1}$ and $l_{1c1}$.

[Math. 15]

$$\frac{\sqrt{3}}{2} R_g \cos\left(\zeta_1 + \frac{\pi}{6}\right)\theta_1 = l_{1c1} - l_{1a1} \quad (47)$$

From Expressions (45) and (47), the driving amount $l_{k1b}$ of the wire 1b and the driving amount $l_{k1c}$ of the wire 1c when assuming the wires to be rigid can be expressed by the following Expressions (48) and (49).

[Math. 16]

$$l_{k1b} = \frac{\sqrt{3}}{2} R_g \cos\left(-\zeta_1 + \frac{\pi}{6}\right)\theta_1 \quad (48)$$

$$l_{k1c} = \frac{\sqrt{3}}{2} R_g \cos\left(\zeta_1 + \frac{\pi}{6}\right)\theta_1 \quad (49)$$

Next, an elastic wire driving model is derived taking into consideration stretching and contraction of the wires. The lengths $l_{1a1}$ and $l_{1b1}$ in the continuum robot 310 according to the present embodiment, and the drive control amount $l_{p1b}$ of the wire 1b are expressed by Expressions (3) through (5), in the same way as in the first embodiment. The wire length $l_{1c1}$ can be expressed by the following Expression (50) using the drive control amount $l_{p1c}$ of the wire 1c, in the same way as with the wire length $l_{1b1}$.

$$l_{1c1} = l_{10} + \Delta l_{1c} + l_{p1c} \quad (50)$$

Accordingly, the drive control amount $l_{p1c}$ of the wire 1c is expressed by the following Expression (51).

$$l_{p1c} = l_{k1c} + \Delta l_{1a} - \Delta l_{1c} \quad (51)$$

It can be seen from this Expression (51) that the driving amount can be computed taking into consideration stretching and contraction of the wires in the continuum robot 310 according to the present embodiment, by adding the driving amount derived from the kinematic model to difference in wire displacements. Accordingly, a compensation amount $l_{e1c}$ of the wire 1c can be expressed by the following Expression (52).

$$l_{e1c} = \Delta l_{1a} - \Delta l_{1c} \quad (52)$$

An expression of balance of the force and moment acting on the distal end 3126 of the bendable portion 312 is derived to obtain the displacement of the wires. The balance of force can be expressed by the following Expression (53) using the forces $f_{1a}$, $f_{1b}$, and $f_{1c}$, since the distal end 3126 of the bendable portion 312 is under force in the Z 2 axis direction from the wire 1a, wire 1b, and wire 1c.

$$f_{1a} + f_{1b} + f_{1c} = 0 \quad (53)$$

Bending moments $M_{1a1}$, $M_{1b1}$, and $M_{1c1}$ on the $Y_2$ axis from the wire 1a, wire 1b, and wire 1c, act on the distal end 3126 of the bendable portion 312, and bending moment is balanced with the moment generated by the forces $f_{1a}$, $f_{1b}$, and $f_{1c}$ received from the wires. Accordingly, the balance of moments on the $Y_2$ axis can be expressed by the following Expression (54).

[Math. 17]

$$\frac{R_g}{2}\left\{f_{1a}\sin\left(-\zeta_1 - \frac{\pi}{2}\right) + f_{1b}\sin\left(-\zeta_1 + \frac{\pi}{6}\right) + f_{1c}\sin\left(-\zeta_1 + \frac{5\pi}{6}\right)\right\} - M_{1a1} - M_{1b1} - M_{1c1} = 0 \quad (54)$$

Moment due to the forces $f_{1a}$, $f_{1b}$, and $f_{1c}$ is generated on the $X_2$ axis, so the balance Expression can be expressed by the following Expression (55).

[Math. 18]

$$\frac{R_g}{2}\left\{f_{1a}\sin(-\zeta_1) + f_{1b}\sin\left(-\zeta_1 + \frac{2\pi}{3}\right) + f_{1c}\sin\left(-\zeta_1 + \frac{4\pi}{3}\right)\right\} = 0 \quad (55)$$

Note that the force and moment of the wire 1c can be expressed by the following Expressions (56) and (57) respectively, in the same way as with the wire 1a and the wire 1b.

[Math. 19]

$$f_{1c} = -k_e \Delta l_{1c} \quad (56)$$

$$M_{1c1} = -\frac{k_m}{l_{1c1}} \theta_1 \quad (57)$$

(3-2. Control System)

In the third embodiment, numerical solutions of the displacements $\Delta l_{1a}$, $\Delta l_{1b}$, and $\Delta l_{1a}$ of the wires are obtained using iterative calculation, in the same way as with the above-described second embodiment. FIG. 16 is a diagram illustrating an example of the functional configuration of a continuum robot control system 300 according to the third embodiment of the present invention. The continuum robot control system 300 illustrated in FIG. 16 is configured including the continuum robot 310 illustrated in FIG. 14, a continuum robot control device 320, an input device 330, and an input device 340.

The continuum robot control device 320 sets an drive control amount $l_{p1b}$ for diving control of the wire 1b and an drive control amount $l_{p1c}$ for diving control of the wire 1c, based on the target bending angle $\theta_{1ref}$ of the bendable portion 312 input from the input device 330, and target rotation angle $\zeta_{1ref}$ of the bendable portion 312 input from the input device 340, and outputs a driving command $\tau_{1b}$ based on the drive control amount $l_{p1b}$ and a driving command $\tau_{1c}$ based on the drive control amount $l_{p1c}$ to the continuum robot 310 (or more specifically, the actuators 311b and 311c). That is to say, the third embodiment differs from the above-described first embodiment with regard to the point that, in addition to input of the target bending angle $\theta_{1ref}$ from the input device 330, input of the target rotation angle $\zeta_{1ref}$ from the input device 340 is also performed.

The continuum robot control device 320 illustrated in FIG. 16 is configured including a kinematics computing unit 321, a compensation amount computing unit 322, an adding unit 323, and a position control unit 324.

The kinematics computing unit 321 calculates the driving amount $l_{k1b}$ and $l_{k1c}$ for each of the wires 1b and 1c, based on the target bending angle $\theta_{1ref}$ of the bendable portion 312 input from the input device 330, the target rotation angle $\zeta_{1ref}$ of the bendable portion 312 input from the input device 340, and the distance between the wires 1b and 1c (predetermined wires) and wire 1a (other wire). Specifically, the kinematics computing unit 321 calculates the driving amount $l_{k1b}$ and $l_{k1c}$ based on the kinematics model, using Expressions (48) and (49).

The compensation amount computing unit 322 computes the compensation amounts $l_{e1b}$ and $l_{e1c}$ for each of the wires 1b and 1c, based on the target bending angle $\theta_{1ref}$ of the bendable portion 312 input from the input device 330, the target rotation angle $\zeta_{1ref}$ of the bendable portion 312 input from the input device 340, and the displacements $\Delta l_{1a}$, $\Delta l_{1b}$, and $\Delta l_{1c}$ of the wires. Specifically, the compensation amount computing unit 322 first obtains the displacements $\Delta l_{1a}$, $\Delta l_{1b}$, and $\Delta l_{1c}$ of the wires by iterative calculation, and then calculates the compensation amounts $l_{e1b}$ and $l_{e1c}$, which are the differences of the displacements.

The adding unit 323 adds the driving amounts $l_{k1b}$ and $l_{k1c}$ calculated by the kinematics computing unit 321 and the compensation amounts $l_{e1b}$ and $l_{e1c}$ calculated by the compensation amount computing unit 322, for each of the wires 1b and 1c, thereby computing the drive control amounts $l_{p1b}$ and $l_{p1c}$. That is to say, the adding unit 323 performs processing of compensating the driving amounts $L_{k1b}$ and $l_{k1c}$ calculated by the kinematics computing unit 321 by the compensation amounts $l_{e1b}$ and $l_{e1c}$ calculated by the compensation amount computing unit 322, to calculate the drive control amount $l_{p1b}$ of the wire 1b and the drive control amount $l_{p1c}$ of the wire 1c. The position control unit 324 outputs a drive command $\tau_{1b}$ based on the drive control amount $l_{p1b}$ and a drive command $\tau_{1c}$ based on the drive control amount $l_{p1c}$ to the continuum robot 310 (or more specifically, to the actuators 311b and 311c). In the present embodiment, the adding unit 323 and position control unit 324 make up a setting device that sets the drive control amount $l_{p1b}$ of the wire 1b and the drive control amount $l_{p1c}$ of the wire 1c.

FIG. 17 is a diagram illustrating an example of the functional configuration of the compensation amount computing unit 322 illustrated in FIG. 16, according to the third embodiment of the present invention. The compensation amount computing unit 322 is configured including a displacement updating unit 3221, a convergence determining unit 3222, an output switching unit 3223, and a subtracting unit 3224, as illustrated in FIG. 17.

In accordance with input of the target bending angle $\theta_{1ref}$ and target rotation angle $\zeta_{1ref}$ and first displacement candidate values $\Delta l_{1a\_prev}$, $\Delta l_{1b\_prev}$, and $\Delta l_{1c\_prev}$ of the displacements of the wires 1a, 1b, and 1c, the displacement updating unit 3221 updates to second displacement candidate values $\Delta l_{1a\_next}$, $\Delta l_{1b\_next}$, and $\Delta l_{1c\_next}$. At this time, the displacement updating unit 3221 updates the second displacement candidate values $\Delta l_{1a\_next}$, $\Delta l_{1b\_next}$, and $\Delta l_{1c\_next}$ of the displacement of the wires 1a, 1b, and 1c, using the elastic wire driving model described above.

The convergence determining unit 3222 determines whether or not the second displacement candidate values $\Delta l_{1a\_next}$, $\Delta l_{1b\_next}$, and $\Delta l_{1b\_next}$ have converged at a constant value. In a case of having determined that the second displacement candidate values $\Delta l_{1a\_next}$, $\Delta l_{1b}$ next, and $\Delta l_{1c\_next}$ have converged at a constant value, the convergence determining unit 3222 causes the output switching unit 3223 to output the second displacement candidate values $\Delta l_{1a\_next}$, $\Delta l_{1b\_next}$, and $\Delta l_{1c\_next}$ as displacements $\Delta l_{1a}$, $\Delta l_{1b}$, and $\Delta l_{1c}$, to the subtracting unit 3224. In a case of having determined that the second displacement candidate values $\Delta l_{1a\_next}$, $\Delta l_{1b\_next}$, and $\Delta l_{1c\_next}$ have not converged at a constant value, the convergence determining unit 3222 causes the output switching unit 3223 to output the second displacement candidate values $\Delta l_{1a\_next}$, $\Delta l_{1b\_next}$, and $\Delta l_{1c\_next}$ as first displacement candidate values $\Delta l_{1a\_prev}$, $\Delta l_{1b\_prev}$, and $\Delta l_{1c\_prev}$ to the displacement updating unit 3221, and iterative calculation is performed again. The convergence determining unit 3222 and output switching unit 3223 according to the present embodiment make up a configuration corresponding to an output processing unit according to the present invention.

The subtracting unit 3224 is a compensation amount calculating unit that uses the second displacement candidate values $\Delta l_{1a\_next}$, $\Delta l_{1b\_next}$, and $\Delta l_{1c\_next}$ as displacements $\Delta l_{1a}$, $\Delta l_{1b}$, and $\Delta l_{1c}$, respectively, to calculate the compensation amounts $l_{e1b}$ and $l_{e1c}$, respectively, from Expression (52) and so forth.

Note that an arrangement may be made where, in a case that the second displacement candidate values $\Delta l_{1a\_next}$, $\Delta l_{1b\_next}$, and $\Delta l_{1c\_next}$ do not converge at a constant value within a predetermined iteration count, the convergence determining unit 3222 causes the output switching unit 3223 to output the last second displacement candidate values $\Delta l_{1a\_next}$, $\Delta l_{1b\_next}$, and $\Delta l_{1c\_next}$ to have converged, as displacements $\Delta l_{1a}$, $\Delta l_{1b}$, and $\Delta l_{1c}$, respectively, to the subtracting unit 3224. This can prevent the compensation amounts calculated at the subtracting unit 3224 from changing discontinuously. Although the initial values of the first displacement candidate values $\Delta l_{1a\_prev}$, $\Delta l_{1b\_prev}$, and $\Delta l_{1c\_prev}$ in the iterative calculation according to the present embodiment are 0, the displacements that converged last may be used as the initial values.

FIG. 18 is a diagram illustrating an example of the functional configuration of the displacement updating unit 3221 illustrated in FIG. 17, according to the third embodiment of the present invention. The displacement updating unit 3221 is configured including a wire length computing unit 32211, a moment computing unit 32212, a force computing unit 32213, and a displacement computing unit 32214, as illustrated in FIG. 18.

The wire length computing unit 32211 calculates the wire lengths $l_{1a1}$, $l_{1b1}$, and $l_{1c1}$, for each of the multiple wires 1a, 1b, and 1c at the bendable portion 312, in accordance with the input of the target bending angle $\theta_{1ref}$ and the first displacement candidate values $\Delta l_{1a\_prev}$, $\Delta l_{1b\_prev}$, and $\Delta l_{1c\_prev}$. Specifically, the wire length computing unit 32211 calculates the wire lengths $l_{1a1}$, $l_{1b1}$, and $l_{1c1}$, using the following Expressions (58) through (60), where Expressions (3), (5), and (48) through (51) have been modified.

[Math. 20]

$$l_{1a1} = l_{10} + \Delta l_{1a\_prev} \tag{58}$$

$$l_{1b1} = l_{10} + \Delta l_{1a\_prev} + \frac{\sqrt{3}}{2} R_g \cos\left(-\zeta_1 + \frac{\pi}{6}\right)\theta_{1ref} \tag{59}$$

$$l_{1c1} = l_{10} + \Delta l_{1a\_prev} + \frac{\sqrt{3}}{2} R_g \cos\left(\zeta_1 + \frac{\pi}{6}\right)\theta_{1ref} \tag{60}$$

The moment computing unit 32212 calculates bending moments $M_{1a1}$, $M_{1b1}$, and $M_{1c1}$, for each of the multiple wires 1a, 1b, and 1c, in accordance with the target bending angle $\theta_{1ref}$, target rotation angle and $\zeta_{1ref}$, the wire lengths $l_{1a1}$, $l_{1b1}$, and $l_{1c1}$ of the wires. Specifically, the moment computing unit 32212 calculates the bending moments $M_{1a1}$, $M_{1b1}$, and $M_{1c1}$ using Expressions (10) and (57).

The force computing unit 32213 calculates forces $f_{1a}$, $f_{1b}$, and $f_{1c}$ representing the tensile force on the wires 1a, 1b, and 1c, in accordance with the input of the bending moments $M_{1a1}$, $M_{1b1}$, and $M_{1c1}$, of the multiple wires 1a, 1b, and 1c. Specifically, the force computing unit 32213 calculates the forces $f_{1a}$, $f_{1b}$, and $f_{1c}$ using Expressions (53) through (55).

The displacement computing unit 32214 computes the second displacement candidate values $\Delta l_{1a\_next}$, $\Delta l_{1b\_next}$, and $\Delta l_{1c\_next}$ in accordance with the forces $f_{1a}$, $f_{1b}$, and $f_{1c}$ of the multiple wires 1a, 1b, and 1c, and updates displacement candidate values. Specifically, the displacement computing unit 32214 uses Expressions (9) and (56) to compute the second displacement candidate values $\Delta l_{1a\_next}$, $\Delta l_{1b\_next}$, and $\Delta l_{1c\_next}$, and updates the displacement candidate values.

(3-3. Simulation)

The control system according to the third embodiment, illustrated in FIGS. 16 through 18, is applied to the continuum robot 310 having the bendable portion 312 that is three-dimensionally bendable. Note that the length of the bendable portion 312 is 0.01 m, and the length of the elongated portion 111 is 1 m.

FIG. 19 is a characteristics diagram illustrating the relation between target bending angle and bending angle error. The horizontal axis in the characteristics diagram of FIG. 19 is the target bending angle $\theta_{1ref}$, and the vertical axis is the bending angle error.

Specifically, FIG. 19 shows bending angle error of the bendable portion 312 in a case where the target rotation angle $\zeta_{1ref}$ is 0 degrees, and the target bending angle $\theta_{1ref}$ is changed from −90 degrees to 90 degrees. The dashed line in FIG. 19 illustrates a comparative example of a case where the driving amounts $l_{k1b}$ and $l_{k1c}$ calculated using the kinematics model are used as control input. It can be understood that in this case, the angle error of the bendable portion 312 increases in accordance with the increase or decrease of the target bending angle $\theta_{1ref}$. On the other hand, the solid line illustrates the present embodiment in a case of using the drive control amounts $l_{p1b}$ and $l_{p1c}$ taking stretching and contraction of the wires into consideration. It can be understood that in this case, the angle error of the bendable portion 312 is 0 even if there is change in the target bending angle $\theta_{1ref}$.

FIG. 20 is a characteristics diagram illustrating the relation between target rotation angle and bending angle error according to the third embodiment of the present invention. The horizontal axis in the characteristics diagram of FIG. 20 is the target rotation angle $\zeta_{1ref}$, and the vertical axis is the bending angle error.

Specifically, FIG. 20 shows bending angle error of the bendable portion 312 in a case where the target bending angle $\theta_{1ref}$ is 90 degrees, and the target rotation angle $\zeta_{1ref}$ is changed from −180 degrees to 180 degrees. The dashed line in FIG. 20 illustrates a comparative example of a case where the driving amounts $l_{k1b}$ and $l_{k1c}$ calculated using the kinematics model are used as control input. It can be understood that in this case, angle error of the bendable portion 312 occurs dependent on the target rotation angle $\zeta_{1ref}$. On the other hand, the solid line illustrates the present embodiment in a case of using the drive control amounts $l_{p1b}$ and $l_{p1c}$ taking stretching and contraction of the wires into consideration as control input. It can be understood that in this case, the angle error of the bendable portion 312 is 0 regardless of the target rotation angle $\zeta_{1ref}$. From the above, it can be understood that attitude error of the continuum robot 310 having the bendable portion 312 that can be three-dimensionally bent can be reduced, by applying the control system illustrated in FIGS. 16 through 18 according to the present embodiment.

In the continuum robot control device 320 according to the third embodiment, the compensation amount computing unit 322 computes the respective compensation amounts $l_{e1b}$ and $l_{e1c}$ for the wires 1b and 1c, based on the target bending angle $\theta_{1ref}$ of the bendable portion 312 input from the input device 330, and the target rotation angle $\zeta_{1ref}$ of the bendable portion 312 input from the input device 340, for each wire 1b and 1c (predetermined wires) of the bendable portion 312. The adding unit 323 and position control unit 324 perform processing to compensate the respective driving amounts $l_{k1b}$ and $l_{k1c}$ calculated at the kinematics computing unit 321, by the compensation amounts $l_{e1b}$ and $l_{e1c}$ calculated at the compensation amount computing unit 322, thereby setting the drive control amounts $l_{p1b}$ and $l_{p1c}$ of the wires 1b and 1c. According to this configuration, error in the driving amounts $l_{k1b}$ and $l_{k1c}$ due to wire deformation can be compensated for in the continuum robot 310 having the bendable portion 312 that is three-dimensionally bendable, as well. Accordingly, error between the reference position of the bendable portion 312 and the actual attitude can be reduced, and as a result, reduction in the risk of contact between a path in the body or the like and the bendable portion can be realized.

The driving amount of each wire can be compensated for in the present embodiment using the compensation amount calculated based on the displacement of any one wire of the multiple wires relating to the same bendable portion, in the same way as in the first embodiment.

Fourth Embodiment

Next, a fourth embodiment of the present invention will be described. The fourth embodiment is an arrangement of applying a continuum robot having multiple bendable portions that are bendable three-dimensionally, by combining the control system according to the second embodiment and the control system according to the third embodiment. Specifically, the control system according to the fourth embodiment computes displacement of the wires that drive the bendable portions, using iterative calculation. When carrying out iterative calculation, the elastic wire driving model that takes into consideration coupling of force and moment acting among the bendable portions is used in the same way as in the second embodiment. Further, the control system according to the fourth embodiment obtains the driving amount from the target bending angle and target rotation angle.

(4-1. Modelling)

FIG. 21 is a diagram illustrating an example of a schematic configuration of a continuum robot 410 used in the fourth embodiment of the present invention. Configurations that are the same as configurations illustrated in FIGS. 1, 2, 7, and 14 are denoted by the same symbols, and detailed description thereof will be omitted. FIG. 21 also illustrates an example of a path into which a bendable portions 412 is inserted and removed from.

The bendable portion 412 is configured having multiple (specifically, N) bendable portions 312 illustrated in FIG. 14 in the direction of inserting to and removing from the path. That is to say, this continuum robot 410 illustrated in FIG. 21 is configured having multiple bendable portions 312-1 through 312-N, arranged serially. One end of a wire na, wire nb, and wire nc, is connected to a distal end 3126-$n$ of an n'th bendable portion (where n=1, 2, ..., N) of the bendable portion 412. The wires na, nb, and nc are guided from an n-1'th bendable portion 312-(n-1) to wire guides of a first bendable portion 312-1 and the elongated portion 111. The wire na is connected to a fixing portion 411$a$, the wire nb is connected to an actuator 411$b$, and the wire nc is connected to an actuator 411$c$. Note that in the example illustrated in FIG. 21, the actuator 411$b$ is a driving mechanism that can drive each of wires 1$b$ through Nb independently. Also note that an arrangement may be made where N actuators 411$b$ corresponding to the wires 1$b$ through Nb are configured. In the same way, the actuator 411$c$ is a driving mechanism that can drive each of wires 1$c$ through Nc independently, and an arrangement may be made where N actuators 411$c$ corresponding to the wires 1$c$ through Nc are configured. In the present embodiment, the bending angle On and rotation angle In at the n'th bendable portion 312-$n$ are controlled by driving control of the actuators 411$b$ and 411$c$.

(4-2. Control System)

FIG. 22 is a diagram illustrating an example of the functional configuration of a continuum robot control system 400 according to the fourth embodiment of the present invention. The continuum robot control system 400 illustrated in FIG. 22 is configured including the continuum robot 410 illustrated in FIG. 21, a continuum robot control device 420, an input device 430, and an input device 440.

The kinematics computing unit 421 accepts target bending angle $\theta_{nref}$ and target rotation angle $\zeta_{nref}$ (where n=1, 2, ..., N) from the input device 430 and input device 440 respectively, for the first bendable portion 312-1 through the N'th bendable portion 312-N, and calculates the driving amount $l_{knb}$ and $l_{knc}$ for each bendable portion using the kinematic model in the same way as the third embodiment.

The compensation amount computing unit 422 accepts input of target bending angle $\theta_{nref}$ and target rotation angle $\zeta_{nref}$ (where n=1, 2, ..., N) from the input device 430 and input device 440 respectively, for the first bendable portion 312-1 through the N'th bendable portion 312-N, and calculates the compensation amounts $l_{enb}$ and $l_{enc}$ of the bendable portions. At this time, the compensation amount computing unit 422 calculates the displacements $\Delta l_{na}$, $\Delta l_{nb}$, and $\Delta l_{nc}$ using the elastic wire driving model that takes into consideration coupling of force and moment acting among the bendable portions, and iterative calculation, in the same way as in the second embodiment, and calculates the compensation amounts $l_{enb}$ and $l_{enc}$ from these displacements.

The adding unit 423 adds the driving amounts $l_{knb}$ and $l_{knc}$ calculated by the kinematics computing unit 421 and the compensation amounts $l_{enb}$ and $l_{enc}$ calculated by the compensation amount computing unit 422, thereby computing the drive control amounts $l_{pnb}$ and $l_{pnc}$. That is to say, the adding unit 423 performs processing of compensating the driving amounts $l_{knb}$ and $l_{knc}$ calculated by the kinematics computing unit 421 respectively by the compensation amounts $l_{cnb}$ and $l_{enc}$ calculated by the compensation amount computing unit 422, to calculate the drive control amount $l_{pnb}$ of the wire nb and the drive control amount $l_{pnc}$ of the wire nc. The position control unit 424 outputs a drive command $\tau_{nb}$ based on the drive control amount $l_{pnb}$ and a drive command $\tau_{nc}$ based on the drive control amount $l_{pnc}$ to the continuum robot 410 (or more specifically, to the actuators 411$b$ and 411$c$). In the present embodiment, the adding unit 423 and position control unit 424 make up a setting device that sets the drive control amount $l_{pnb}$ for driving control of the wire nb and the drive control amount $l_{pnc}$ for driving control of the wire nc.

According to the fourth embodiment, error in the driving amounts $l_{knb}$ and $l_{knc}$ due to wire deformation can be compensated for in the continuum robot 410 having the multiple bendable portions 412 that are three-dimensionally bendable, as well. Accordingly, error between the target posture of the bendable portion 412 and the actual attitude can be reduced, and as a result, reduction in the risk of contact between a path in the body or the like and the bendable portion can be realized.

The driving amount of each wire can be compensated for in the present embodiment using the compensation amount calculated based on the displacement of any one wire of the multiple wires relating to the same bendable portion, in the same way as in the first embodiment.

Fifth Embodiment

Next, a fifth embodiment of the present invention will be described. The above-described first through fourth embodiments have been arrangements presenting a control system that obtains driving amount control, taking into consideration stretching and contraction of the wires, when a certain reference angle is provided. The fifth embodiment is an arrangement where, when a reference path in which a reference angle (e.g., target bending angle) changes in a manner dependent on the amount of movement of the distal end of a bendable portion in the longitudinal direction, the attitude of the bendable portion is automatically controlled to follow the path.

The continuum robots according to the above-described first through fourth embodiments are dependent on the amount of wire driving for the position of the distal end of the bendable portion, so the reference angle when following a reference path will be dependent on the amount of wire driving. At this time, the amount of wire driving cannot be directly obtained using the control systems in the above-described first through fourth embodiments. The reason is that the control systems in the above-described first through fourth embodiments need a reference angle to be set, to obtain the driving amount. Accordingly, the control system according to the fifth embodiment obtains the driving control amount by performing iterative calculation, where updating is repeated until the reference angle and amount of wire driving converge to a constant value. Specifically, in the fifth embodiment, a candidate value for reference angle is first input, and a candidate value for the amount of wire driving is computed using the control system according to the first embodiment. Next, the distal end position corresponding to the candidate value for the driving amount is computed, and the candidate value for the reference angle is updated based on the distal end position and reference path. This computation is repeated until the candidate value for the driving amount converges.

(5-1. Modelling)

FIG. 23 is a diagram illustrating an example of the external configuration of a continuum robot control system 500 used in the fifth embodiment of the present invention. The continuum robot control system 500 illustrated in FIG. 23 is configured including the elongated portion 111 and bendable portion 112 illustrated in FIG. 1, and a base portion 511, a linear guide 512, and a position detector 513.

The continuum robot according to the fifth embodiment is the continuum robot 110 illustrated in FIG. 1, configured having one bendable portion 112, in the same way as the first embodiment. The base portion 511 is fixed to the linear guide 512, and the continuum robot 110 in the fifth embodiment advances and retracts along the linear guide 512 by pushing and pulling the base portion 511. The position detector 513 that measures movement amount $z_b$ of the linear guide 512 is attached to the linear guide 512. This movement amount $z_b$ of the linear guide 512 is input from the position detector 513 to a continuum robot control device 520 illustrated in FIG. 25, which will be described later. Before driving the linear guide 512, a target bending angle path $\Theta(z_t)$ is input from a higher-order device (omitted from illustration) to the continuum robot control device 520 illustrated in FIG. 25, which will be described later. The target bending angle path $\Theta(z_t)$ in the present embodiment is a function of a movement amount $z_t$ of the distal end 1126 of the bendable portion 112.

(5-2. Control System)

The control system according to the fifth embodiment finds a drive control amount $l_{p1b}$ where the bending angle $\theta_1$ of the distal end 1126 matches the target bending angle path $\Theta(z_t)$. At this time, the drive control amount $l_{p1b}$ is a function of the target bending angle path $\Theta(z_t)$, so the drive control amount $l_{p1b}$ cannot be obtained with the bending angle $\theta_{1ref}$ as a constant, which has been described in the first embodiment. Accordingly, the drive control amount $l_{p1b}$ is obtained by iterative calculation in the fifth embodiment. First, a method for computing the movement amount $z_t$ of the distal end 1126 of the bendable portion 112 will be described.

FIG. 24 is a diagram illustrating an example of kinematic model of the bendable portion 112 illustrated in FIG. 23, according to the fifth embodiment of the present invention. With the length of an axis connecting the distal end 1126 of the bendable portion 112 and the center of each wire guide as $l_{1d}$, this $l_{1d}$ can be expressed by the following Expression (61) using the drive control amount $l_{p1b}$.

[Math. 21]

$$l_{1d} = l_{10} + \frac{l_{p1b}}{2} \quad (61)$$

Accordingly, the movement amount $z_t$ of the distal end 1126 of the bendable portion 112 can be expressed by the following Expression (62) using the movement amount $z_b$ of the linear guide 512.

[Math. 22]

$$z_t = l_0 + \frac{l_{p1b}}{2} + z_b \quad (62)$$

Next, the functional configuration of the continuum robot control system 500 according to the fifth embodiment will be described. FIG. 25 is a diagram illustrating an example of the functional configuration of the continuum robot control system 500 according to the fifth embodiment of the present invention. The continuum robot control system 500 illustrated in FIG. 25 is configured including the continuum robot 110 illustrated in FIG. 1, the continuum robot control device 520, and the position detector 513.

The continuum robot control device 520 is configured including a distal end position computing unit 521, a reference angle updating unit 522, a kinematics computing unit 523, a compensation amount computing unit 524, an adding unit 525, a convergence determining unit 526, an output switching unit 527, and a position control unit 528.

The distal end position computing unit 521 is a third computing device that computes the movement amount $z_t$ of the distal end 1126 of the bendable portion 112 in accordance with the movement amount (movement amount of the continuum robot 110 in the longitudinal direction) $z_b$ of the linear guide 512, and input of a first driving control amount candidate value $l_{p1b\_prev}$ in the driving control amount of the wire 1b (predetermined wire). Specifically, the distal end position computing unit 521 calculates the movement amount $z_t$ of the distal end 1126 of the bendable portion 112 using Expression (62).

The reference angle updating unit 522 updates the target bending angle $\theta_{1ref}$ corresponding to the movement amount $z_t$, in accordance with the movement amount $z_t$ of the distal end 1126 from the distal end position computing unit 521 and input of the target bending angle path $\Theta(z_t)$ from the higher-order device (omitted from illustration) described above.

The kinematics computing unit 523 calculates the driving amount $l_{k1b}$ of the wire 1b, in accordance with input of the target bending angle $\theta_{1ref}$ from the reference angle updating unit 522, in the same way as in the first embodiment. Further, the compensation amount computing unit 524 calculates the compensation amount $l_{e1b}$ of the wire 1b, in accordance with input of the target bending angle $\theta_{1ref}$ from the reference angle updating unit 522, in the same way as in the first embodiment.

The adding unit 525 adds the driving amount $l_{k1b}$ calculated at the kinematics computing unit 523 and the compensation amount $l_{e1b}$ calculated at the compensation amount computing unit 524, and calculates a second driving control amount candidate value $l_{p1b\_next}$ for the driving control amount of the wire 1b. The convergence determining unit 526 determines whether or not the second driving control amount candidate value $l_{p1b\_next}$ has converged to a constant value. In a case of having determined that the second driving control amount candidate value $l_{p1b\_next}$ has converged to a constant value, the convergence determining unit 526 causes the output switching unit 527 to output the second driving control amount candidate value $l_{p1b\_next}$ to the position control unit 528 as the drive control amount $l_{p1b}$. In a case of having determined that the second driving control amount candidate value $l_{p1b\_next}$ has not converged to a constant value, the convergence determining unit 526 causes the output switching unit 527 to output the second driving control amount candidate value $l_{p1b\_next}$ to the distal end position computing unit 521 as the first driving control amount candidate value $l_{p1b\_prev}$, and iterative calculation is performed again. The position control unit 528 outputs a driving command $\tau_{1b}$ based on the drive control amount $l_{p1b}$, to the continuum robot 110 (or more specifically, the actuator 113), in the same way as in the first embodiment. In the present embodiment, the adding unit 525, convergence determining unit 526, output switching unit 527, and position control unit 528 make up a setting device that sets the drive control amount $l_{p1b}$ for diving control of the wire 1b.

Note that while a control system of performing control with regard to the continuum robot 110 having one bendable portion 112 has been described in the present embodiment, this is similarly applicable to the continuum robot 410 having multiple bendable portions 412 that are three-dimensionally bendable, for example.

Sixth Embodiment

Next, a sixth embodiment of the present invention will be described. Description of items that are the same as in the above-described first through fifth embodiments will be omitted from the following description of the sixth embodiment, and description will be made regarding items that are different from the above-described first through fifth embodiments.

The sixth embodiment is an arrangement where a continuum robot of which the rigidity of the bendable portion changes by a jacket or by insertion of surgical instruments is applied. Specifically, the continuum robot according to the sixth embodiment is suitable for use as a flexible endoscope described in the Background Art section. This type of continuum robot preferably has the surface thereof covered by a smooth jacket so that body tissue is not damaged even if the continuum robot comes into contact with the tissue, for example. There is need to perform bending driving of the jacket along with the bendable portion, so there is need to drive the wires with a larger tensile force as compared to a continuum robot that has no jacket. Some flexible endoscopes have a hollow structure for insertion of surgical instruments such as forceps of the like, used for bioptic sampling of diseased tissue, or the like. In order to drive the bendable portion of the continuum robot in a state where a surgical instrument is inserted, the surgical instrument has to be bent as well, so there is need to drive the wires with a larger tensile force as compared to when no surgical instrument is inserted. Accordingly, the rigidity of the bendable portion differs depending on the presence or absence of jacket and surgical instrument. In light of this point, the control systems in the above-described first through fifth embodiments only take into consideration the rigidity of the wires when obtaining the displacement of the wires, so angle error cannot be accurately compensated for if the rigidity of the bendable portion changes depending on the presence or absence of jacket and surgical instrument. Accordingly, the sixth embodiment illustrates an example of a control system where the rigidity of the bendable portion can be specified as a variable.

(6-1. Modelling)

FIGS. 26A and 26B are diagrams illustrating an example of a schematic configuration of a continuum robot 610 used in the sixth embodiment of the present invention. More specifically, FIGS. 26A and 26B are diagrams illustrating cross-sections of the continuum robot 610 used in the sixth embodiment of the present invention, taken along a plane parallel to the longitudinal direction of a bendable portion 612. Note that the continuum robot 610 according to the present embodiment is capable of bending three-dimensionally, in the same way as the continuum robot 310 in the third embodiment illustrated in FIG. 14. Note that the continuum robot 610 illustrated in FIGS. 26A and 26B has the multiple wires 1a, 1b, and 1c, and also is configured including the fixing portion 311a to which the wire 1a is connected, the actuator 311b to which the wire 1b is connected, and actuator 311c to which the wire 1c is connected, which are illustrated in FIG. 14, although omitted from illustration in FIGS. 26A and 26B, in the same way as the continuum robot 310 according to the third embodiment illustrated in FIG. 14.

The continuum robot 610 according to the present embodiment is configured including an elongated portion 611 and a bendable portion 612, as illustrated in FIG. 26A. Multiple wire guides 613 are also provided to the bendable portion 612. The elongated portion 611 and bendable portion 612 further have a cylindrical hollow portion 614, by which a surgical instrument 616 can be inserted from the proximal end of the elongated portion 611 to the distal end of the bendable portion 612. The continuum robot 610 also has a jacket 615 that covers the sides and tip of the bendable portion 612 and the hollow portion 614.

The proximal end of the jacket 615 is fixed to the distal end of the elongated portion 611, so when bending driving of the bendable portion 612 is performed, the outer side of the jacket 615 stretches, and the inner side of the jacket 615 is compressed, as illustrated in FIG. 26B. The surgical instrument 616 is also bent following the bendable portion 612. Accordingly, the bending rigidity of the bendable portion 612 is greater as compared to the continuum robots in the above-described first through fifth embodiments.

In the present embodiment, the following Assumptions 13 and 14 are set forth, and an elastic wire driving model is derived that takes into consideration the bending rigidity of the jacket 615 and surgical instrument 616. Assumption 13 is that the magnitude of bending moment of the jacket 615 and surgical instrument 616 is proportionate to the bending angle of the bendable portion 612. Assumption 14 is that the rotation axis of bending moment of the jacket 615 and surgical instrument 616 is parallel to the $Y_2$ axis.

Based on Assumption 13, the balance of moment on the $Y_2$ axis at the distal end of the bendable portion 612 can be expressed by the following Expression (63) in which items representing the bending moment of the jacket 615 and surgical instrument 616 have been added to Expression (54), in which $k_{mc}$ represents the bending rigidity of the jacket 615 and $k_{mt}$ represents the bending rigidity of the surgical instrument 616.

[Math. 23]

$$\frac{R_g}{2}\left\{f_{1a}\sin\left(-\zeta_1 - \frac{\pi}{2}\right) + f_{1b}\sin\left(-\zeta_1 + \frac{\pi}{6}\right) + f_{1c}\sin\left(-\zeta_1 + \frac{5\pi}{6}\right)\right\} - \\ M_{1a1} - M_{1b1} - M_{1c1} + k_{mc}\theta_1 + k_{mt}\theta_1 = 0 \quad (63)$$

Based on Assumption 14, the balance of moment on the $X_2$ axis is not affected by the rigidity of the jacket 615 and surgical instrument 616, so Expression (55) is appropriate for the continuum robot 610 according to the present embodiment as well. The bending rigidity $k_{mc}$ of the jacket 615 and the bending rigidity $k_{mt}$ of the surgical instrument 616 may be identified through experimentation, or may be analytically derived.

(6-2. Control System)

In the sixth embodiment, the displacement of the wires is derived taking into consideration the rigidity of the jacket 615 and surgical instrument 616, by performing iterative calculation the same as in the third embodiment, using Expression (63). FIG. 27 is a diagram illustrating an example of the functional configuration of a continuum robot control system 600 according to the sixth embodiment of the present invention. Configurations that are the same as configurations of the third embodiment illustrated in FIG. 16 are denoted by the same symbols, and detailed description thereof will be omitted.

The continuum robot control system 600 illustrated in FIG. 27 is configured including the continuum robot 610 illustrated in FIG. 26, a continuum robot control device 620, an input device 630, an input device 640, and an input device 650. The continuum robot control device 620 is configured including the kinematics computing unit 321, a compensation amount computing unit 622, the adding unit 323, and the position control unit 324.

The compensation amount computing unit 622 computes the compensation amounts $l_{e1b}$ and $l_{e1c}$ for each of the wires 1b and 1c, based on the target bending angle $\theta_{1ref}$ of the bendable portion 612 input from the input device 630, the target rotation angle $\zeta_{1ref}$ of the bendable portion 612 input from the input device 640, and the bending rigidity $k_{mc}$ of the jacket 615 and the bending rigidity $k_{mt}$ of the surgical instrument 616 input from the input device 650. Although the bending rigidity $k_{mc}$ of the jacket 615 and the bending rigidity $k_{mt}$ of the surgical instrument 616 is assumed to be constant in the present embodiment, an arrangement may be made where, when the rigidity has non-linearity dependent on bending angle or rotation angle, rigidities corresponding to various bending angles and rotation angles are stored in a storage device before the procedure, and rigidities corresponding to target bending angles and target rotation angles are read out during the procedure. Alternatively, the operator may directly input the bending rigidity $k_{mc}$ of the jacket 615 and the bending rigidity $k_{mt}$ of the surgical instrument 616. Note that the kinematics computing unit 321, adding unit 323, and position control unit 324 are the same as in the third embodiment illustrated in FIG. 16, so description will be omitted.

FIG. 28 is a diagram illustrating an example of the functional configuration of the compensation amount computing unit 622 illustrated in FIG. 27, according to the sixth embodiment of the present invention. Configurations in FIG. 28 that are the same as configurations illustrated in FIG. 27 and configurations of the third embodiment illustrated in FIG. 17 are denoted by the same symbols, and detailed description thereof will be omitted. The compensation amount computing unit 622 illustrated in FIG. 28 is configured including a displacement updating unit 6221, the convergence determining unit 3222, the output switching unit 3223, and the subtracting unit 3224.

In accordance with input of the target bending angle $\theta_{1ref}$ and target rotation angle $\zeta_{1ref}$, the bending rigidity $k_{mc}$ of the jacket 615 and bending rigidity $k_{mt}$ of the surgical instrument 616, and first displacement candidate values $\Delta l_{1a\_prev}$, $\Delta l_{1b\_prev}$, and $\Delta l_{1c\_prev}$, in displacement of the wires 1a, 1b, and 1c, the displacement updating unit 6221 updates to second displacement candidate values $\Delta l_{1a\_next}$, $\Delta l_{1b\_next}$, and $\Delta l_{1c\_next}$. Note that the convergence determining unit 3222, output switching unit 3223, and subtracting unit 3224 are the same as in the third embodiment illustrated in FIG. 17, so description will be omitted.

FIG. 29 is a diagram illustrating an example of the functional configuration of the displacement updating unit 6221 illustrated in FIG. 28, according to the sixth embodiment of the present invention. Configurations in FIG. 29 that are the same as configurations illustrated in FIG. 28 and configurations of the third embodiment illustrated in FIG. 18 are denoted by the same symbols, and detailed description thereof will be omitted. The displacement updating unit 6221 illustrated in FIG. 29 is configured including the wire length computing unit 32211, the moment computing unit 32212, a force computing unit 62213, and the displacement computing unit 32214.

The force computing unit 62213 calculates forces $f_{1a}$, $f_{1b}$, and $f_{1c}$ representing the tensile force on the wires 1a, 1b, and 1c, in accordance with the input of the bending rigidity $k_{mc}$ of the jacket 615 and bending rigidity $k_{mt}$ of the surgical instrument 616, in addition to the input of the bending moments $M_{1a1}$, $M_{1b1}$, and $M_{1c1}$, of the multiple wires 1a, 1b, and 1c, using Expression (53) that expresses balance of force, and Expressions (55) and (63) that express balance of moment. Note that the wire length computing unit 32211, moment computing unit 32212, and the displacement computing unit 32214 are the same as in the third embodiment illustrated in FIG. 18, so description will be omitted.

Although a model is derived that includes the bending rigidity $k_{mc}$ of the jacket 615 and bending rigidity $k_{mt}$ of the surgical instrument 616 as shown in Expression (63) in the present embodiment, an arrangement may be made where displacement is calculated using an approximation expression where the bending rigidity $k_m$ of the wires in Expressions (10) and (57) is replaced with a rigidity $k_{me}$ that takes into consideration with the rigidity of the jacket 615 and surgical instrument 616 as well. Alternatively, the rigidity $k_{me}$ may be identified through experimentation, or a value obtained by dividing the bending rigidity $k_{mc}$ of the jacket 615 and bending rigidity $k_{mt}$ of the surgical instrument 616 by the wire count n may be added to the wire bending rigidity $k_m$, as shown in the following Expression (64).

[Math. 24]

$$k_{me} = k_m + \frac{k_{mc} + k_{mt}}{n} \quad (64)$$

While the continuum robot control device 620 is applied to the continuum robot 610 having one bendable portion 612 that is three-dimensionally bendable in the present embodiment, application may be made to the continuum robot 110 that curves on a plane as in the first embodiment, or the continuum robot 410 that has multiple bendable portions 312 as in the fourth embodiment.

(6-3. Simulation)

The control system according to the sixth embodiment illustrated in FIGS. 27 through 29 is applied to the continuum robot 610 that has the jacket 615, and through which the surgical instrument 616 has been inserted. The bending rigidity $k_{mc}$ of the jacket 615 and bending rigidity $k_{mt}$ of the surgical instrument 616 here are both assumed to be 0.33 Nm/rad.

FIG. 30 is a characteristic diagram illustrating the relation between target rotation angle and bending angle error according to the sixth embodiment of the present invention. The horizontal axis in the characteristics diagram of FIG. 30 is the target rotation angle $\zeta_{1ref}$, and the vertical axis is the bending angle error, in the same way as in FIG. 20.

Specifically, the dashed line shown at the top in FIG. 30 illustrates a comparative example of a case where the driving amounts $l_{k1b}$ and $l_{k1c}$ calculated using the kinematics model are used as control input. It can be understood that in this case, great angle error of the bendable portion 612 occurs dependent on the target rotation angle $\zeta_{1ref}$. Also, the dotted line shown at the middle illustrates a comparative example of a case where the drive control amounts $l_{p1b\_wo}$ and $l_{p1c\_wo}$ calculated using the continuum robot control device 320 according to the third embodiment are used as control input. It can be understood that in this case, angle error cannot be completely compensated for by the continuum robot control device 320 according to the third embodiment, since increase in rigidity of the bendable portion 612 due to the jacket 615 and surgical instrument 616 has not been taken into consideration. On the other hand, the solid line shown to the bottom represents response when using drive control amounts $l_{p1b\_w}$ and $l_{p1c\_w}$ computed using the continuum robot control device 620 according to the present embodiment, and it can be understood that the angle error of the bendable portion 612 is constantly 0, regardless of the target rotation angle $\zeta_{1ref}$. From the above description, it can be understood that attitude error of the continuum robot 610 can be reduced by applying the control system according to the sixth embodiment illustrated in FIGS. 27 through 29, to the continuum robot 610 that has the jacket 615, and through which the surgical instrument 616 has been inserted.

Seventh Embodiment

Next, a seventh embodiment of the present invention will be described. Description of items that are the same as in the above-described first through sixth embodiments will be omitted from the following description of the seventh embodiment, and description will be made regarding items that are different from the above-described first through sixth embodiments.

The continuum robot 310 according to the third embodiment illustrated in FIG. 14 has the actuators 311b and 311c connected to, out of the three wires 1a, 1b, and 1c, the wires 1b and 1c respectively, and the bendable portion 312 can be three-dimensionally bent. Accordingly, in a case where one of the two actuators 311b and 311c stops operating due to malfunction, the bendable portion 312 becomes capable of bending only on a plane, so the risk of tissue and the continuum robot 310 coming into contact increases. On the other hand, if all wires 1a, 1b, and 1c are connected to actuators, three-dimensional bending operations can be realized by a control system like that of the third embodiment even if one actuator happens to malfunction, and accordingly the continuum robot control system can be imparted redundancy. Accordingly, an example is illustrated in the seventh embodiment regarding a control system that is applicable to a continuum robot capable of driving all three wires 1a, 1b, and 1c.

(7-1. Modelling)

The continuum robot used in the present embodiment differs from the continuum robot 310 according to the third embodiment, with regard to the point that the wire 1a illustrated in FIG. 14 is not connected to the fixing portion 311a, but rather to an actuator 311a'. The continuum robot where the wire 1a illustrated in FIG. 14 is connected to the actuator 311a' instead of the fixing portion 311a will be described as a "continuum robot 710" used in the seventh embodiment.

In the continuum robot 710, using the actuators 311a', 311b, and 311c to drive the wire 1a, wire 1b, and wire 1c respectively, by the same distance in the same direction, the length of the center axis of the bendable portion corresponding to the bendable portion 312 increases or decreases with the bending angle and rotation angle remaining constant. Accordingly, the length of the center axis length $l_{1dc}$ of the bendable portion can be controlled with the continuum robot 710 according to the present embodiment, in addition to the bending angle $\theta_1$ and the rotation angle $\zeta_1$.

The configuration of the bendable portion of the continuum robot 710 used in the present embodiment has the same configuration as the bendable portion 312 used in the third embodiment, so a kinematics model and elastic wire model is derived for the continuum robot 710 using FIG. 15. When the bending angle of the bendable portion of the continuum robot 710 is $\theta_1$ and the rotation angle is $\zeta_1$, a distance $R_{oa}$ between the origin $O_1$ on the $W_1$-$Z_1$ plane and the wire 1b can be expressed by the following Expression (65).

[Math. 25]

$$R_{oa} = \frac{R_g}{2}\cos(\zeta_1) \quad (65)$$

Accordingly, the following Expression (66) holds between the center axis length $l_{1dc}$ and the length $l_{1a1}$.

[Math. 26]

$$l_{1d1} = -\frac{R_g \theta_1}{2}\cos(\zeta_1) + l_{1dc} \quad (66)$$

Also, from Expressions (45) and (46), the length $l_{1b1}$ and the length $l_{1c1}$ can be expressed by Expressions (67) and (68) using length $l_{1dc}$.

[Math. 27]

$$l_{1b1} = -\frac{R_g \theta_1}{2}\cos\left(\zeta_1 - \frac{2\pi}{3}\right) + l_{1dc} \quad (67)$$

[Math. 28]

$$l_{1c1} = -\frac{R_g \theta_1}{2}\cos\left(\zeta_1 - \frac{4\pi}{3}\right) + l_{1dc} \quad (68)$$

Assuming that the wires 1a, 1b, and 1c are rigid in the longitudinal direction, the respective wire lengths $l_{1a1}$, $l_{1b1}$, and $l_{1a1}$ are expressed as being the sums of the driving amounts $l_{k1a}$, $l_{k1b}$, and $l_{k1c}$, derived from the kinematic model, and the length $l_{10}$. Accordingly, the driving amounts $l_{k1a}$, $l_{k1b}$, and $l_{k1c}$ are respectively expressed by the following Expressions (69), (70), and (71).

[Math. 29]

$$l_{k1a} = -\frac{R_g \theta_1}{2}\cos(\zeta_1) + l_{1dc} - l_0 \quad (69)$$

[Math. 30]

$$l_{k1b} = -\frac{R_g \theta_1}{2}\cos\left(\zeta_1 - \frac{2\pi}{3}\right) + l_{1dc} - l_0 \quad (70)$$

[Math. 31]

$$l_{k1c} = -\frac{R_g \theta_1}{2}\cos\left(\zeta_1 - \frac{4\pi}{3}\right) + l_{1dc} - l_0 \quad (71)$$

Next, assuming that the wires 1a, 1b, and 1c stretch and contract in the longitudinal direction, the respective displacements $\Delta l_{1a}$, $\Delta l_{1b}$, and $\Delta l_{1c}$ are obtained. Based on Expressions (9) and (56), defining matrix $K_e$ and vector f, $\Delta l_1$ respectively as shown in the following Expressions (72) and (73), $\Delta l_1$ is expressed as in the following Expression (74).

[Math. 32]

$$K_e = \begin{bmatrix} k_e & 0 & 0 \\ 0 & k_e & 0 \\ 0 & 0 & k_e \end{bmatrix} \quad (72)$$

-continued $$f = [\, f_{1a} \quad f_{1b} \quad f_{1c}\,]^T, \Delta l_1 = [\,\Delta l_{1a} \quad \Delta l_{1b} \quad \Delta l_{1c}\,]^T \tag{73}$$

$$f + K_e \Delta l_1 = 0 \tag{74}$$

Based on Expressions (10), (53) through (55) and (57), defining matrix A and vector $m_1$ respectively as shown in the following Expressions (75) and (76), the following Expression (77) holds.

[Math. 33]

$$A = \begin{bmatrix} 1 & 1 & 1 \\ \dfrac{R_g}{2}\sin\!\left(-\zeta_1 - \dfrac{\pi}{2}\right) & \dfrac{R_g}{2}\sin\!\left(-\zeta_1 + \dfrac{\pi}{6}\right) & \dfrac{R_g}{2}\sin\!\left(-\zeta_1 + \dfrac{5\pi}{6}\right) \\ \dfrac{R_g}{2}\sin(-\zeta_1) & \dfrac{R_g}{2}\sin\!\left(-\zeta_1 + \dfrac{2\pi}{3}\right) & \dfrac{R_g}{2}\sin\!\left(-\zeta_1 + \dfrac{4\pi}{3}\right) \end{bmatrix} \tag{75}$$

[Math. 34]

$$m_1 = \tag{76}$$

$$\left[\, 0 \quad -k_m\theta_1\!\left\{\dfrac{1}{-\dfrac{R_g\theta_1}{2}\cos(\zeta_1) + l_{1dc}} + \dfrac{1}{-\dfrac{R_g\theta_1}{2}\cos\!\left(\zeta_1 - \dfrac{2\pi}{3}\right) + l_{1dc}} + \dfrac{1}{-\dfrac{R_g\theta_1}{2}\cos\!\left(\zeta_1 - \dfrac{4\pi}{3}\right) + l_{1dc}}\right\} \quad 0 \,\right]^T$$

$$Af + m_1 = 0 \tag{77}$$

(7-2. Control System)

In the seventh embodiment, the drive control amounts $l_{p1a}$, $l_{p1b}$, and $l_{p1c}$ of the wires $1a$, $1b$, and $1c$ are computed so as to compensate for the stretching and contraction of the wires $1a$, $1b$, and $1c$ connected to the actuators $311a'$, $311b$, and $311c$, respectively. The drive control amounts $l_{p1a}$, $l_{p1b}$, and $l_{p1c}$ of the wires $1a$, $1b$, and $1c$ are found by the following Expressions (79) through (81) here.

$$l_{p1a} = l_{k1a} - \Delta l_{1a} \tag{79}$$

$$l_{p1b} = l_{k1b} - \Delta l_{1b} \tag{80}$$

$$l_{p1c} = l_{k1c} - \Delta l_{1c} \tag{81}$$

Accordingly, the compensation amounts $l_{e1a}$, $l_{e1b}$, and $l_{e1c}$ of the wires $1a$, $1b$, and $1c$ are respectively expressed by the following Expressions (82) through (84).

$$l_{e1a} = -\Delta l_{1a} \tag{82}$$

$$l_{e1b} = \Delta l_{1b} \tag{83}$$

$$l_{e1c} = -\Delta l_{1c} \tag{84}$$

FIG. 31 is a diagram illustrating an example of the functional configuration of a continuum robot control system 700 according to the seventh embodiment of the present invention. The continuum robot control system 700 illustrated in FIG. 31 is configured including the continuum robot 710, a continuum robot control device 720, an input device 730, an input device 740, and an input device 750.

The continuum robot control device 720 sets the drive control amount $l_{p1a}$ for driving control of the wire $1a$, the drive control amount $l_{p1b}$ for driving control of the wire $1b$, and the drive control amount $l_{p1c}$ for driving control of the wire $1c$, based on the target bending angle $\theta_{1ref}$ of the bendable portion of the continuum robot 710 input from the input device 730, the target rotation angle $\zeta_{1ref}$ of the bendable portion of the continuum robot 710 input from the input device 740, and the center axis length $l_{1dc}$ input from the input device 750. The continuum robot control device 720 then outputs a driving command $\tau_{1a}$ based on the drive control amount $l_{p1a}$, a driving command $\tau_{1b}$ based on the drive control amount $l_{p1b}$, and a driving command $\tau_{1c}$ based on the drive control amount $l_{p1c}$, to the continuum robot 710 (or more specifically, the actuators $311a'$, $311b$, and $311c$).

The continuum robot control device 720 illustrated in FIG. 31 is configured including a kinematics computing unit 721, a compensation amount computing unit 722, an adding unit 723, and a position control unit 724.

Based on the target bending angle $\theta_{1ref}$ of the bendable portion of the continuum robot 710 input from the input device 730, the target rotation angle $\zeta_{1ref}$ of the bendable portion of the continuum robot 710 input from the input device 740, and the center axis length $l_{1dc}$ input from the input device 750, the kinematics computing unit 721 computes the driving amounts $l_{k1a}$, $l_{k1b}$, and $l_{k1c}$ based on the kinematic model, using Expressions (69) through (71).

The compensation amount computing unit 722 computes the displacements $\Delta l_{1a}$, $\Delta l_{1b}$, and $\Delta l_{1c}$ for each of the wires $1a$, $1b$, and $1c$, using Expression (78), and further computes the compensation amounts $l_{e1a}$, $l_{e1b}$, and $l_{e1c}$, using Expressions (82) through (84). The wire displacement $\Delta l_1$ is uniquely determined from the bending angle $\theta_1$, rotation angle $\zeta_1$, and center axis length $l_{1dc}$, which can be clearly understood from the right side of Expression (78). Accordingly, the compensation amount computing unit 722 according to the present embodiment can compute the displacements $\Delta l_{1a}$, $\Delta l_{1b}$, and $\Delta l_{1c}$ without using iterative calculation, in the same way as with the first embodiment.

The adding unit 723 adds the driving amounts $l_{k1a}$, $l_{k1b}$, and $l_{k1c}$ calculated by the kinematics computing unit 721 and the compensation amounts $l_{e1a}$, $l_{e1b}$, and $l_{e1c}$ calculated by the compensation amount computing unit 722, thereby computing the driving control amounts $l_{p1a}$, $l_{p1b}$, and $l_{p1c}$, for each of the wires $1a$, $1b$, and $1c$.

The position control unit 724 outputs a driving command $\tau_{1a}$ based on the drive control amount $l_{p1a}$, a driving command $\tau_{1b}$ based on the drive control amount $l_{p1b}$, and a driving command $\tau_{1c}$ based on the drive control amount $l_{p1c}$, to the continuum robot 710 (or more specifically, the actuators $311a'$, $311b$, and $311c$).

While the present embodiment uses the center axis length $l_{1dc}$ as the length of the bendable portion to be input from the input unit 750 to the kinematics computing unit 721 and compensation amount computing unit 722, one of the wire lengths $l_{1a1}$, $l_{1b1}$, and $l_{1c1}$ may be used for example. Also, although the continuum robot control device 720 is applied to the continuum robot 710 having one bendable portion that can be bent three-dimensionally in the present embodiment, application may be made to the continuum robot 110 that curves on a plane as in the first embodiment, or the continuum robot 410 that has multiple bendable portions 312 as in the fourth embodiment.

(7-3. Simulation)

The control system according to the seventh embodiment is applied to the continuum robot 710 that can drive all three wires 1a, 1b, and 1c. Note that both the length $l_{1dc}$ and the length $l_{10}$ are 10 mm in the present embodiment.

FIG. 32 is a characteristics diagram illustrating the relation between target bending angle and driving control amounts $l_{p1a}$, $l_{p1b}$, and $l_{p1c}$ according to the seventh embodiment of the present invention. The horizontal axis in the characteristics diagram of FIG. 32 is the target bending angle $\theta_{1ref}$, and the vertical axis is the wire driving distance.

Specifically, FIG. 32 shows the driving control amounts $l_{p1a}$, $l_{p1b}$, and $l_{p1c}$, by a solid line, dotted line, and dashed line, respectively, in a case where the target rotation angle $\zeta_{1ref}$ is 0 degrees, and the target bending angle $\theta_{1ref}$ is changed from −90 degrees to 90 degrees. The continuum robot control device 720 according to the seventh embodiment drives the three wires 1a, 1b, and 1c, so when the target bending angle changes, the driving control amounts of all of the wires 1a, 1b, and 1c, including the wire 1a, increase or decrease, as illustrated in FIG. 32. Also, the continuum robot control device 720 according to the present embodiment computes the driving control amounts $l_{p1a}$, $l_{p1b}$, and $l_{p1c}$ so that the center axis length is constantly $l_{1dc}$, so in a case where the target bending angle $\theta_{1ref}$ is positive, the driving direction of the wire 1a situated on the inner side as to the center axis is in the pulling direction of the wire (negative direction), and the driving direction of the wires 1b and is situated on the outer side as to the center axis is in the pushing direction of the wire (positive direction).

FIG. 33 is a characteristics diagram illustrating the relation between target rotation angle and bending angle error according to the seventh embodiment of the present invention. The horizontal axis in the characteristics diagram of FIG. 33 is the target bending angle $\theta_{1ref}$, and the vertical axis is the bending angle error.

Specifically, FIG. 33 shows bending angle error in a case where the target rotation angle $\zeta_{1ref}$ is 0 degrees and the target bending angle $\theta_{1ref}$ is changed from −90 degrees to 90 degrees. The dashed line in FIG. 33 illustrates a comparative example of a case where the driving amounts $l_{k1a}$, $l_{k1b}$, and $l_{k1c}$ calculated using the kinematics model are used as control input. It can be understood that in this case, a great angle error occurs. On the other hand, the solid line illustrates angle error in a case of using the drive control amounts $l_{p1a}$, $l_{p1b}$, and $l_{p1c}$ calculated using the continuum robot control device 720 according to the seventh embodiment as control input, and it can be seen that the angle error of the bendable portion of the continuum robot 710 is constantly 0. From the above, it can be understood that attitude error of the continuum robot 710 that can drive all three wires 1a, 1b, and 1c can be reduced, by applying the control system according to the seventh embodiment illustrated in FIG. 31.

Other Embodiments

The above-described first through sixth embodiments have been arrangements where the wire 1a of each bendable portion is fixed, and the driving control amount of the other wire 1b or the like being set, thereby compensating for the displacement of the wire 1a that is fixed. That is to say, the above-described first through sixth embodiments are arrangements of continuum robot control devices that control operations of a continuum robot having a bendable portion that can be bent by driving part of multiple wires. However, the present invention may also be applied to an arrangement of a continuum robot control device that controls operations of a continuum robot having a bendable portion that can be bent by driving all of multiple wires, as in the seventh embodiment. In the case of this form, application can be made to arrangements where all wires are driven to compensate for displacement of the wires themselves, and arrangements where there are wires that compensate driving amount (predetermined wire) and wires that do not compensate driving amount (other wire).

Although friction between wires and wire guides, and between wires and the elongated portion have not been taken into consideration in the above-described first through seventh embodiments, the displacement may be computed taking frictional force into consideration, if the frictional force is known. Specifically, an arrangement may be made where the displacement is computed using the following Expression (85) where frictional forces $f_{r1a}$ and $f_{r1b}$ are added to the left side of Expression (9), instead of Expression (9).

$$f_{1a} + f_{r1a} = -k_e \Delta l_{1a}, f_{1b} + f_{r1b} = -k_e \Delta l_{1b} \qquad (85)$$

Note that in this embodiment as well, the driving amount of the wires can be compensated for using compensation amounts calculated based on displacement of any one of multiple wires pertaining to the same bendable portion, in the same way as with the first embodiment.

The present invention can be realized by processing of supplying a program that realizes one or more functions of the above-described embodiments to a system or device via a network or storage medium, and one or more processors of a computer of the system or device reading out and executing the program. The present invention can also be realized by a circuit that realizes one or more functions (e.g., an application-specific integrated circuit (ASIC)). The program, and a computer-readable storage medium storing the program, are encompassed by the present invention.

The above-described embodiments of the present invention are only exemplary illustrations of carrying out the present invention, and the technical scope of the present invention should not be restrictively interpreted by these. That is to say, the present invention can be carried out in various forms without departing from the technical spirit or primary features thereof.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2018-056793, filed Mar. 23, 2018, and Japanese Patent Application No. 2019-016022, filed Jan. 31, 2019, which are hereby incorporated by reference herein in their entirety.

The invention claimed is:

1. A continuum robot control device configured to control operations of a continuum robot having a bendable portion that is bent by driving at least part of a plurality of wires, the continuum robot control device comprising:
a first computing device configured to compute a driving amount of the at least part of the plurality of wires, based on a target bending angle that is a target value for a bending angle of the bendable portion, and based on a target rotation angle that is a target value for a rotation angle of the bendable portion;
a second computing device configured to compute a compensation amount for compensation of an error in the driving amount due to stretching and contraction of the wires, based on the target bending angle, the target rotation angle and a displacement of one of the plurality of wires at the target bending angle and the target rotation angle; and
a setting device configured to set a driving control amount of performing driving control of the at least part of the plurality of wires, based on the driving amount calculated at the first computing device and the compensation amount calculated at the second computing device,
wherein the second computing device is further configured to:
update, in accordance with input of the target bending angle, and a first candidate value of the displacement at the one wire, to a second candidate value at another one wire,
calculate a compensation amount regarding the another one wire using the second candidate value as the displacement of the another one wire,
output the second candidate value to calculate the compensation amount as the displacement of the another wire in a case where the second candidate value has converged to a constant value, and
output the second candidate value to update candidate value of the displacement as the first candidate value in a case where the second candidate value has not converged to a constant value.

2. The continuum robot control device according to claim 1, wherein the continuum robot has a plurality of the bendable portions disposed serially to each other,
wherein the first computing device computes the driving amount based on the target bending angle, for each bendable portion of the plurality of bendable portions,
wherein the second computing device computes the compensation amount for each bendable portion of the plurality of bendable portions, and
wherein the setting device sets the driving control amount based on the driving amount calculated by the first computing device and the compensation amount calculated by the second computing device, for each bendable portion of the plurality of bendable portions.

3. The continuum robot control device according to claim 1 wherein the second computing device calculates displacement of one wire of the plurality of wires in accordance with input of the target bending angle, and wherein the second computing device computes a compensation amount of another one of the wires based on the calculated displacement of the one wire of the plurality of wires.

4. The continuum robot control device according to claim 1, wherein the second computing device is further configured to:
compute wire length for each of the plurality of wires at the bendable portion, in accordance with input of the target bending angle and the first candidate value,
compute bending moment for each of the plurality of wires, in accordance with input of the target bending angle and the wire length of the plurality of wires,
compute, in accordance with input of the bending moment at the plurality of wires, tensile force at the plurality of wires, and
compute the second candidate value in accordance with input of the tensile force.

5. The continuum robot control device according to claim 4, wherein the second computing device the updating unit is further configured to:
update a candidate value in displacement of the plurality of wires including the another wire, as the first candidate value,
compute wire length for each of the plurality of wires at the bendable portion, in accordance with input of the target bending angle and the first candidate value,
compute bending moment for each of the plurality of wires, in accordance with input of the target bending angle, a target rotation angle that is a target value of a rotation angle of the bendable portion, and the wire length of the plurality of wires,
compute tensile force of the plurality of wires, in accordance with input of the bending moment at the plurality of wires, and
compute the second candidate value in the displacement of the plurality of wires including the another wire, in accordance with input of the tensile force at the plurality of wires.

6. A continuum robot control device configured to control operations of a continuum robot having a bendable portion that is bent by driving at least part of a plurality of wires, the continuum robot control device comprising:
a first computing device configured to compute a driving amount of the at least part of the plurality of wires, based on a target bending angle that is a target value for a bending angle of the bendable portion, and based on a target rotation angle that is a target value for a rotation angle of the bendable portion;

a second computing device configured to compute a compensation amount for compensation of an error in the driving amount due to stretching and contraction of the wires, based on the target bending angle, the target rotation angle and a displacement of one of the plurality of wires at the target bending angle and the target rotation angle; and a setting device configured to set a driving control amount of performing driving control of the at least part of the plurality of wires, based on the driving amount calculated at the first computing device and the compensation amount calculated at the second computing device, the continuum robot further comprising:

a third computing device configured to compute an amount of movement of a distal end of the bendable portion, in accordance with input of a movement amount of the continuum robot in a longitudinal direction, and a first driving control amount candidate value in the driving control amount of wires, and a reference angle updating device configured to update the target bending angle, in accordance with input of amount of movement of the distal end of the bendable portion, wherein the setting device computes a second driving control amount candidate value for the driving control amount of wires, based on a driving amount calculated based on the target bending angle that the first computing device has updated at the reference angle updating device, and a compensation amount calculated based on the target bending angle that the second computing device has updated at the reference angle updating device, sets the second driving control amount candidate value as the driving control amount in a case where the second driving control amount candidate value has converged to a constant value, and outputs the second driving control amount candidate value to the third computing device as the first driving control amount candidate value in a case where the second driving control amount candidate value has not converged to a constant value.

7. The continuum robot control device according to claim 1, wherein the length of the wires is ten times or more the length of the bendable portion.

8. A computer-readable storage medium storing a program configured to cause a computer to function as the devices of the continuum robot control device according to claim 1.

9. The continuum robot control device according to claim 1, wherein the compensation amount for the stretching and contraction of first wire of the plurality of wires is based on amount of displacement of the first wire and a second wire of the plurality of wires.

* * * * *